(12) United States Patent
Yen et al.

(10) Patent No.: US 10,103,337 B1
(45) Date of Patent: Oct. 16, 2018

(54) ORGANIC ELECTROLUMINESCENT MATERIAL AND USING THE SAME

(71) Applicants: Feng-Wen Yen, Taipei (TW);
Chin-Min Teng, Miaoli (TW);
Li-Chieh Chuang, Nantou (TW)

(72) Inventors: Feng-Wen Yen, Taipei (TW);
Chin-Min Teng, Miaoli (TW);
Li-Chieh Chuang, Nantou (TW)

( * ) Notice: Subject to any disclaimer, the term of this patent is extended or adjusted under 35 U.S.C. 154(b) by 0 days.

(21) Appl. No.: 15/499,938

(22) Filed: Apr. 28, 2017

(51) Int. Cl.
| | | |
|---|---|---|
| *H01L 51/00* | (2006.01) |
| *C09K 11/02* | (2006.01) |
| *C07D 401/04* | (2006.01) |
| *C07D 401/10* | (2006.01) |
| *C07D 401/14* | (2006.01) |
| *C09K 11/06* | (2006.01) |
| *H01L 51/52* | (2006.01) |
| *H01L 51/50* | (2006.01) |

(52) U.S. Cl.
CPC ........ *H01L 51/0072* (2013.01); *C07D 401/04* (2013.01); *C07D 401/10* (2013.01); *C07D 401/14* (2013.01); *C09K 11/025* (2013.01); *C09K 11/06* (2013.01); *H01L 51/006* (2013.01); *H01L 51/0056* (2013.01); *H01L 51/0067* (2013.01); *H01L 51/0074* (2013.01); *H01L 51/0077* (2013.01); *H01L 51/0085* (2013.01); *C09K 2211/1007* (2013.01); *C09K 2211/1011* (2013.01); *C09K 2211/1029* (2013.01); *C09K 2211/1059* (2013.01); *C09K 2211/1092* (2013.01); *C09K 2211/185* (2013.01); *H01L 51/0052* (2013.01); *H01L 51/5016* (2013.01); *H01L 51/5072* (2013.01); *H01L 51/5096* (2013.01); *H01L 51/5206* (2013.01); *H01L 51/5221* (2013.01)

(58) Field of Classification Search
None
See application file for complete search history.

(56) References Cited

U.S. PATENT DOCUMENTS

| | | |
|---|---|---|
| 8,993,130 B2 | 3/2015 | Yen et al. |
| 9,190,619 B2 | 11/2015 | Yen et al. |
| 2014/0166988 A1* | 6/2014 | Yen ..................... H01L 51/0058 257/40 |

* cited by examiner

*Primary Examiner* — Jay Yang

(57) ABSTRACT

There is provided a novel material of formula(1) or formula (2) and the organic EL device employing the novel material as phosphorescent light emitting host of emitting layer, delayed fluorescence dopant of emitting layer, and hole blocking layer can display good performance like as lower driving voltage and power consumption, increasing efficiency and life time of organic EL device.

formula(1)

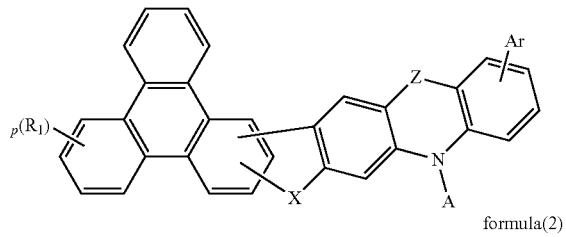

formula(2)

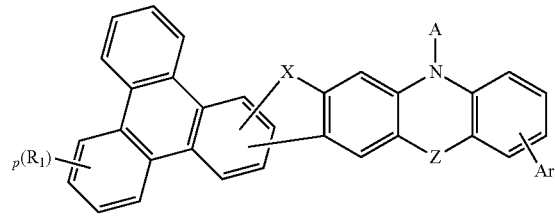

wherein p, X, Z, $R_1$, Ar and A are the same definition as described in the present invention.

14 Claims, 1 Drawing Sheet

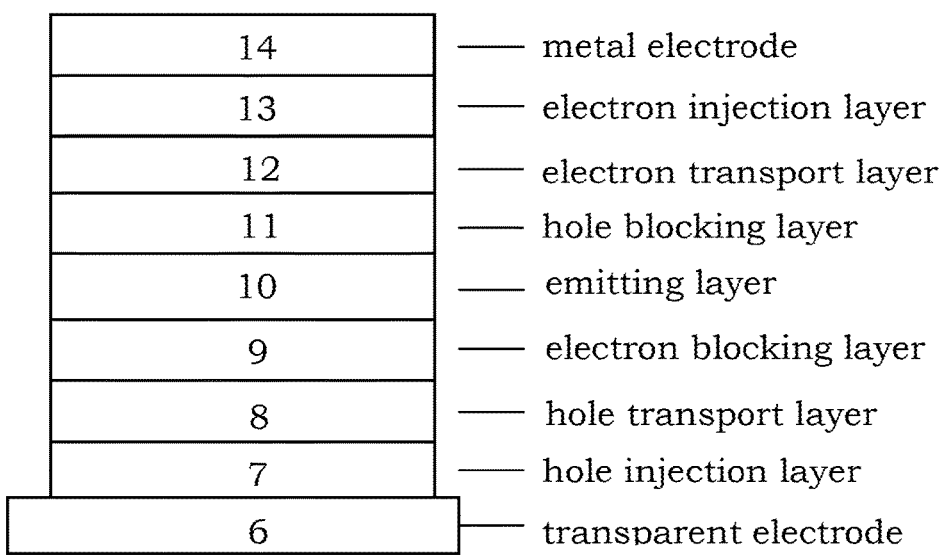

ORGANIC ELECTROLUMINESCENT MATERIAL AND USING THE SAME

FIELD OF INVENTION

There is provided a material for organic electroluminescence (herein referred to as organic EL) device having general formula(1) or formula(2), an organic EL device employing the material as phosphorescent emitting host, delayed fluorescent dopant, and hole blocking layer (HBL).

BACKGROUND OF THE INVENTION

An organic EL device is composed of layers of organic materials situated between two electrodes, which include a hole transporting layer (HTL), an emitting layer (EML) and an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is finished by some heavy atom such as iridium, rhodium, platinum, palladium and the phosphorescent transition may be observed from an excited MLCT (metal to ligand charge transfer) state of organic metallic complexes.

Recently, a new type of fluorescent organic EL incorporating mechanism of thermally activated delayed fluorescence (TADF) has been developed by Adachi and coworkers is a promising way to obtain a high efficiency of exciton formation by converting spin-forbidden triplet excitons up to the singlet level by the mechanism of reverse intersystem crossing (RISC) by using a material having a small energy gap between the singlet level and the triplet level. However, further improvement in luminous efficiency of the organic EL device in a high current density region is still desired.

The phosphorescent organic EL utilizes both triplet and singlet excitons. Cause of longer lifetime and the diffusion length of triplet excitons compared to those of singlet excitons, the phosphorescent organic EL generally need an additional hole-blocking layer (HBL) between the emitting layer (EML) and the electron transporting layer (ETL) or the electron transporting layer with hole blocking ability instead of typical ETL. The purpose of the use of HBL or HBETL is to confine the recombination of injected holes and electrons and the relaxation of created excitons within the EML, hence the device's efficiency can be improved. To meet such roles, the hole blocking materials must have HOMO (highest occupied molecular orbital) and LUMO (lowest unoccupied molecular orbital) energy levels suitable to block hole transport from the EML to the ETL and to pass electrons from the ETL to the EML, in addition, the good thermal and electrochemical stability of the materials are also needed.

For full-colored flat panel displays in AMOLED or OLED lighting panel the material used for the phosphorescent dopant for emitting layer are still unsatisfactory in half-life time, efficiency and driving voltage. These organic metallic complexes still have disadvantages for industrial practice use. The phosphorescent dopant with preferential in-plane (horizontal) emitting dipoles are beneficial to optical out-coupling of OLED, since the ratio of vertical emitting dipoles contributing little to external emission is reduced and the radiation pattern of a horizontal emitting dipole is in general more suitable for optical out-coupling. Therefore, an emitter with proper substituents can be helpful to enhance the ratio of horizontal emitting dipole in the emission layer of OLED. Meanwhile, the proper substituents around an emitter can effectively block nearby electrons and holes, so that electrons and holes can easily recombine in the emitter and the efficiency of OLED can be improved.

There continues to be a need for organic EL materials which is able to efficiently transport electrons or holes and block holes, with good thermal stability and more efficient EML materials for high emitting efficiency. According to the reasons described above, the present invention has the objective of resolving such problems of the prior-art and offering a light emitting device which is excellent in its thermal stability, high luminance efficiency, high luminance and long half-life time. The present invention disclose a novel material having general formula(1) or formula(2), used as phosphorescent emitting host, delayed fluorescent dopant, and hole blocking layer (HBL) have good charge carrier mobility and excellent operational durability can lower driving voltage and power consumption, increasing efficiency and half-life time of organic EL device.

SUMMARY OF THE INVENTION

A novel material can be used as phosphorescent emitting host, delayed fluorescent dopant and hole blocking layer (HBL) for organic EL and their use for organic EL device are provided. The material can overcome the drawbacks of the conventional materials like as shorter half-life time, lower efficiency and higher power consumption.

An object of the present invention is to provide the novel material which can be used as hole blocking layer (HBL) material for organic EL device and can efficiently confine excitons to transfer to electron transport layer.

An object of the present invention is to provide the novel material which can be used as phosphorescent host material, delayed fluorescent dopant of emitting layer for organic EL device and increase the efficiency and half-life time.

The present invention has the economic advantages for industrial practice. Accordingly the present invention, the material which can be used for organic EL device is disclosed. The mentioned the material is represented by the following formula(1) or formula(2):

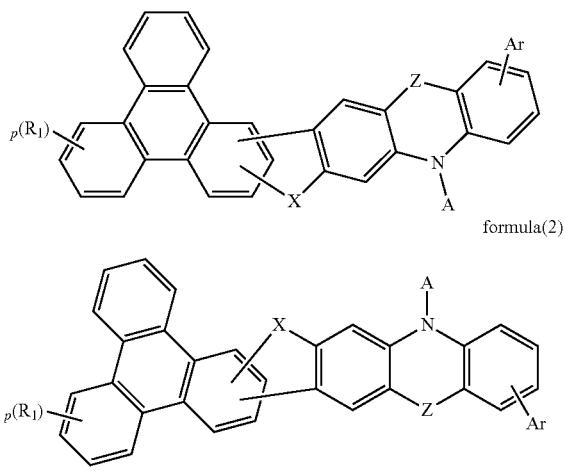

formula(1)

formula(2)

wherein p represents an integer of 0 to 8, X independently represents a divalent bridge selected from the atom or group consisting from O, S, C($R_2$)($R_3$), N($R_4$) and Si($R_5$)($R_6$), Z independently represents a divalent bridge selected from the atom or group consisting from C($R_7$)($R_8$), N($R_9$), Si($R_{10}$)($R_{11}$) and C=O, Ar represents a hydrogen atom, or a fused carbocyclic ring; A is selected from the group consisting of a hydrogen, a substituted or unsubstituted aryl group having 6 to 60 carbon atoms or a substituted or unsubstituted heteroaryl group having 3 to 60 carbon atoms, and provided that A represents a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted quinoline group, a substituted or unsubstituted isoquinoline group, a substituted or unsubstituted quinazoline group, a substituted or unsubstituted phenanthroline group, a substituted or unsubstituted dihydroacridine group, a substituted or unsubstituted phenothiazine group, a substituted or unsubstituted phenoxazine group, and a substituted or unsubstituted dihydrophenazine group; $R_1$ to $R_{11}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms

BRIEF DESCRIPTION OF THE DRAWINGS

FIG. 1 show one example of organic EL device in the present invention. 6 is transparent electrode, 14 is metal electrode, 7 is hole injection layer which is deposited onto 6, 8 is hole transport layer which is deposited onto 7, 9 is electron blocking layer which is deposited onto 8, 10 is delayed fluorescent or phosphorescent emitting layer which is deposited onto 9, 11 is hole blocking layer which is deposited onto 10, 12 is electron transport layer which is deposited onto 11, 13 is electron injection layer which is deposited on to 12.

DESCRIPTION OF THE PREFERRED EMBODIMENTS

What probed into the invention is the material and organic EL device using the material. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the material which can be used as phosphorescent emitting host, delayed fluorescence dopant, and hole blocking layer (HBL) for organic EL device are disclosed. The mentioned the material are represented by the following formula(1) or formula(2):

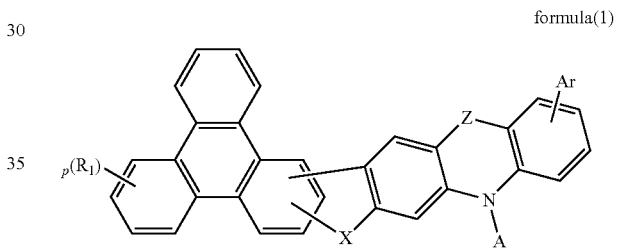

formula(1)

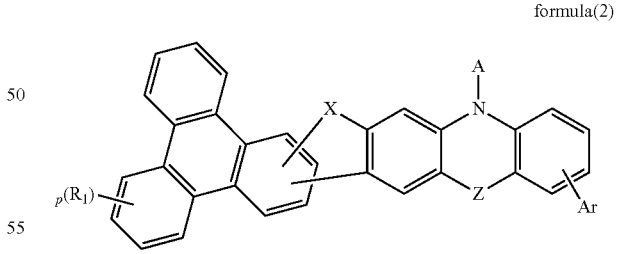

formula(2)

wherein p represents an integer of 0 to 8, X independently represents a divalent bridge selected from the atom or group consisting from O, S, C($R_2$)($R_3$), N($R_4$) and Si($R_5$)($R_6$), Z independently represents a divalent bridge selected from the atom or group consisting from C($R_7$)($R_8$), N($R_9$), Si($R_{10}$)($R_{11}$) and C=O, Ar represents a hydrogen atom, or a fused carbocyclic ring; A is selected from the group consisting of a hydrogen, a substituted or unsubstituted aryl group having 6 to 60 carbon atoms or a substituted or unsubstituted heteroaryl group having 3 to 60 carbon atoms, and provided that A represents a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted quinoline group, a substituted or unsubstituted isoquinoline group, a substituted or unsubstituted quinazoline group, a substituted or unsubstituted phenanthroline group, a substituted or unsubstituted dihydroacridine group, a substituted or unsubstituted phenothiazine group, a substituted or unsubstituted phenoxazine group, and a substituted or unsubstituted dihydrophenazine group; $R_1$ to $R_{11}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

According to the above-mentioned the material formula (1) or formula(2), wherein the A is represented by the following formula(3) to formula(6):

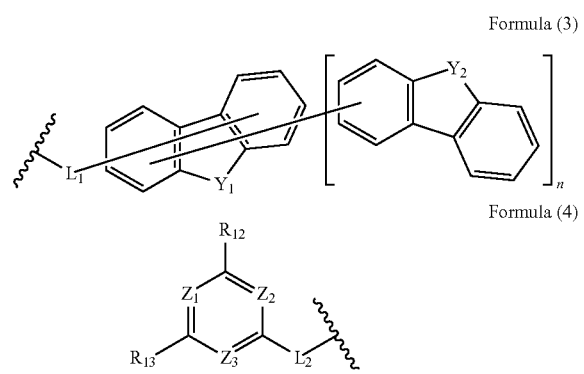

Formula (3)

Formula (4)

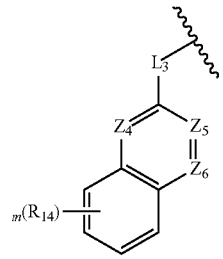

Formula (5)

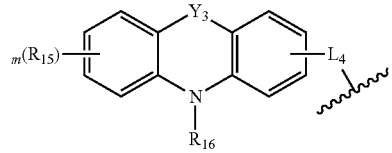

Formula (6)

wherein $L_1$ to $L_4$ represent a single bond, a substituted or unsubstituted arylene group having 6 to 30 ring carbon atoms, or a substituted or unsubstituted heterarylene group having 3 to 30 ring carbon atoms, m represents an integer of 0 to 4, n represents an integer of 0 or 1, $Y_1$ to $Y_3$ independently represent a divalent bridge selected from the atom or group consisting from O, S, $C(R_{17})(R_{18})$ and $N(R_{19})$, $Z_1$ to $Z_6$ represent a nitrogen atom or $C(R_8)$, and each $R_s$ represents a hydrogen, a phenyl, a substituted or unsubstituted alkyl group having 1 to 30 carbon atoms, and a substituted or unsubstituted aryl group having 6 to 30 carbon atoms; $R_{12}$ to $R_{19}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

In this embodiment, some materials are shown below:

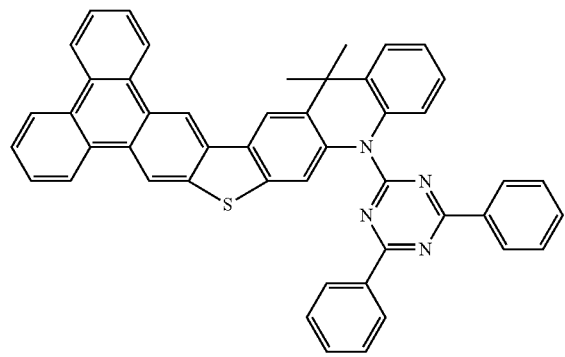

Compound 1

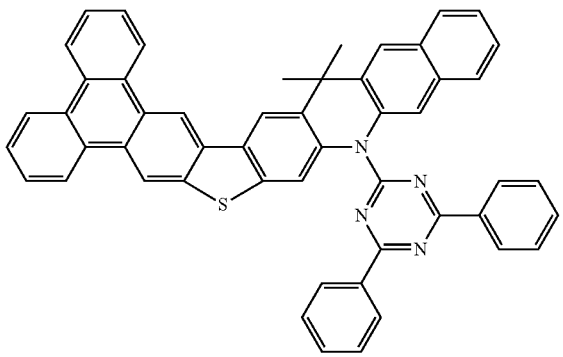

Compound 2

-continued
Compound 3
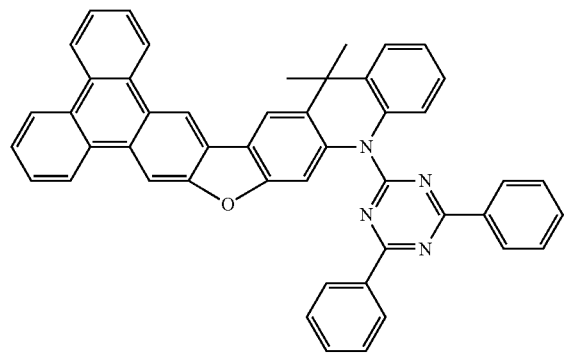
Compound 4
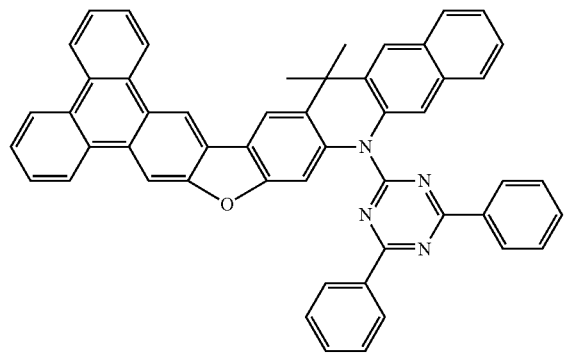
Compound 5
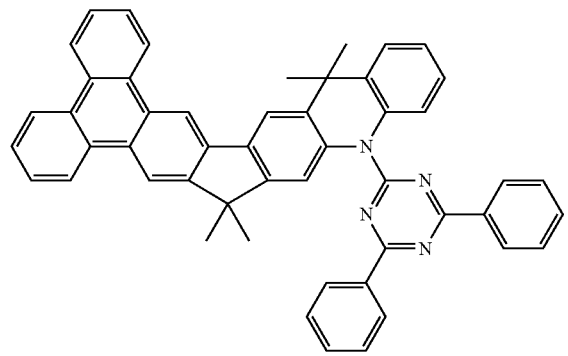
Compound 6
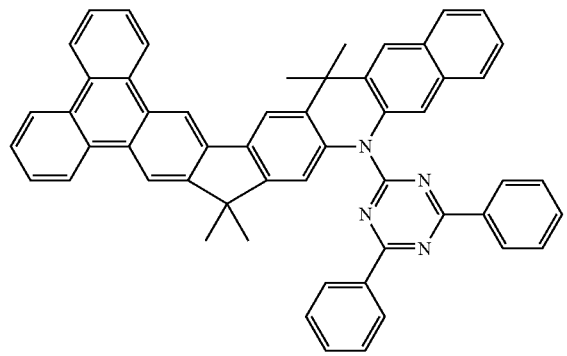
Compound 7
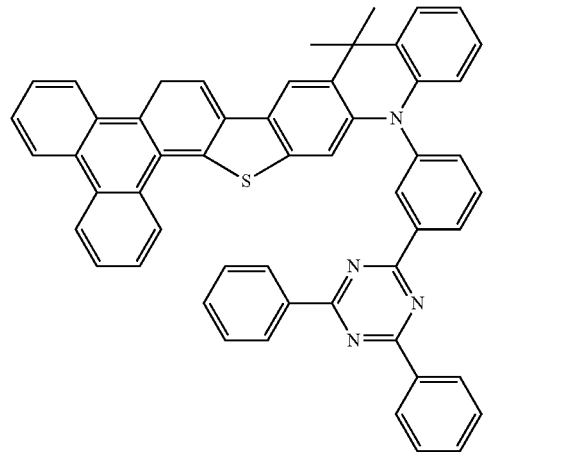
Compound 8
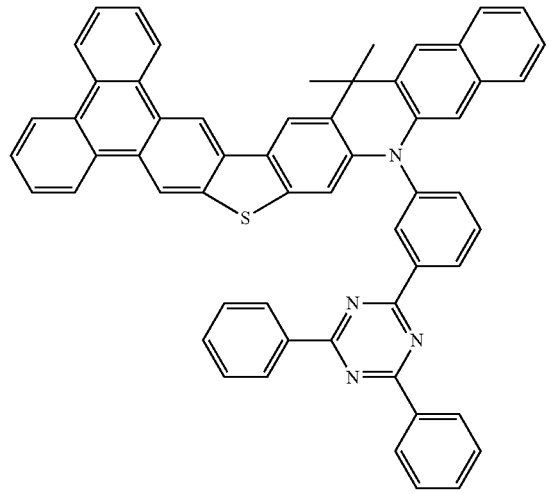
Compound 9
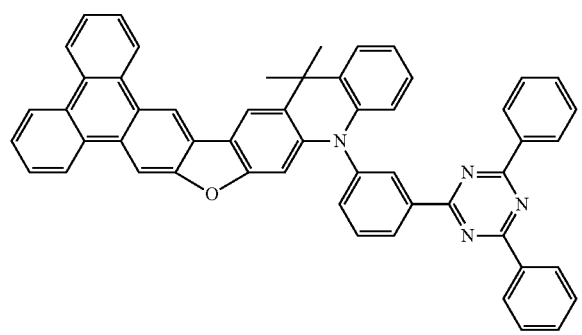
Compound 10
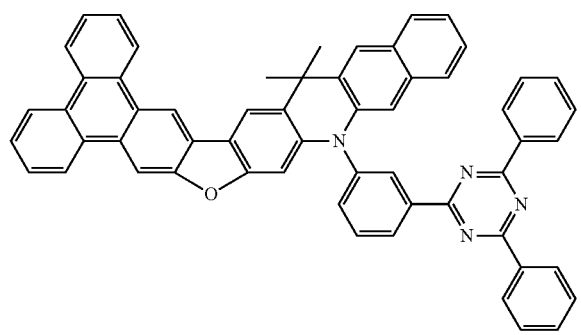

-continued
Compound 11
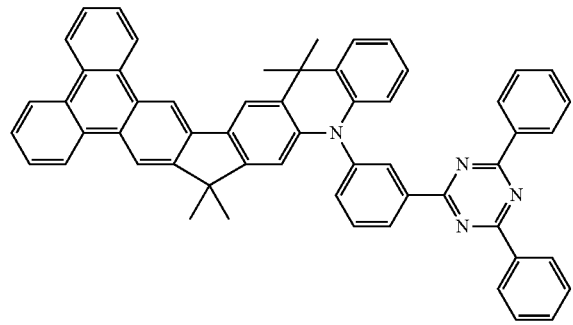
Compound 12
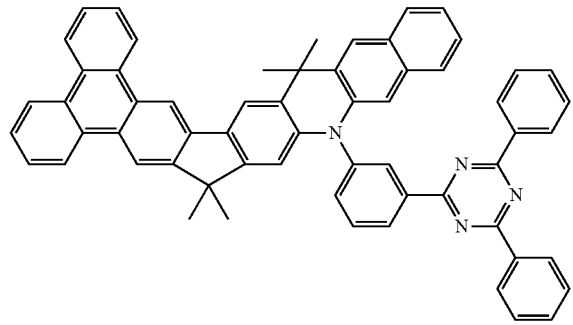
Compound 13
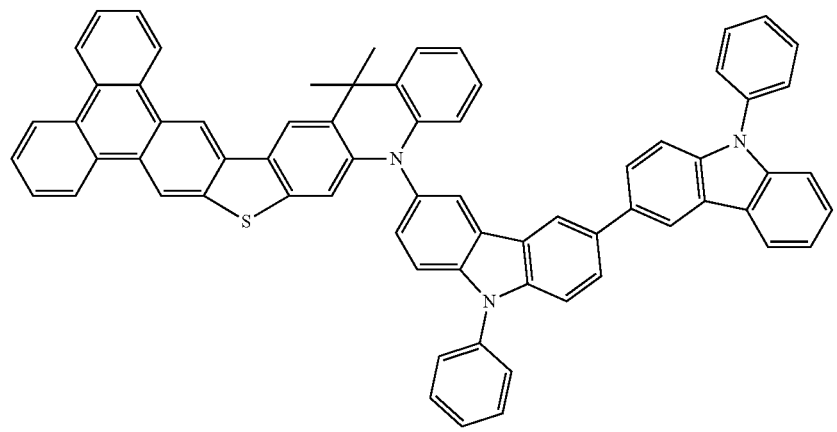
Compound 14
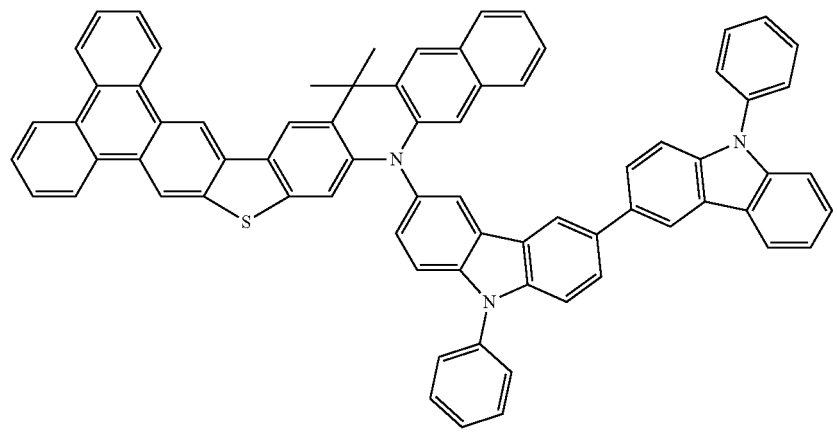
Compound 15
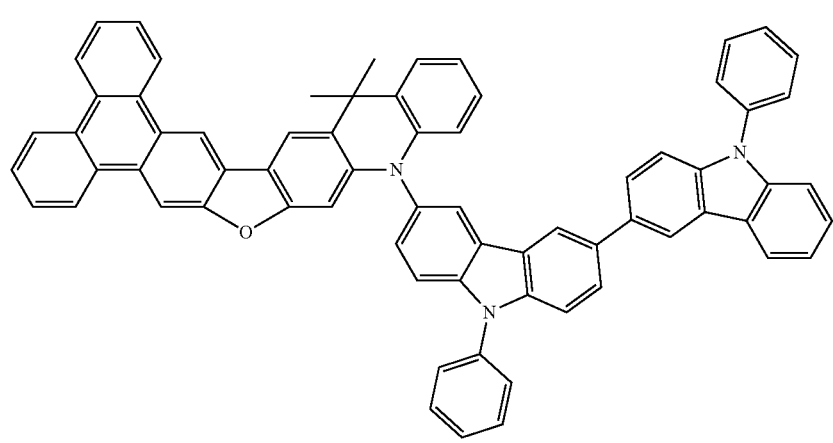

Compound16
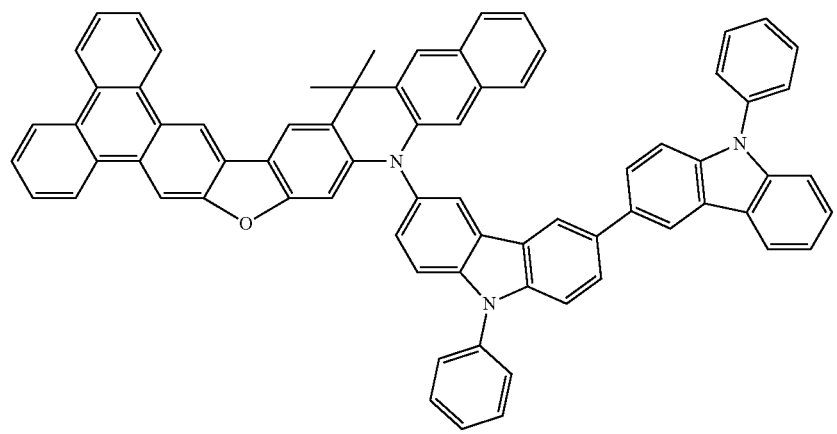
Compound 17
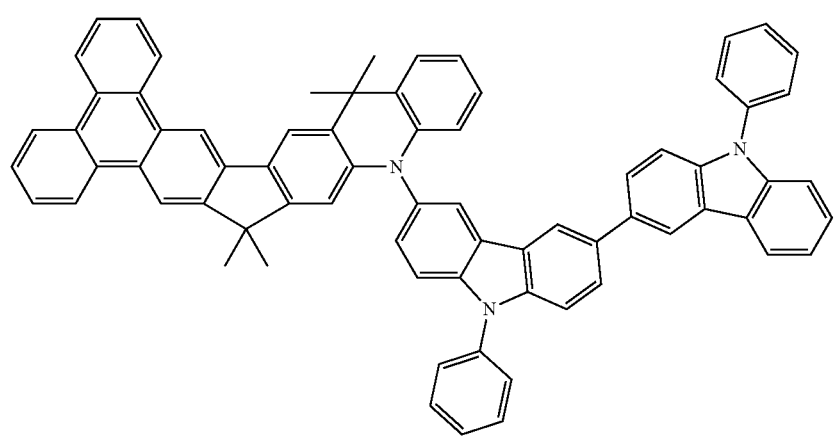
Compound 18
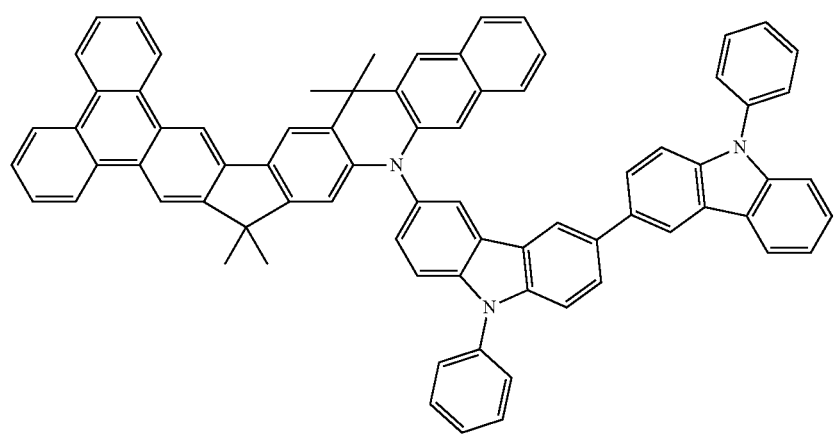

-continued
Compound 19
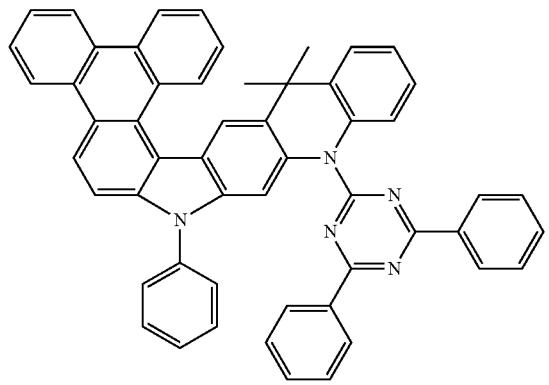
Compound 20
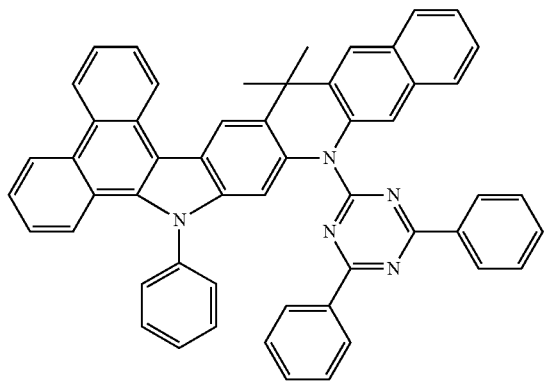
Compound 21
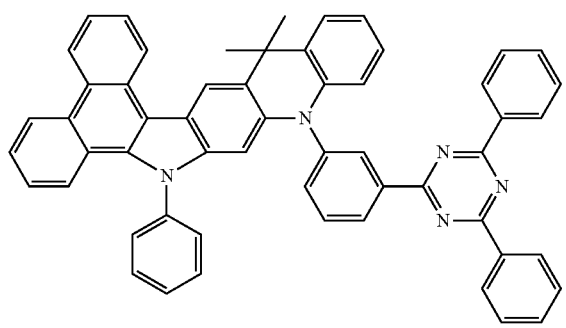
Compound 22
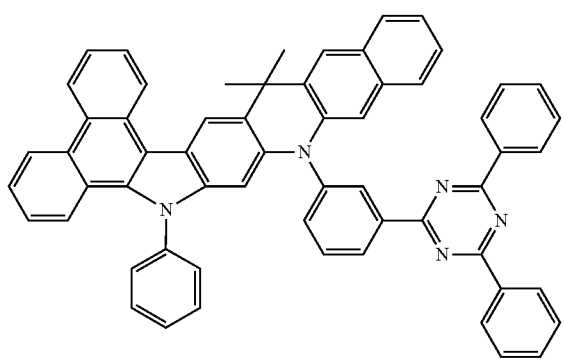
Compound 23
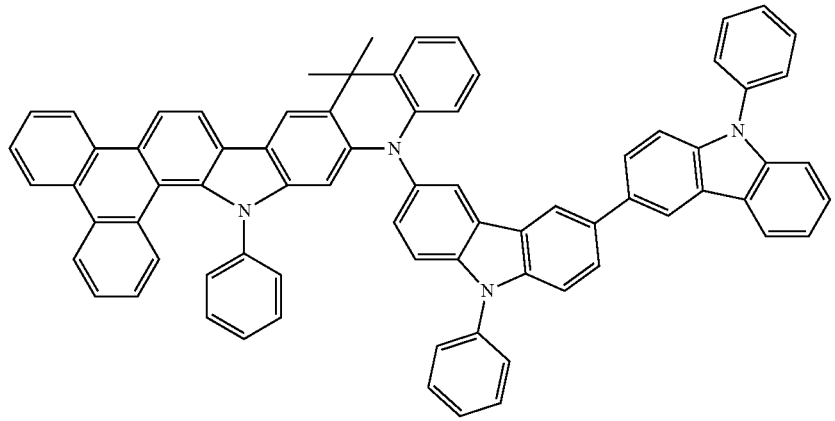
Compound 24
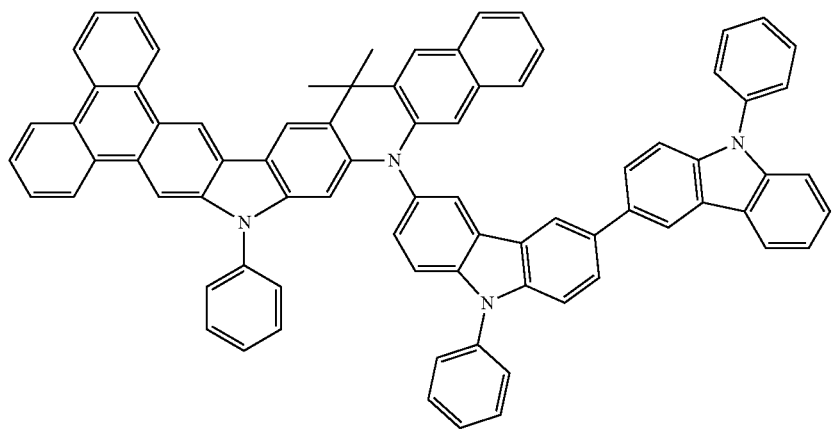

-continued
Compound 25
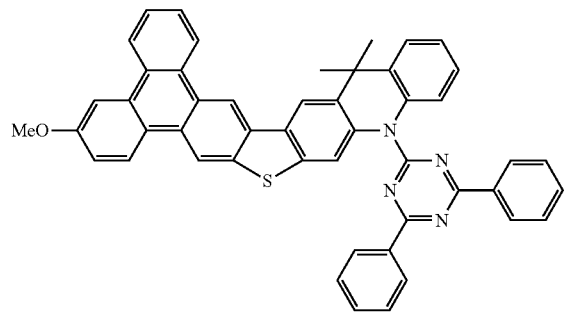
Compound 26
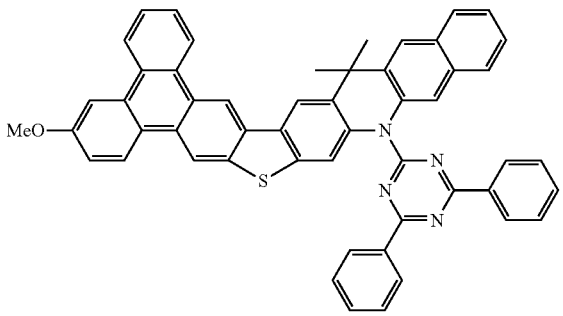
Compound 27
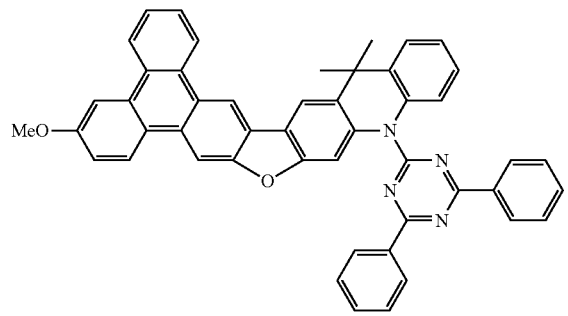
Compound 28
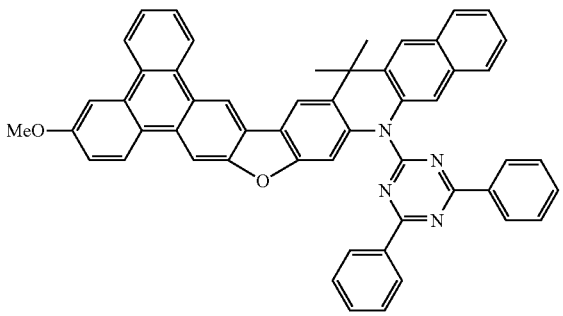
Compound 29
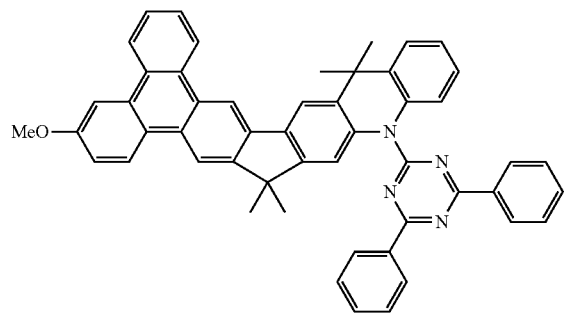
Compound 30
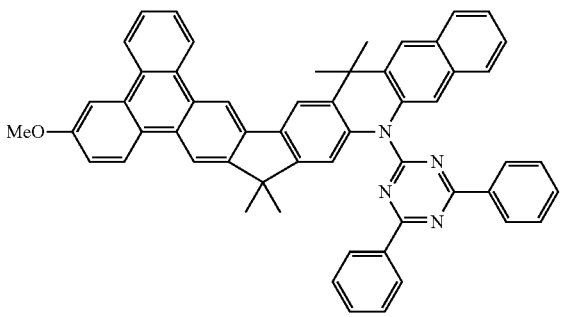
Compound 31
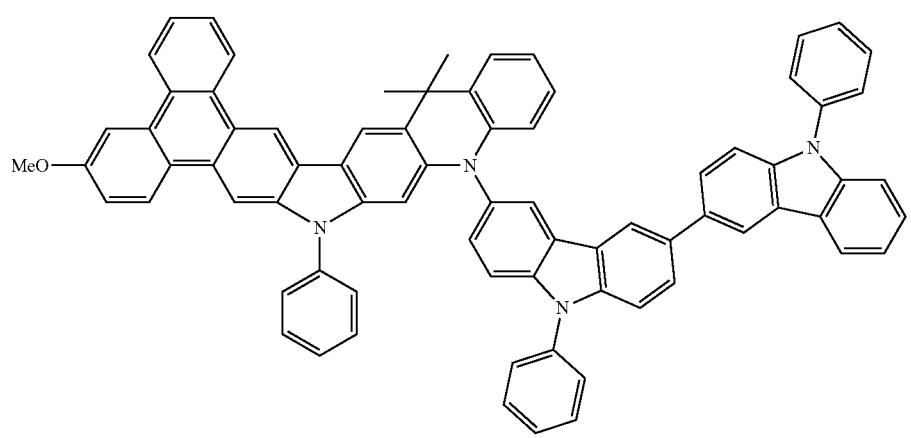

-continued
Compound 32
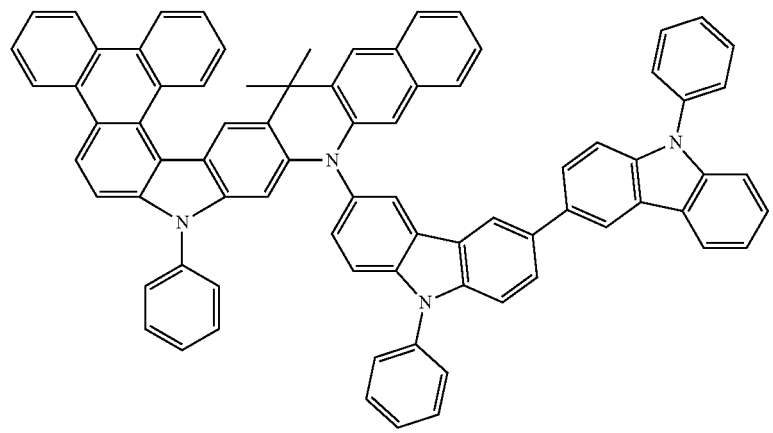
Compound 33
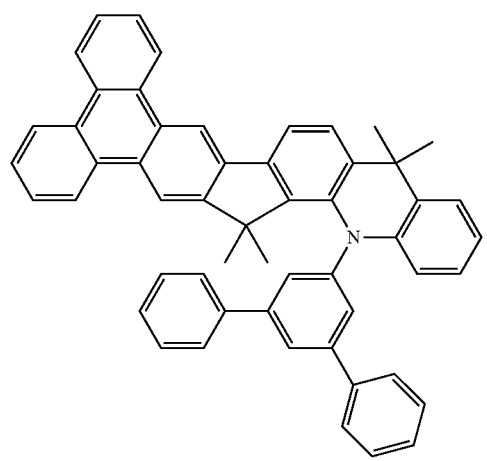
Compound 34
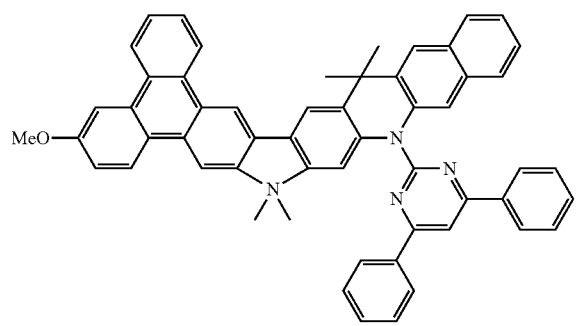
Compound 35
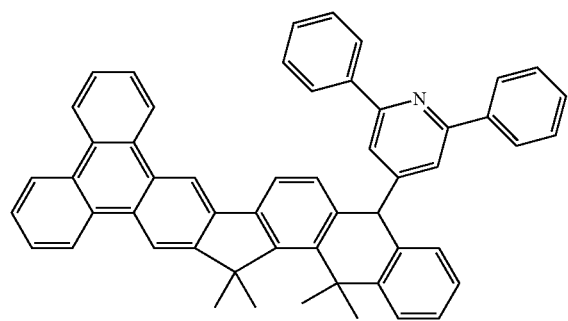
Compound 36
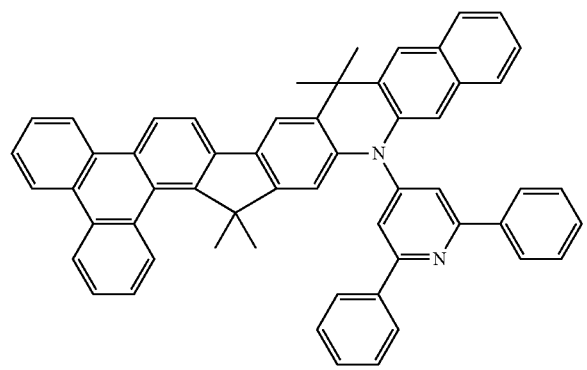

-continued
Compound 37
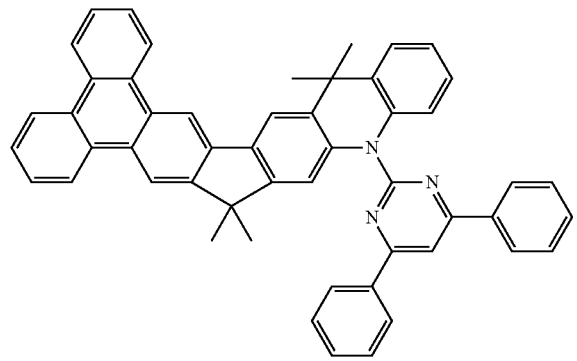
Compound 38
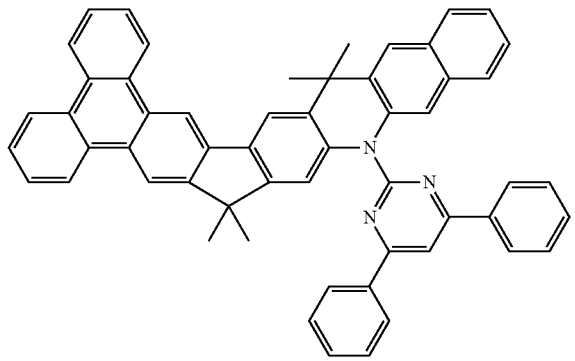
Compound 39
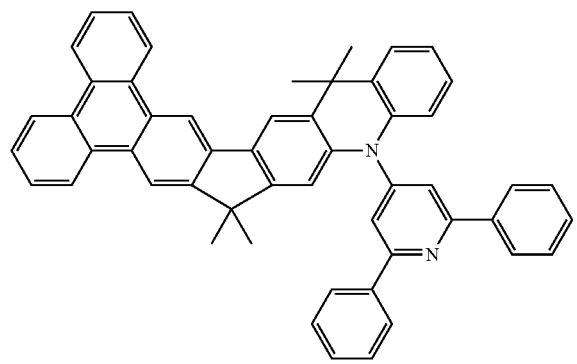
Compound 40
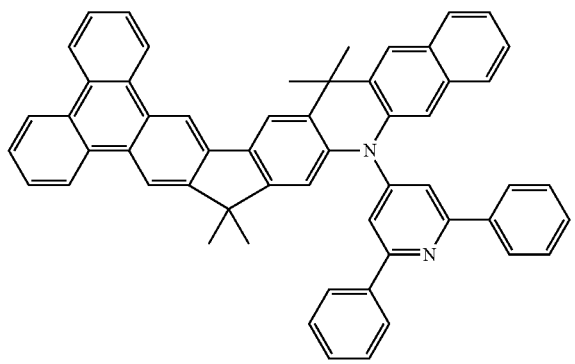
Compound 41
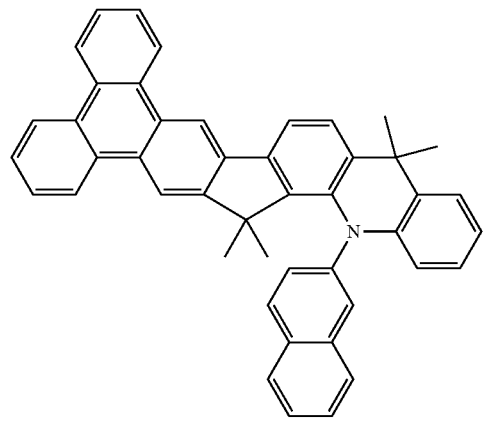
Compound 42
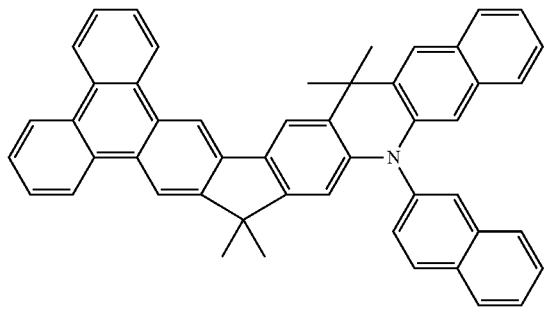
Compound 43
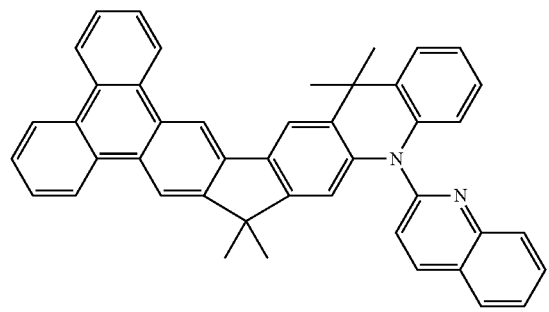
Compound 44
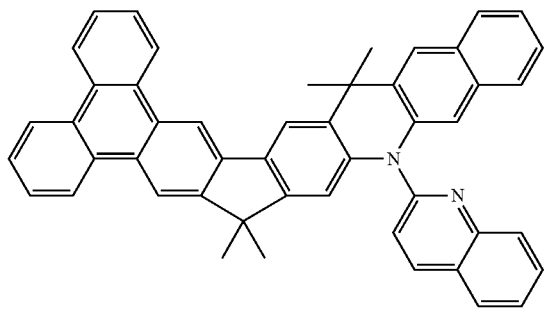

-continued
Compound 45
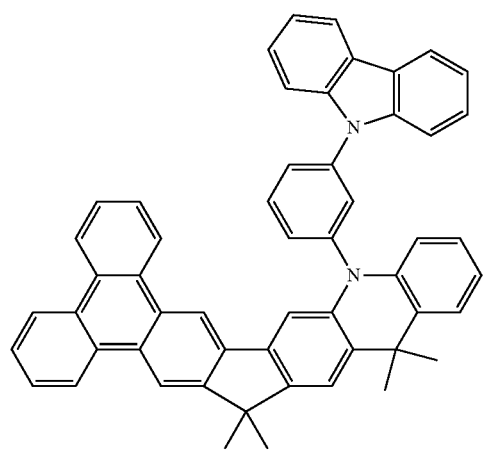
Compound 46
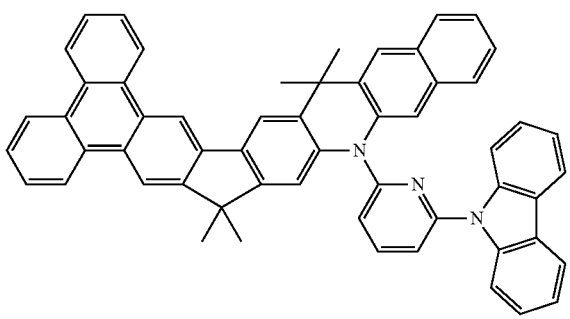
Compound 47
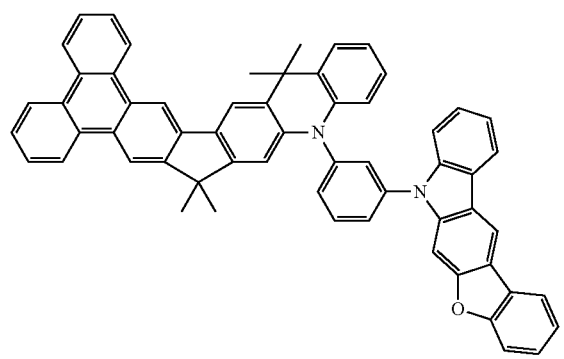
Compound 48
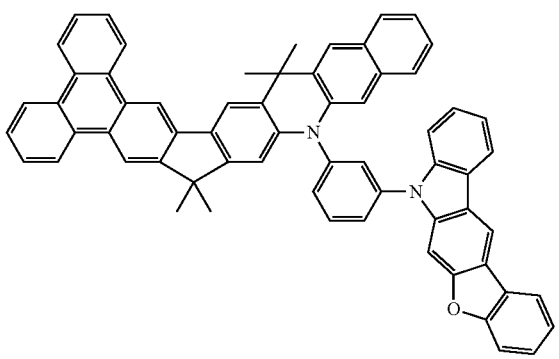
Compound 49
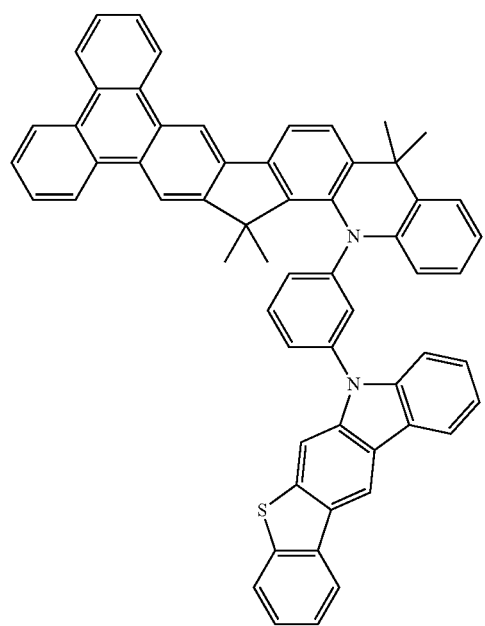
Compound 50
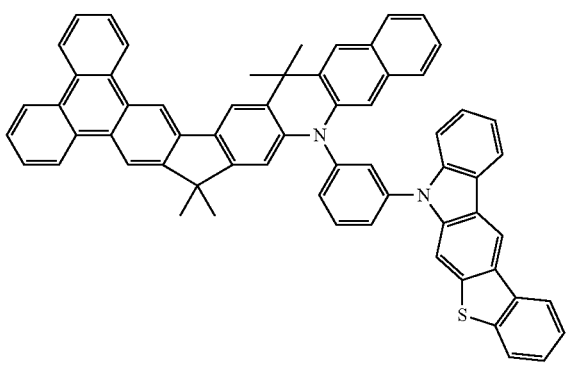

-continued
Compound 51
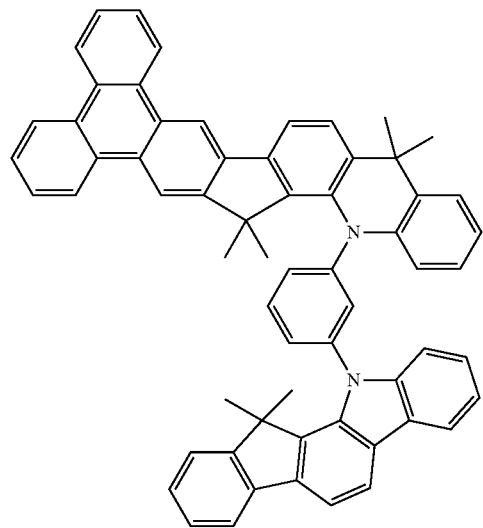
Compound 52
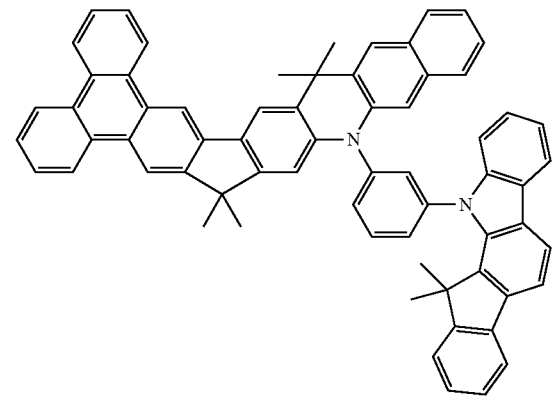
Compound 53
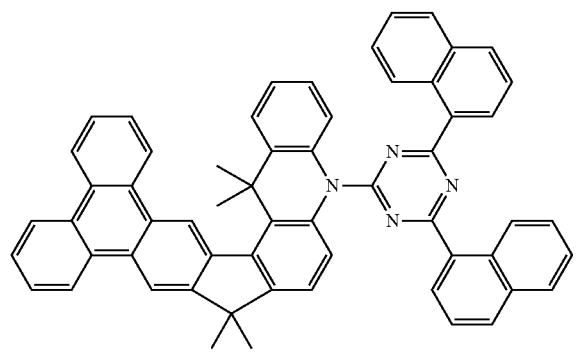
Compound 54
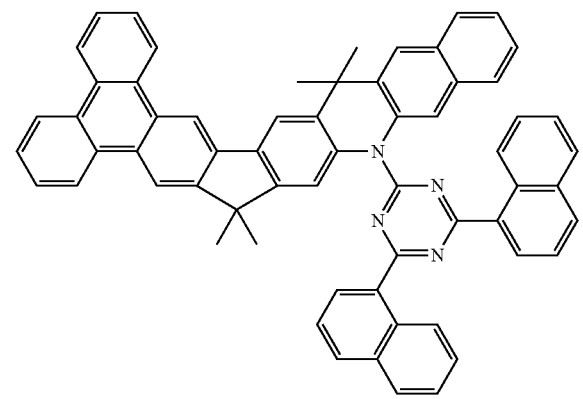
Compound 55
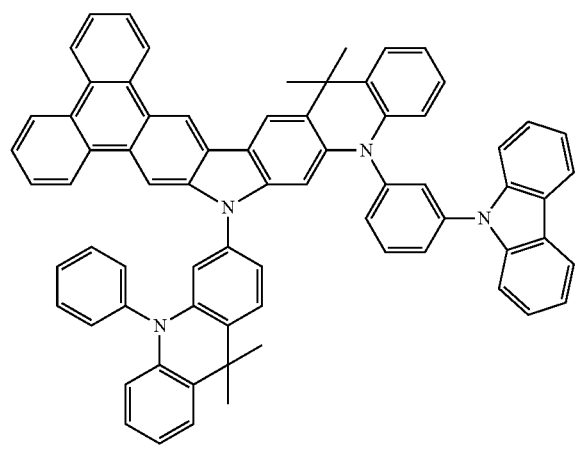
Compound 56
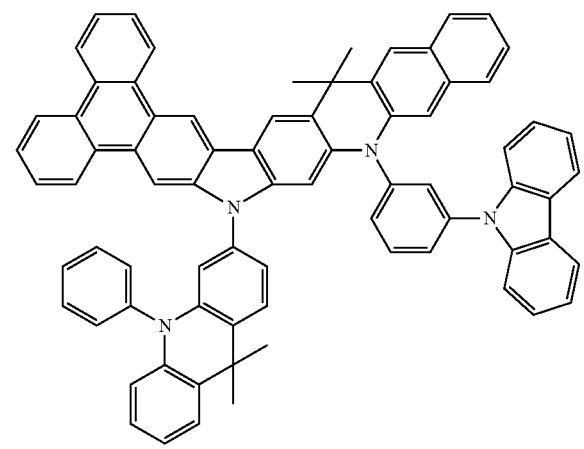

-continued
Compound 57
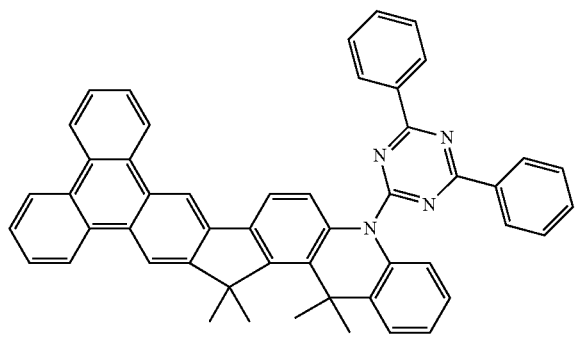
Compound 58
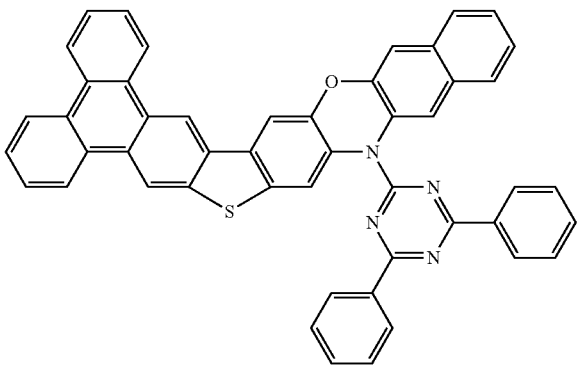
Compound 59
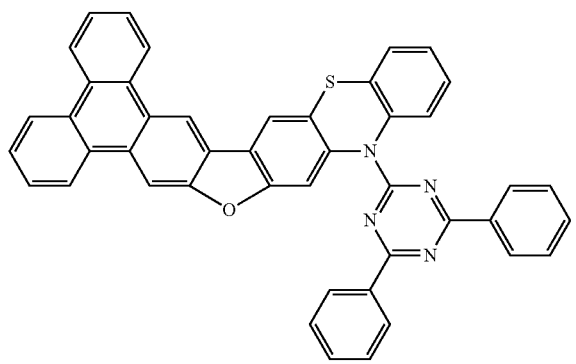
Compound 60
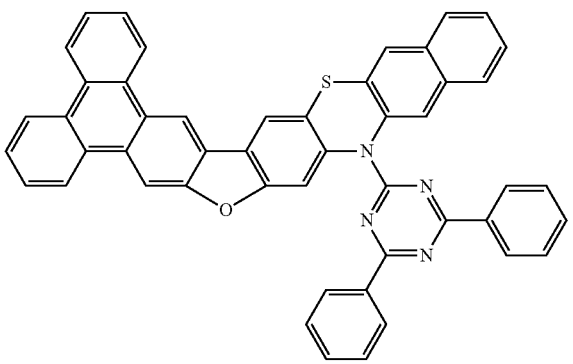
Compound 61
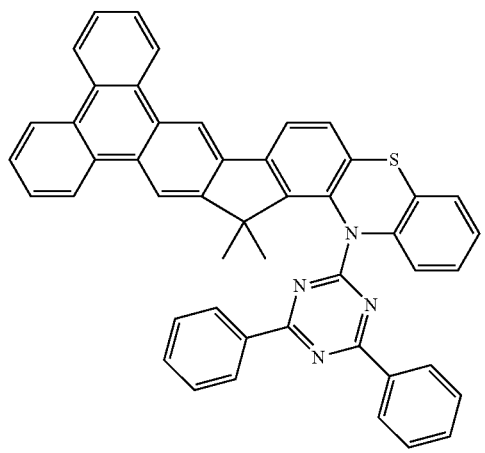
Compound 62
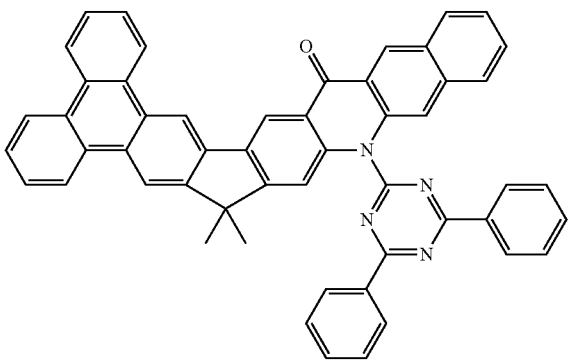
Compound 63
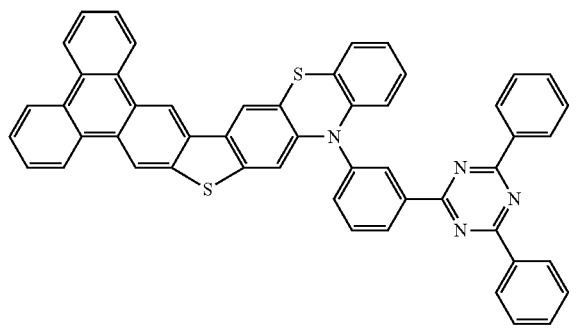
Compound 64
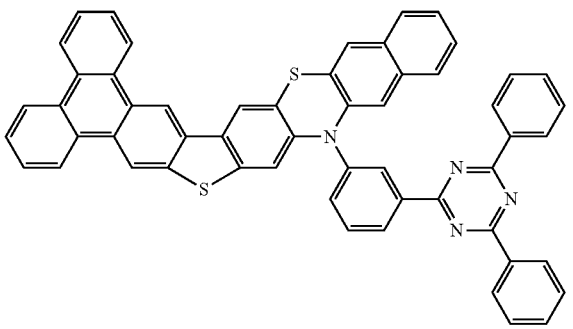

-continued
Compound 65
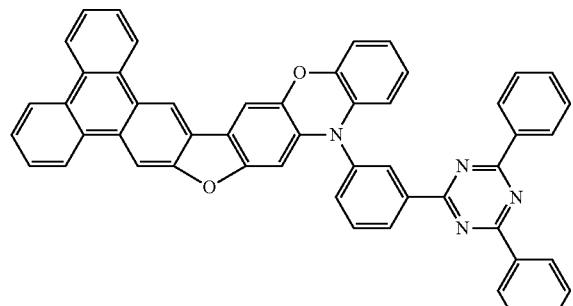
Compound 66
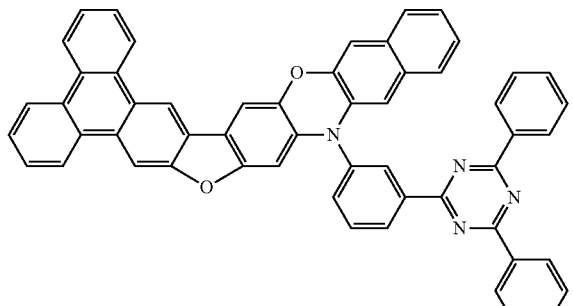
Compound 67
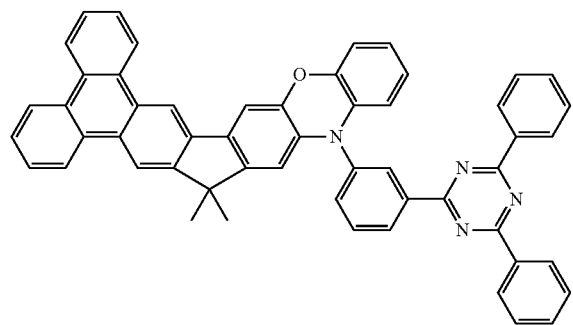
Compound 68
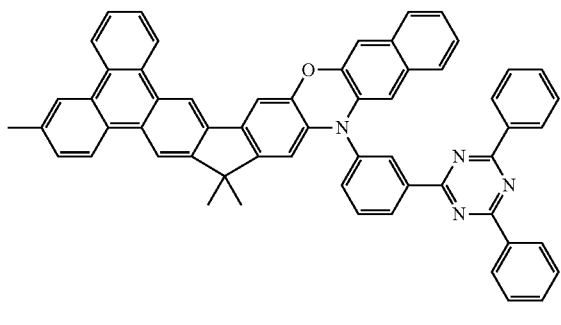
Compound 69
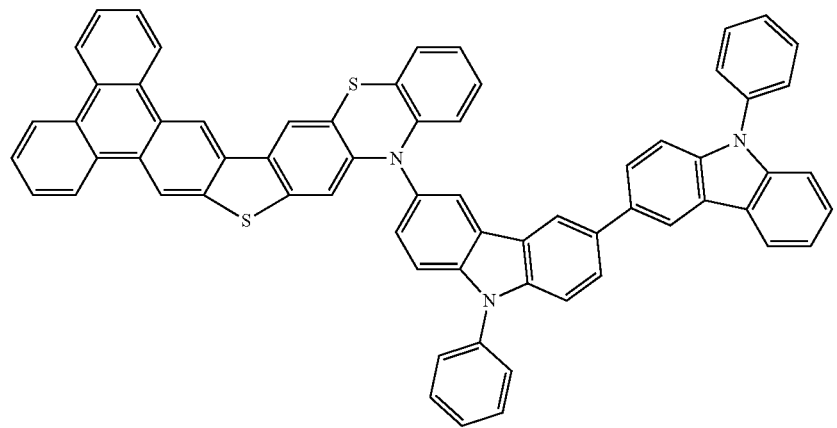
Compound 70
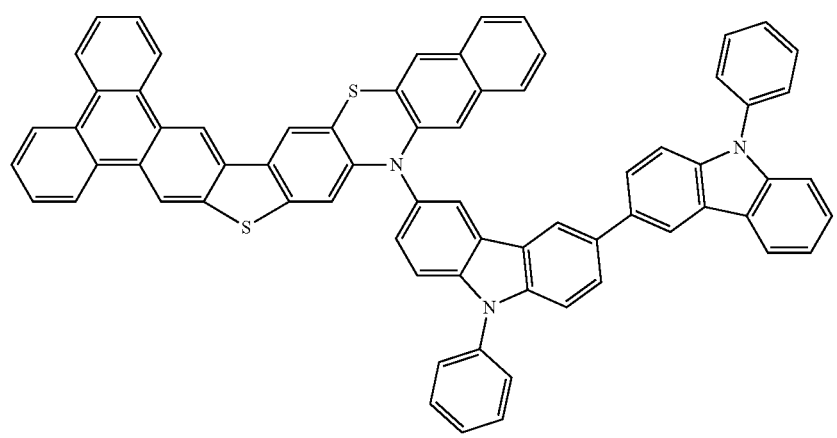

-continued
Compound 71
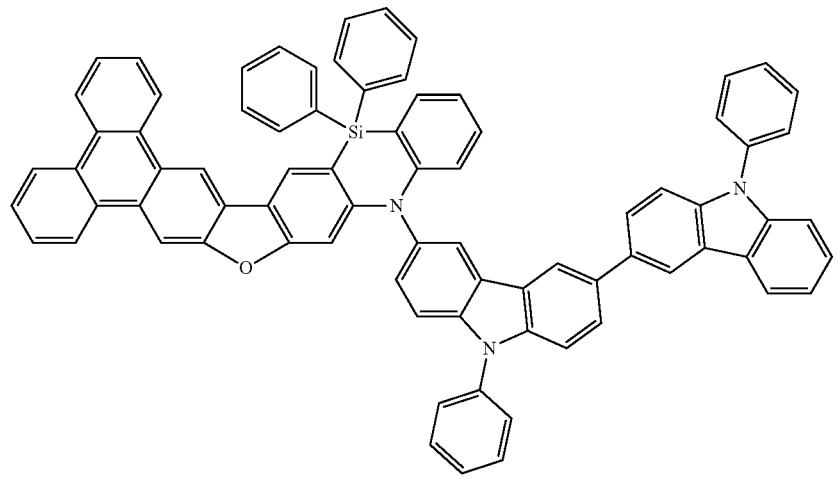
Compound 72
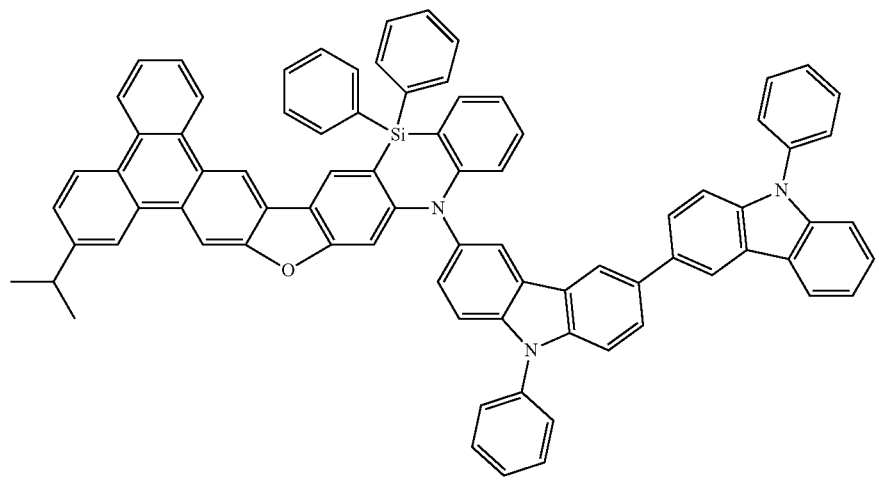
Compound 73
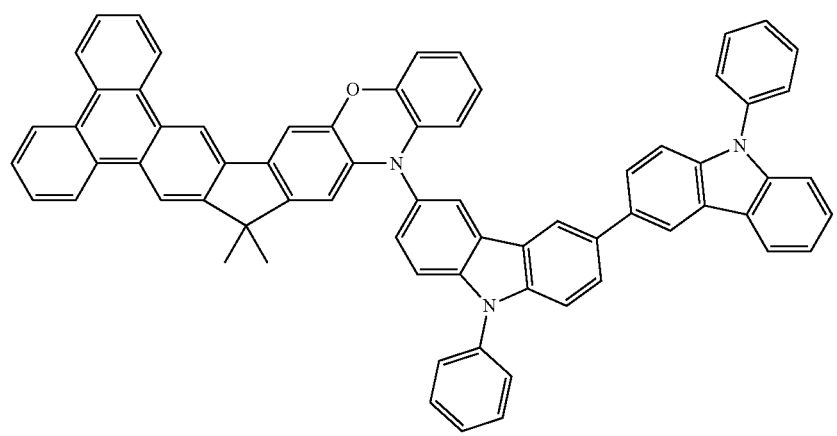

-continued
Compound 74
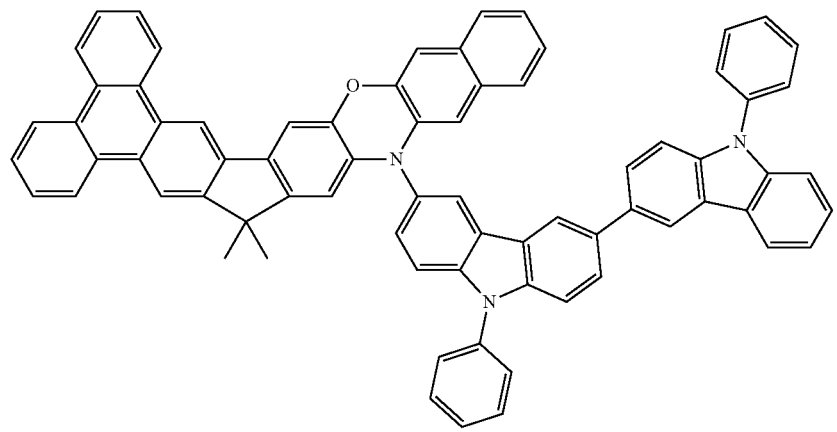
Compound 75
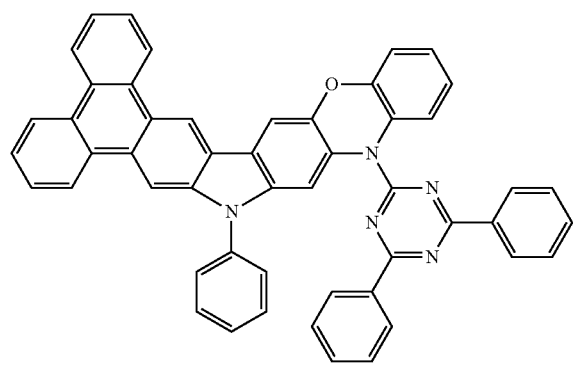
Compound 76
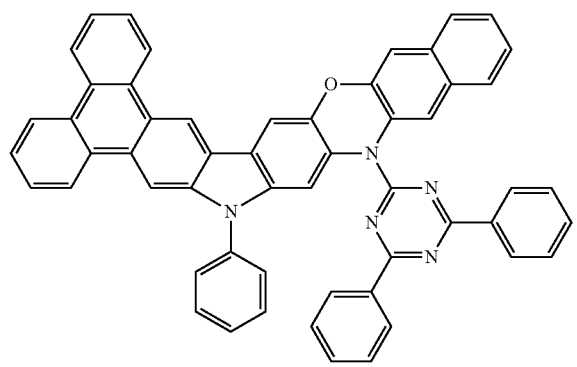
Compound 77
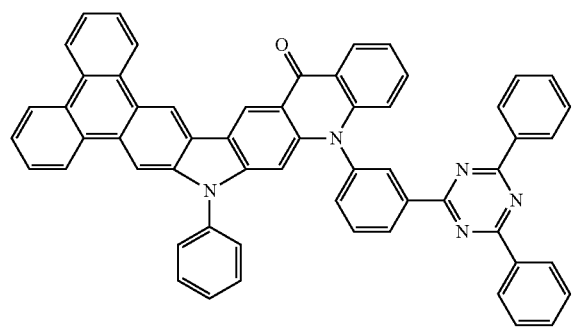
Compound 78
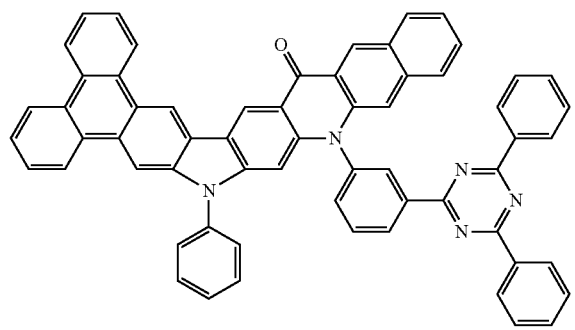
Compound 79
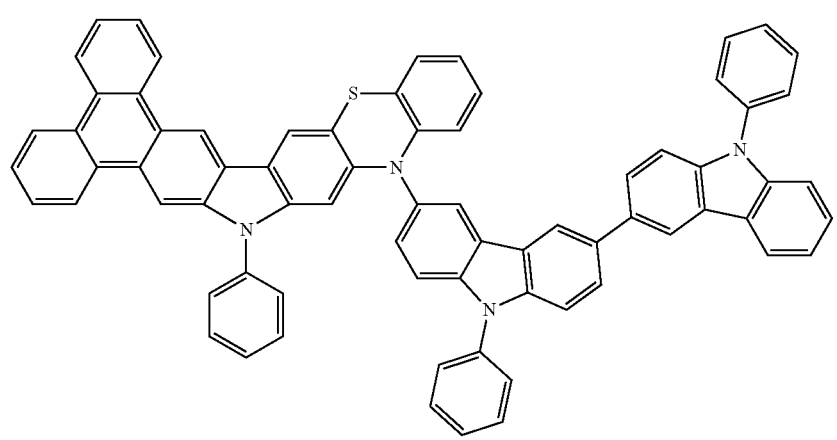

-continued
Compound 80
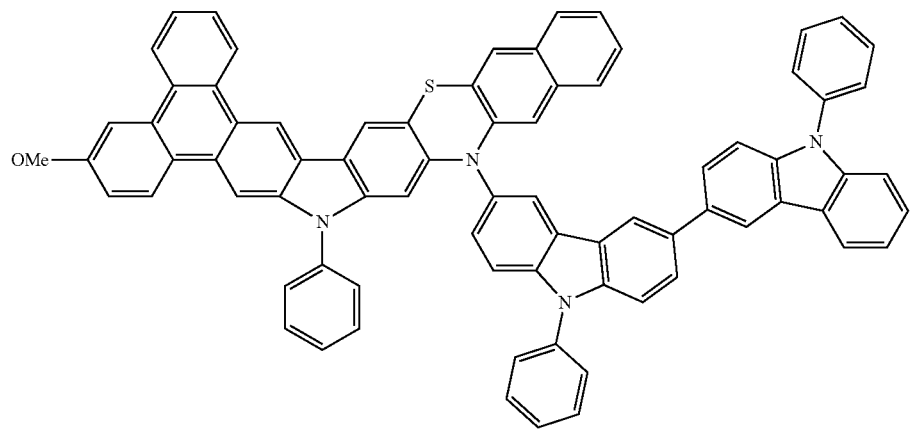
Compound 81
Compound 82
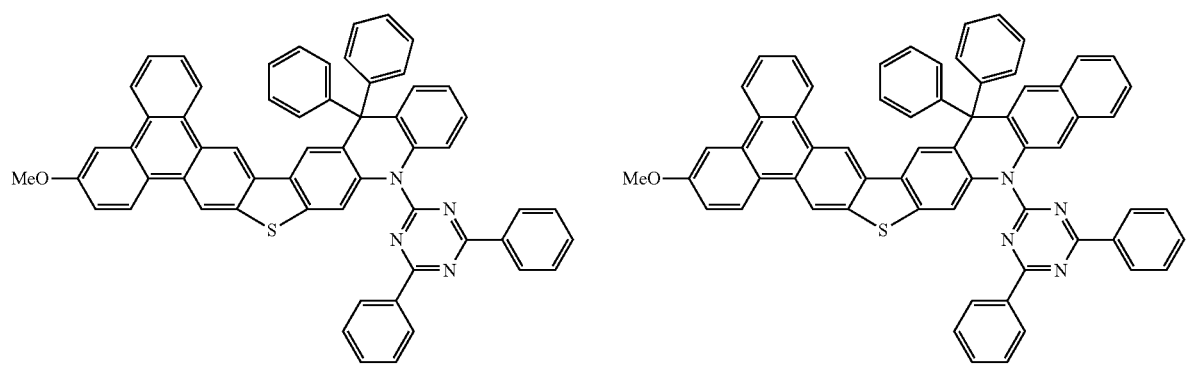
Compound 83
Compound 84
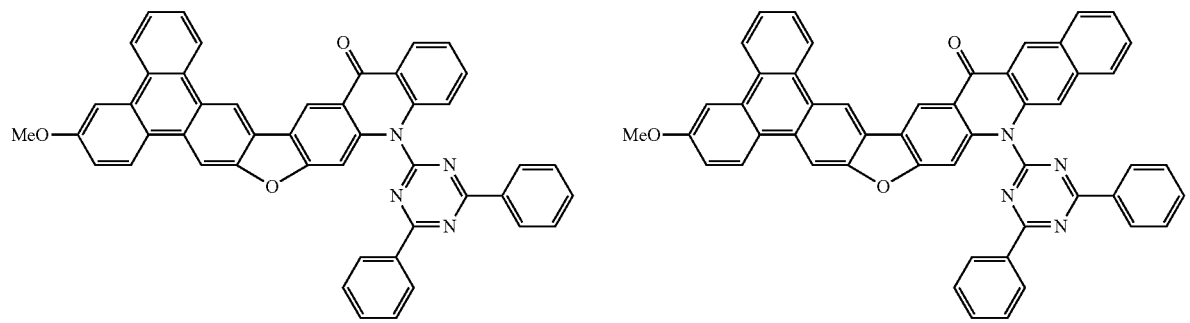
Compound 85
Compound 86
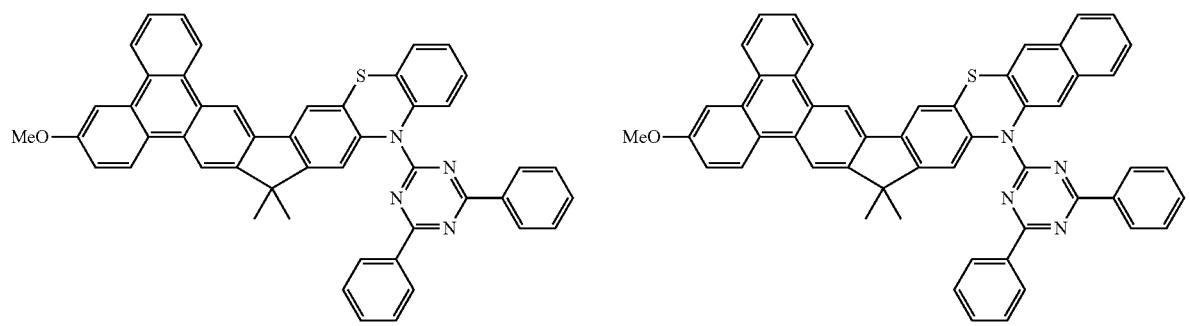

-continued
Compound 87
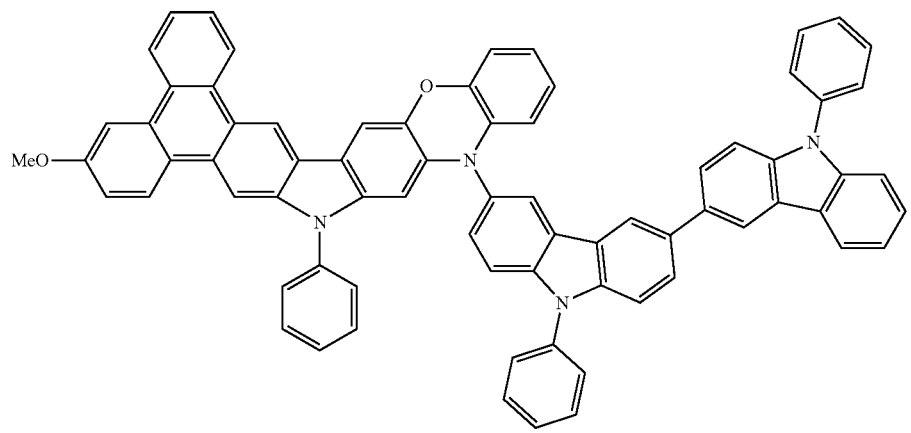
Compound 88
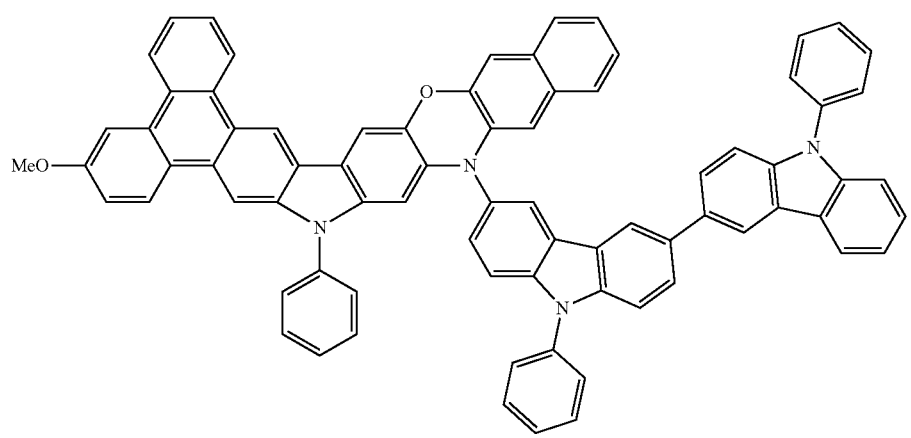
Compound 89
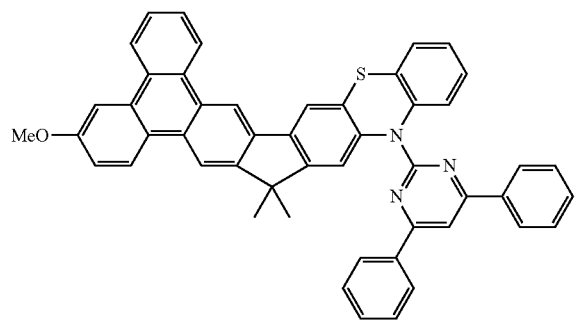
Compound 90
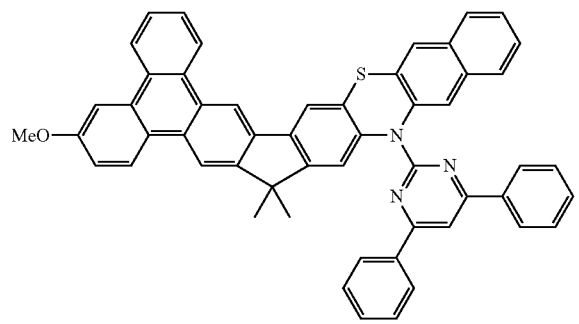
Compound 91
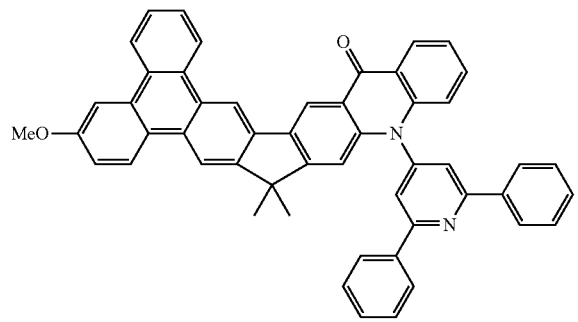
Compound 92
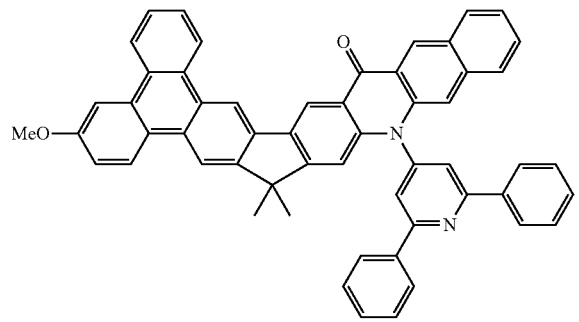

-continued
Compound 93
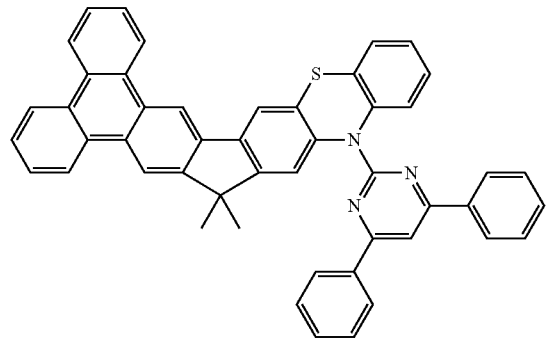
Compound 94
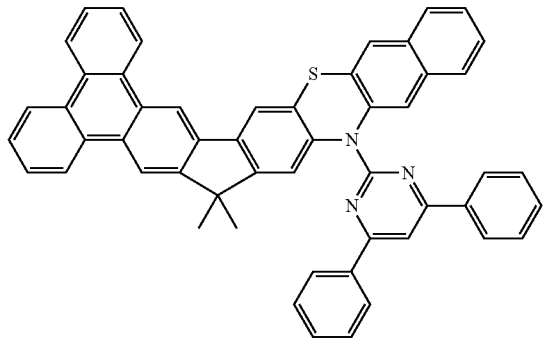
Compound 95
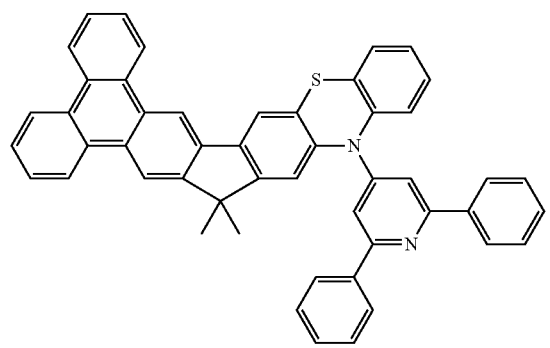
Compound 96
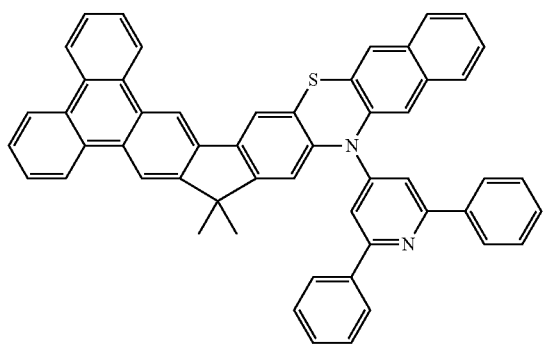
Compound 97
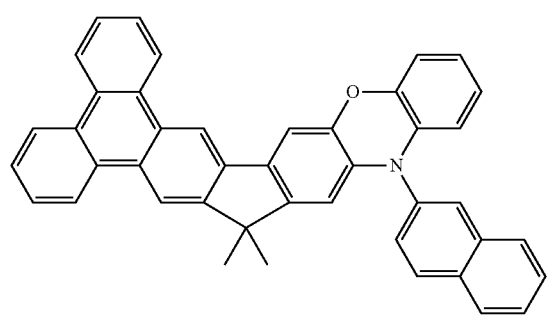
Compound 98
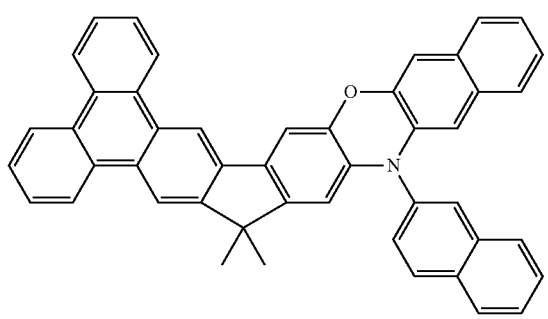
Compound 99
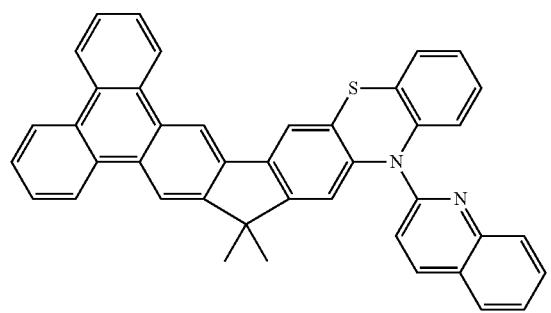
Compound 100
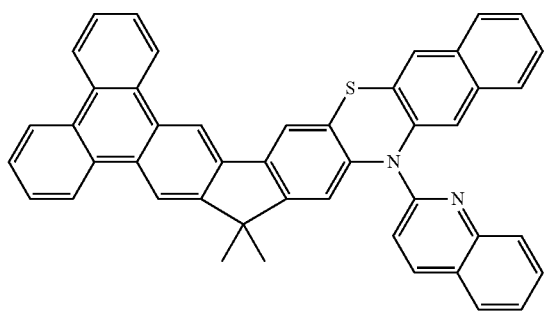

-continued
Compound 101
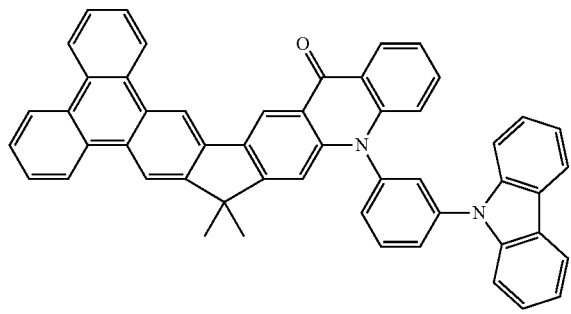
Compound 102
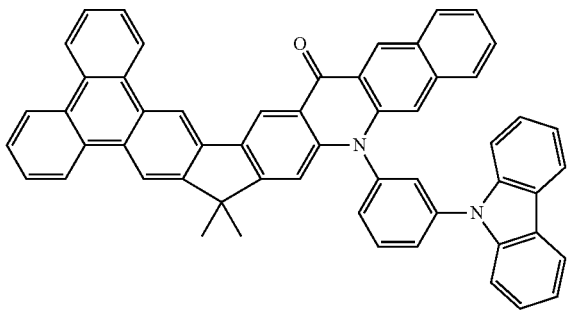
Compound 103
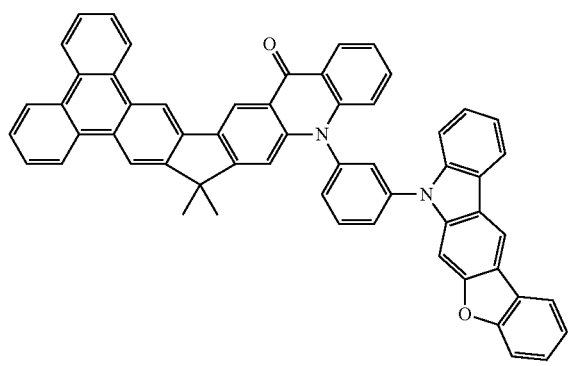
Compound 104
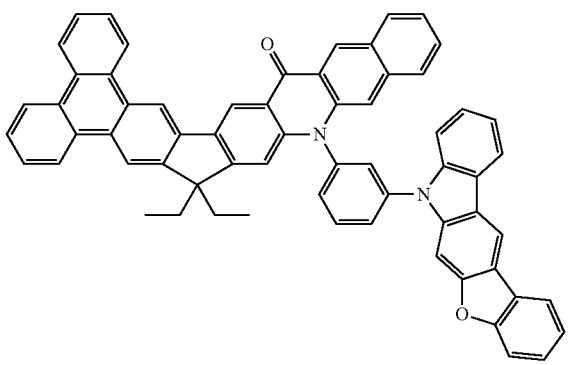
Compound 105
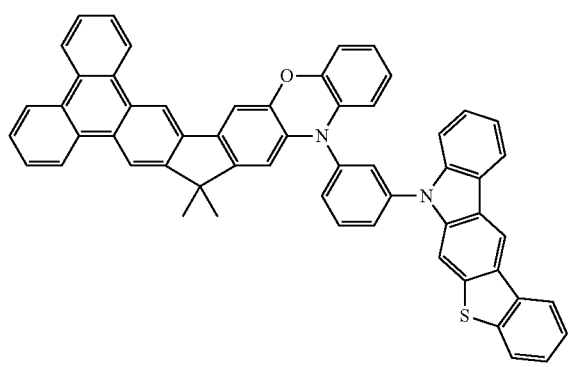
Compound 106
Compound 107
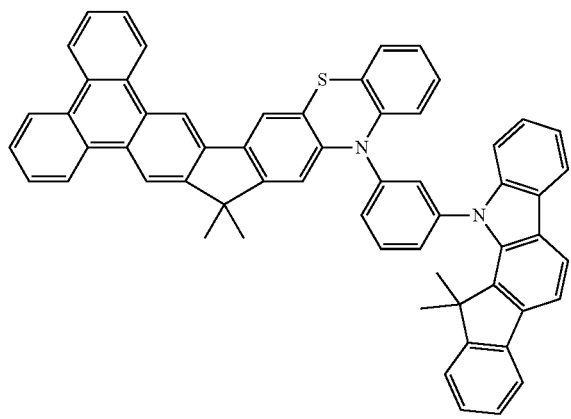
Compound 108
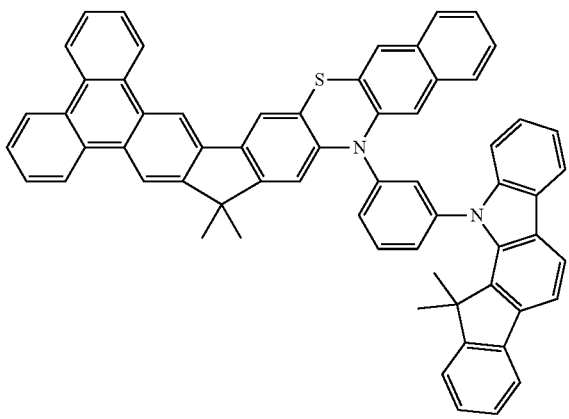

-continued
Compound 109
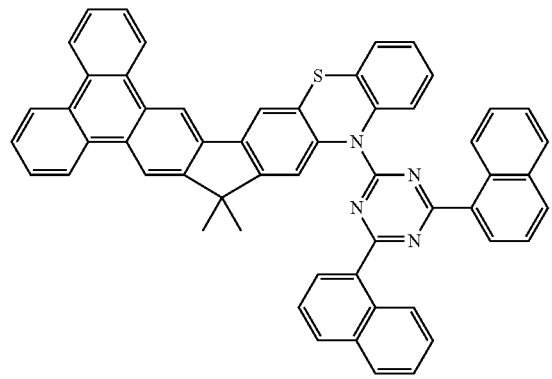
Compound 110
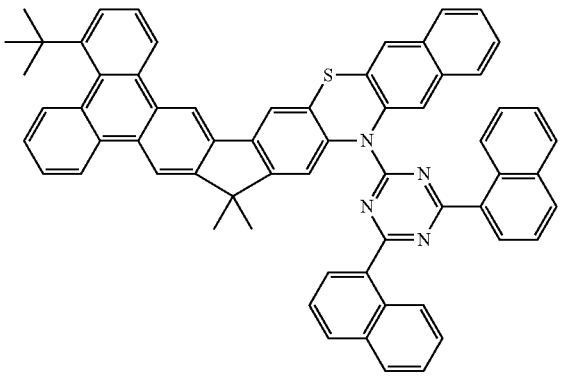
Compound 111
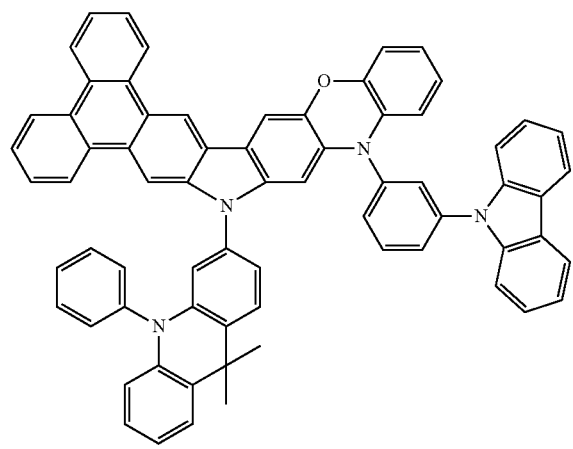
Compound 112
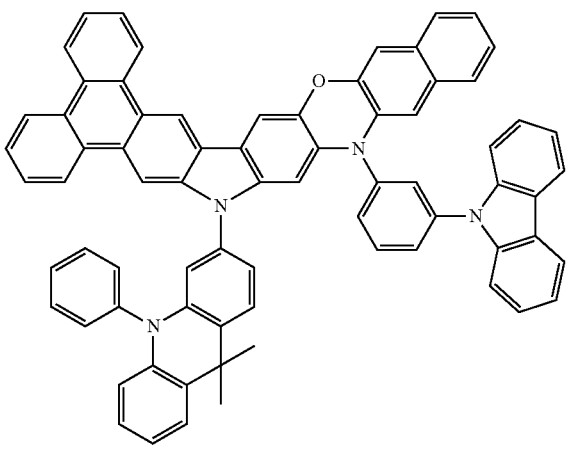
Compound 113
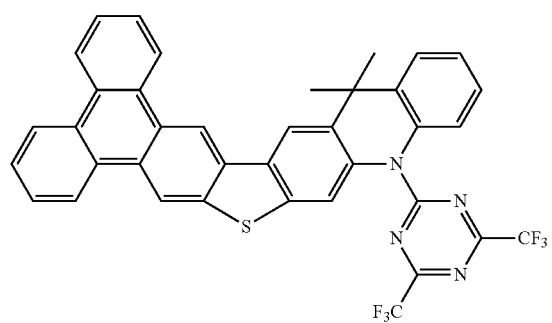
Compound 114
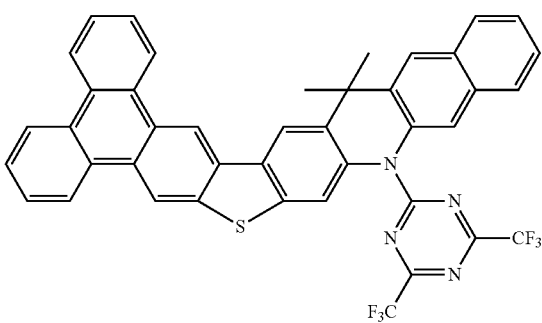
Compound 115
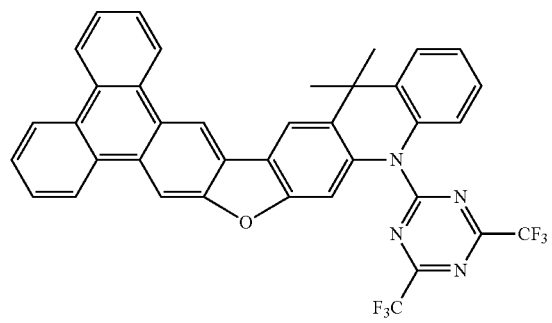
Compound 116
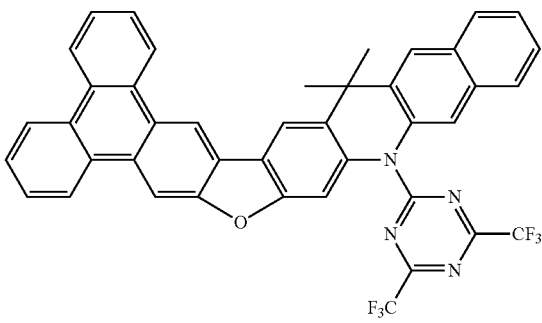

-continued
Compound 117
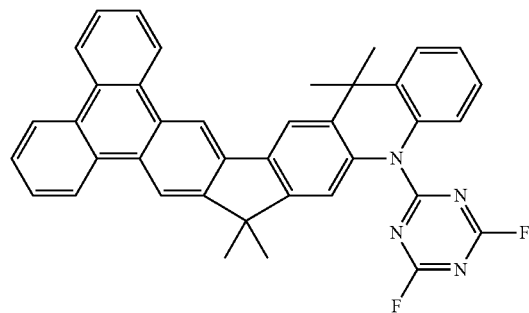
Compound 118
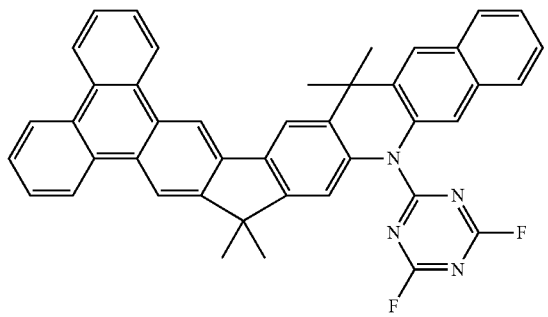
Compound 119
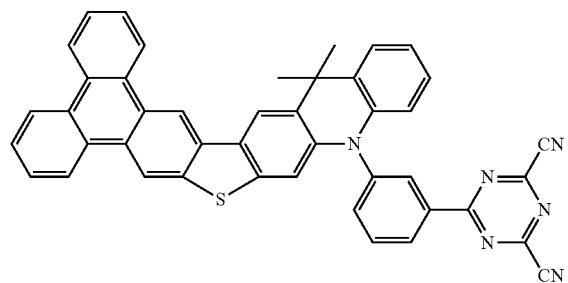
Compound 120
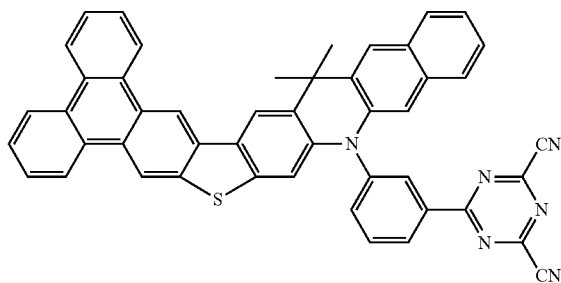
Compound 121
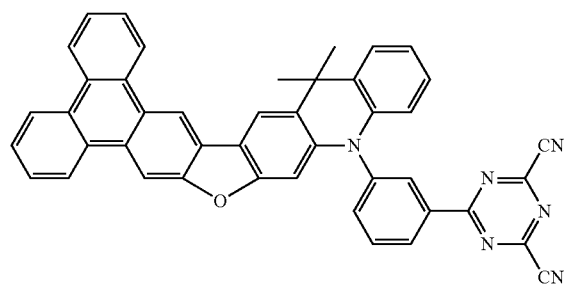
Compound 122
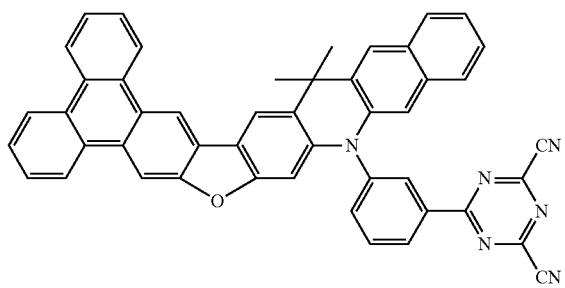
Compound 123
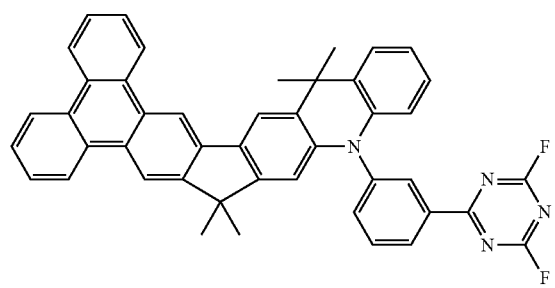
Compound 124
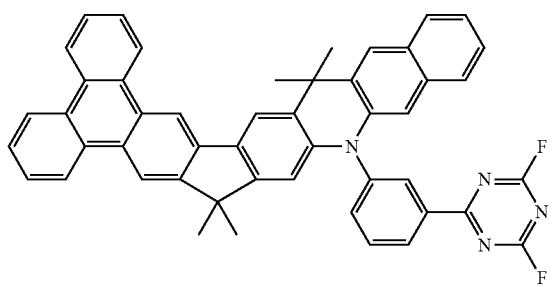

-continued
Compound 125
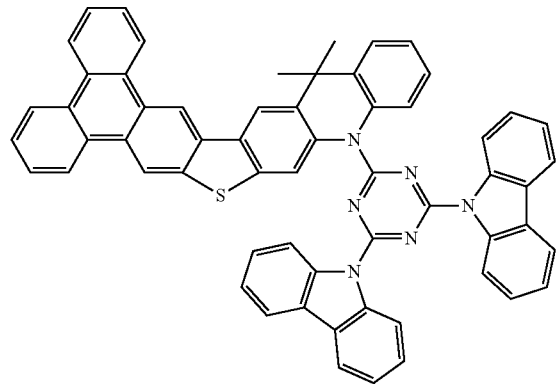
Compound 126
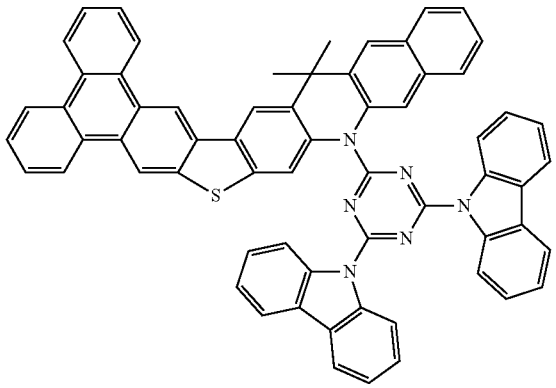
Compound 127
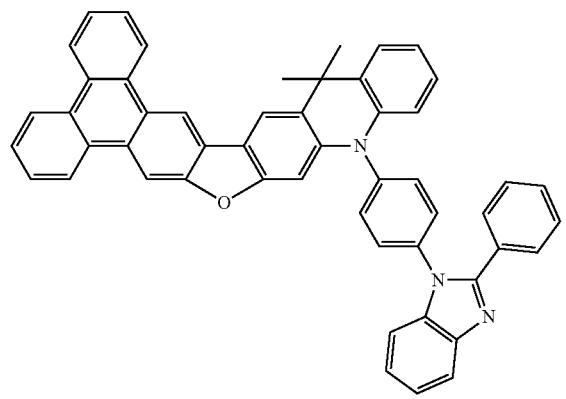
Compound 128
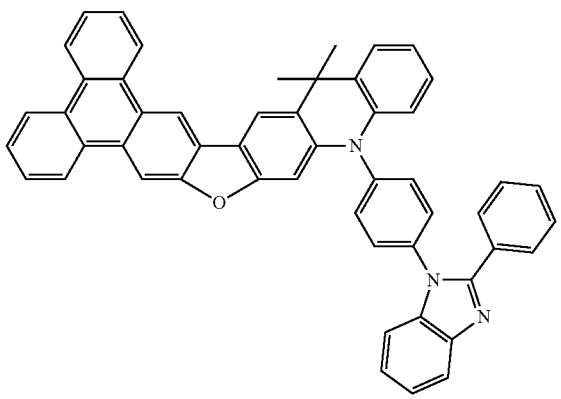
Compound 129
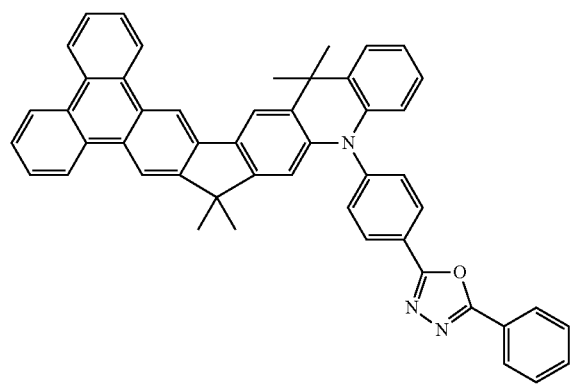
Compound 130
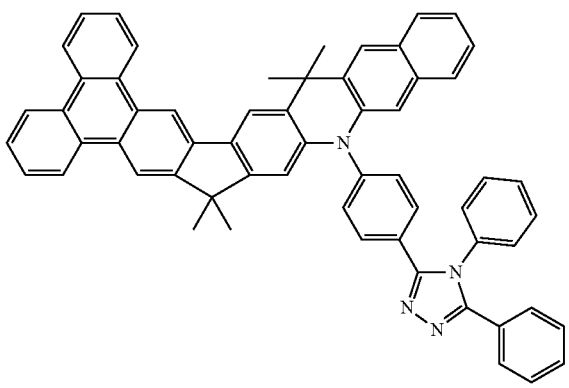
Compound 131
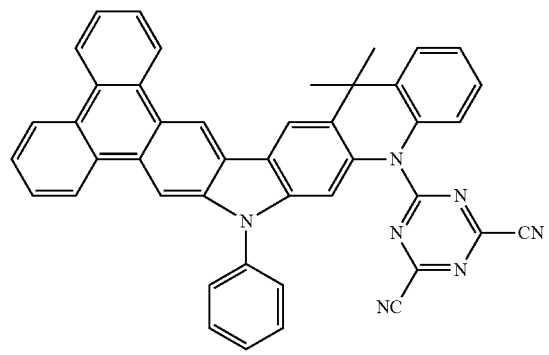
Compound 132
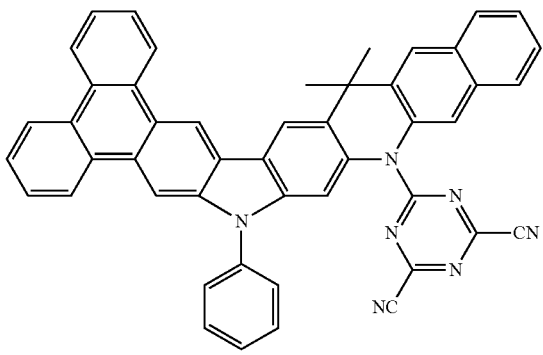

Compound 133
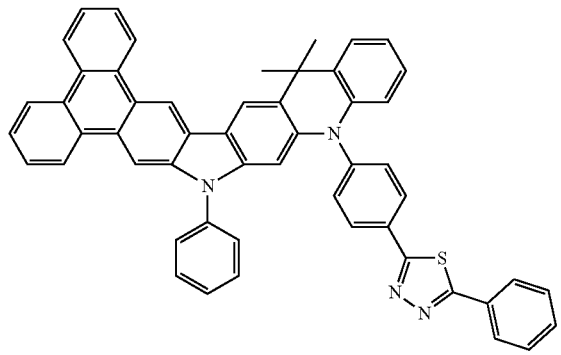
Compound 134
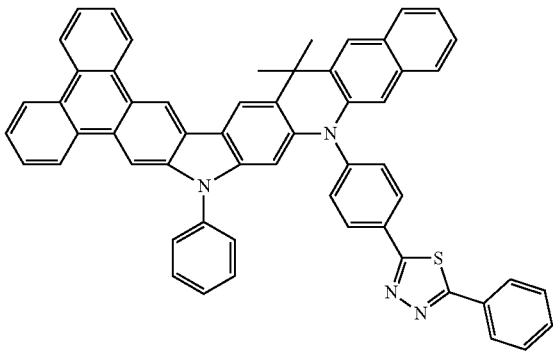
Compound 135
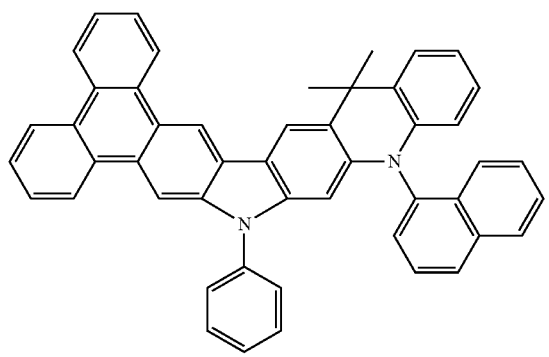
Compound 136
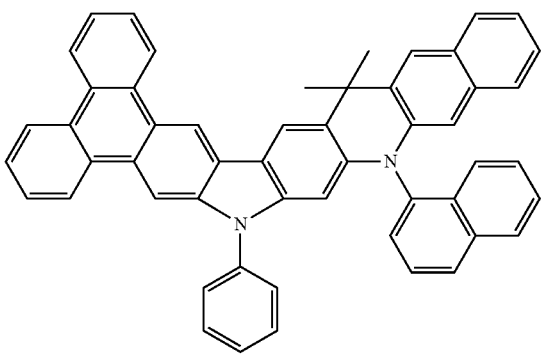
Compound 137
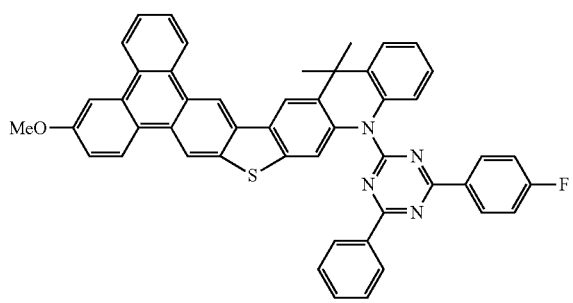
Compound 138
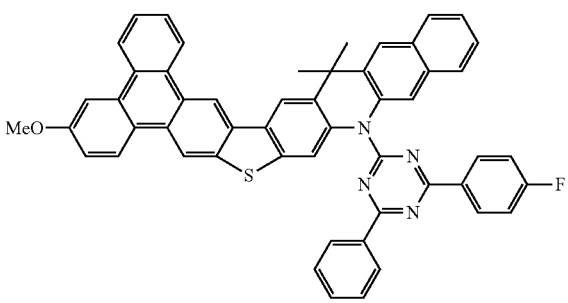
Compound 139
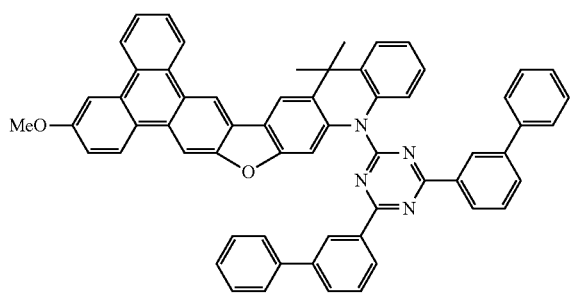
Compound 140
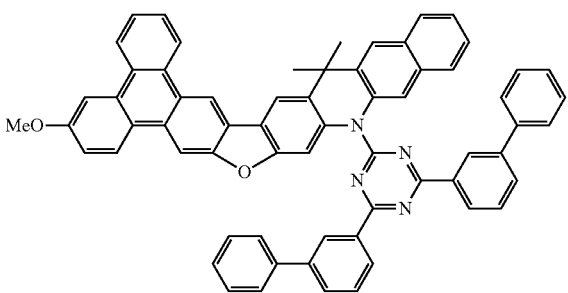

-continued
Compound 141
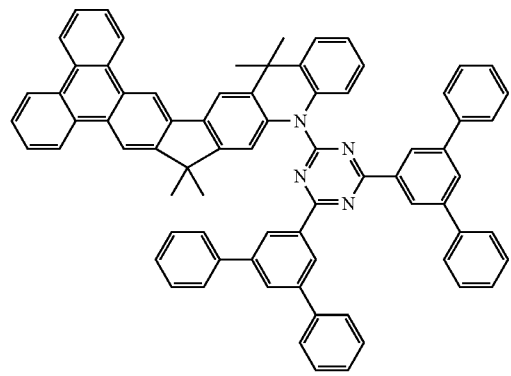
Compound 142
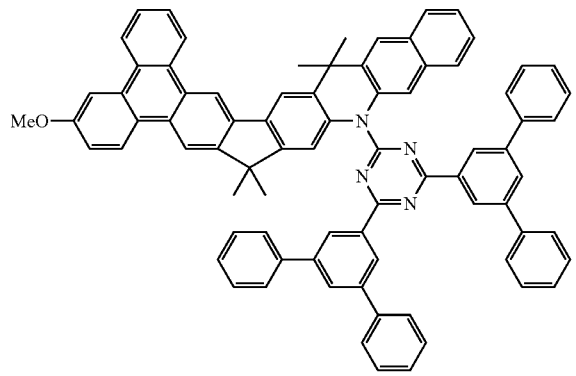
Compound 143
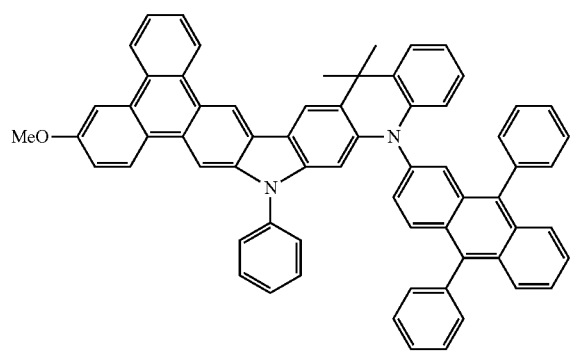
Compound 144
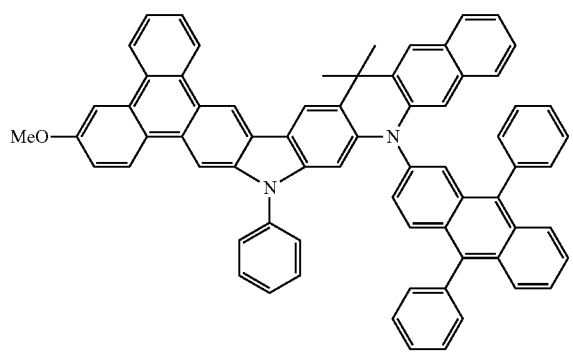
Compound 145
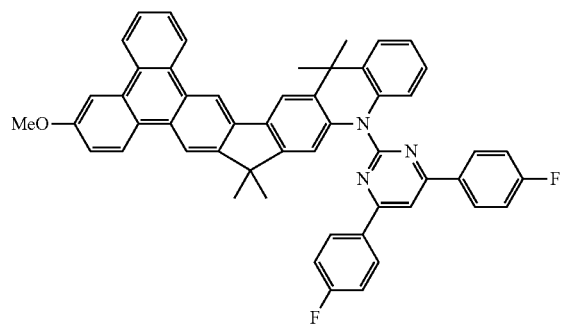
Compound 146
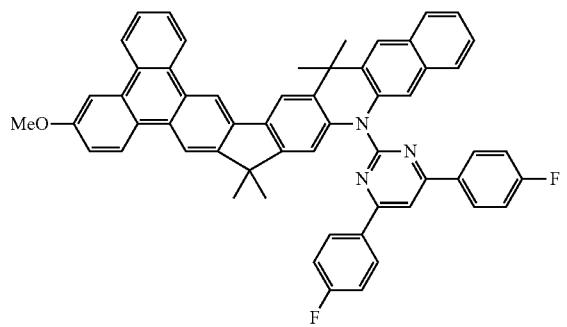
Compound 147
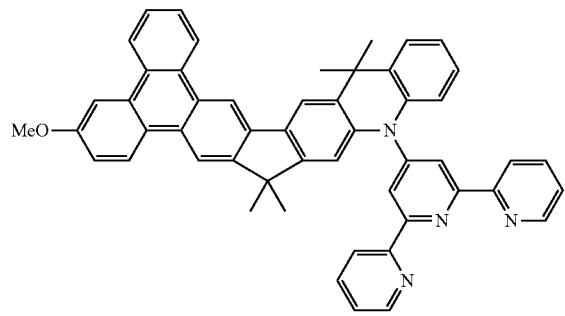
Compound 148
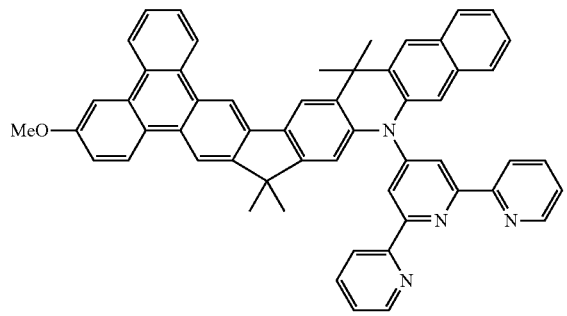

-continued
Compound 149
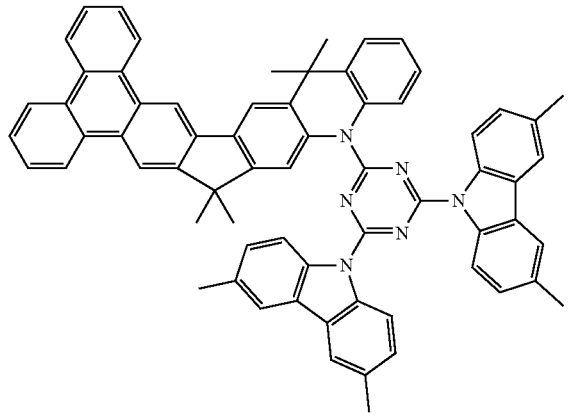
Compound 150
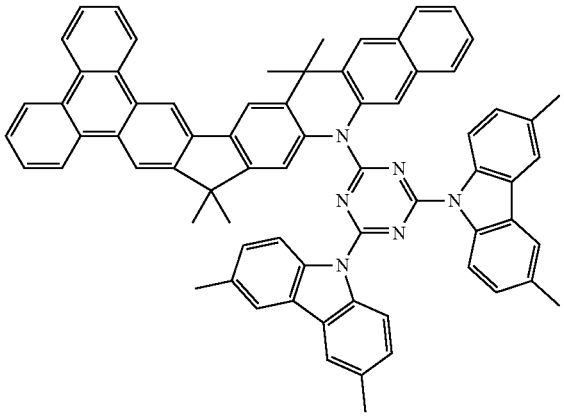
Compound 151
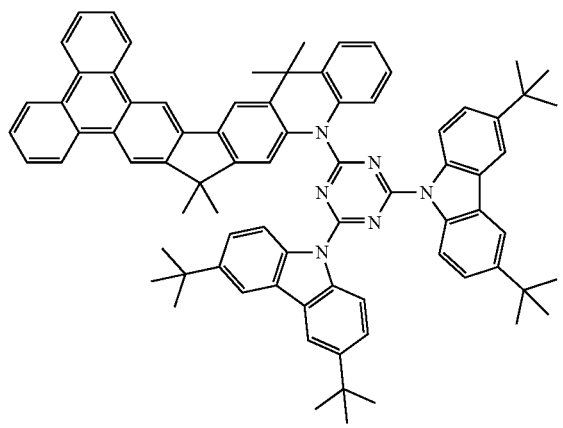
Compound 152
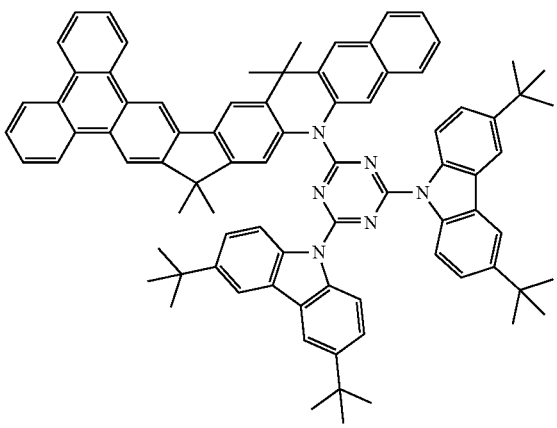
Compound 153
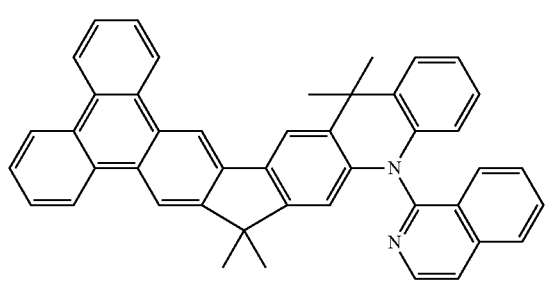
Compound 154
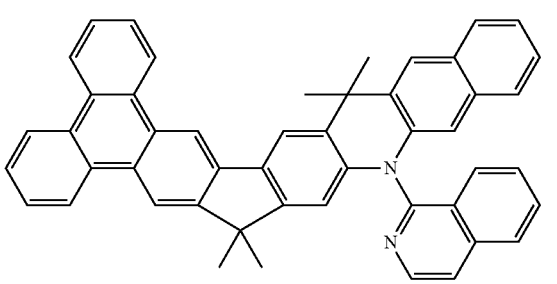
Compound 155
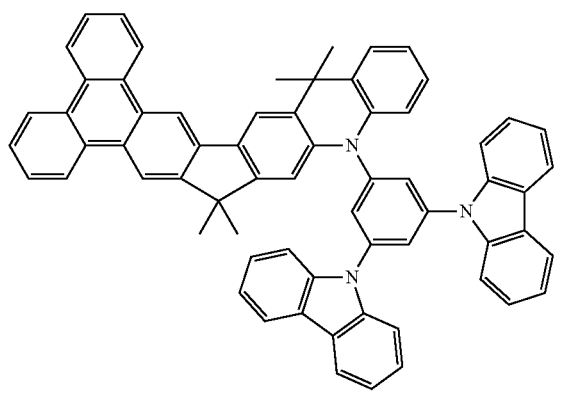
Compound 156
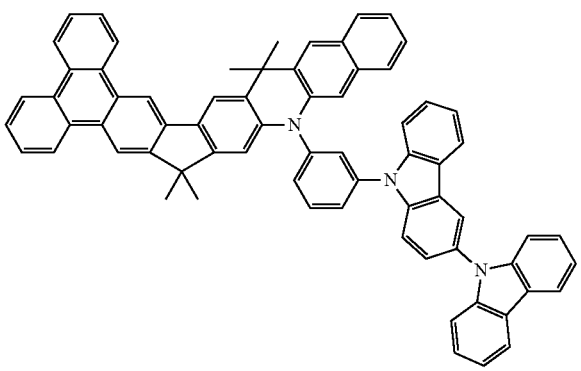

-continued
Compound 157
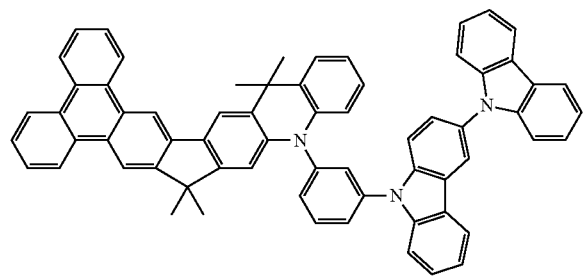
Compound 158
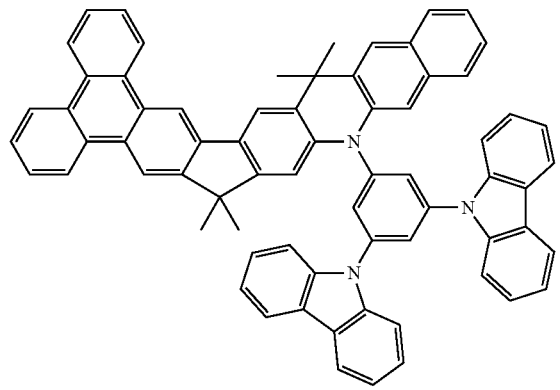
Compound 159
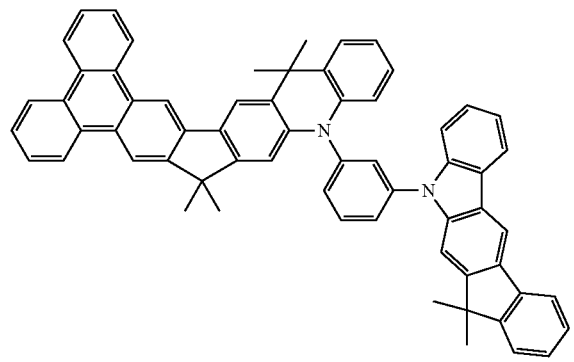
Compound 160
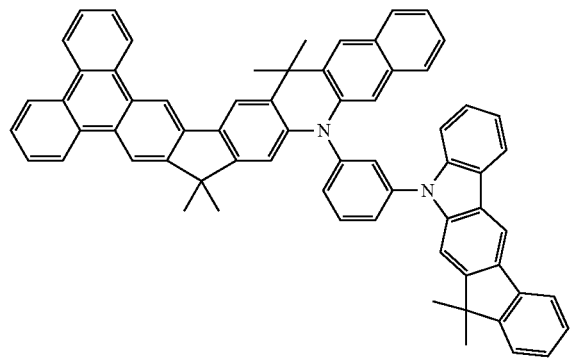
Compound 161
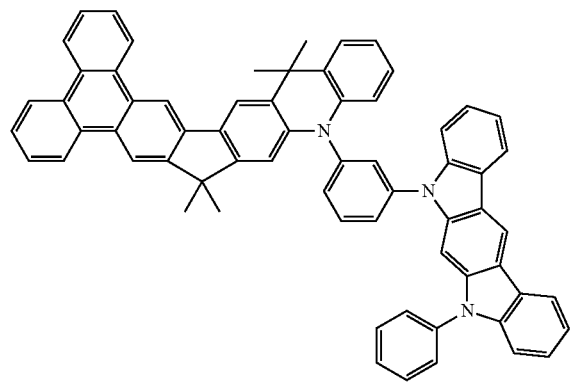
Compound 162
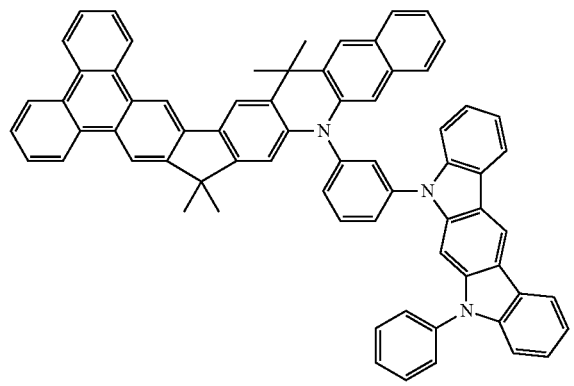
Compound 163
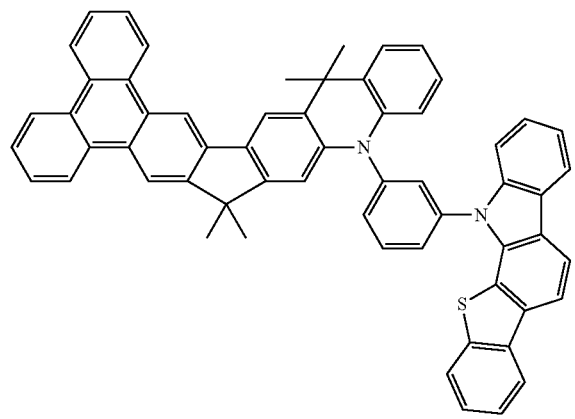
Compound 164
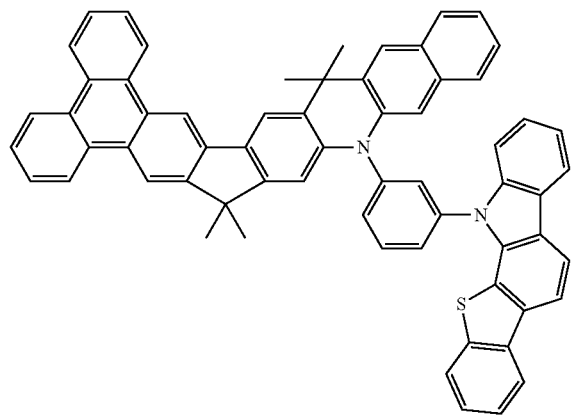

-continued
Compound 165
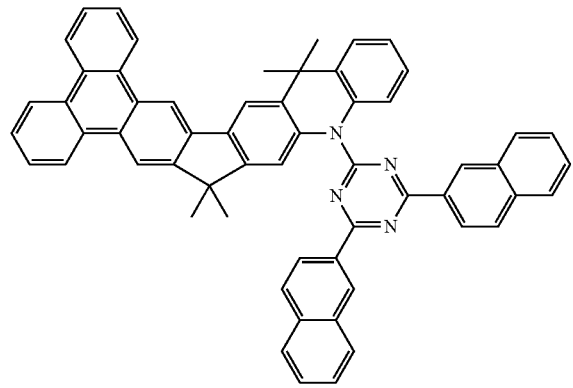
Compound 166
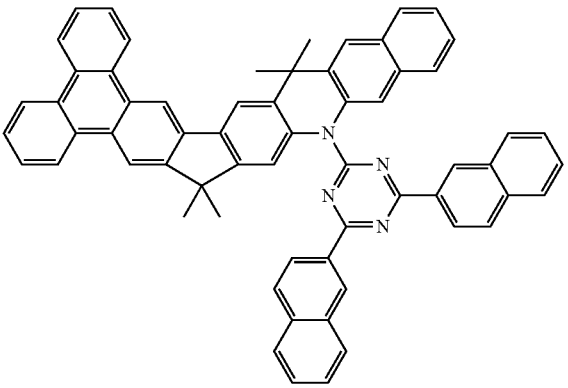
Compound 167
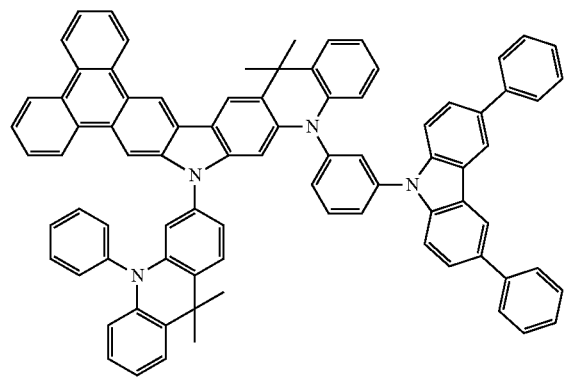
Compound 168
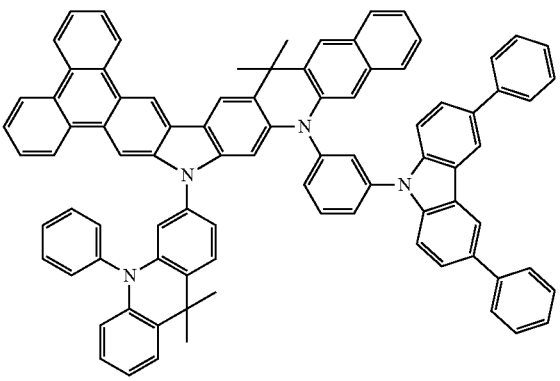
Compound 169
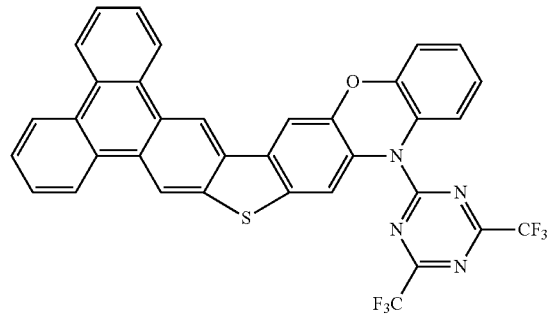
Compound 170
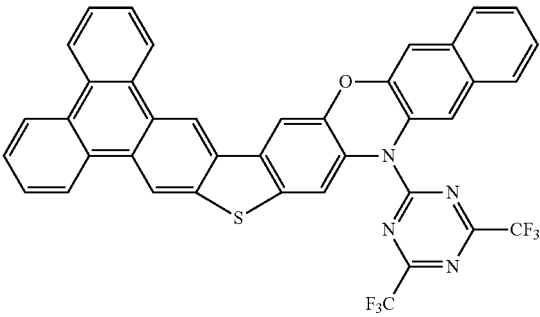
Compound 171
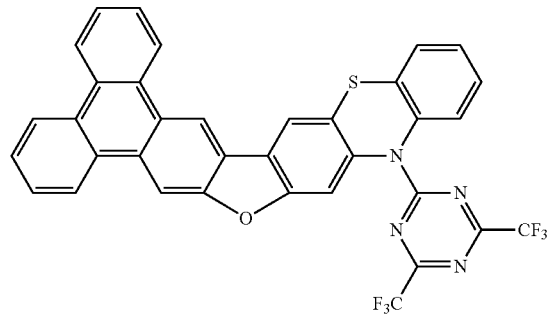
Compound 172
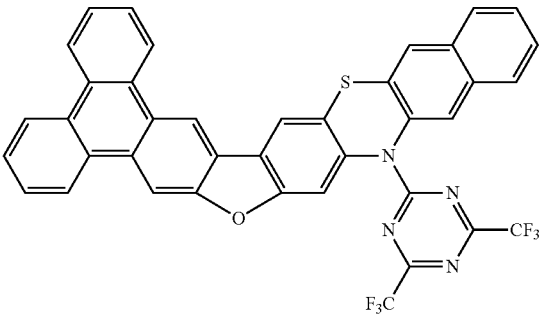

-continued
Compound 173
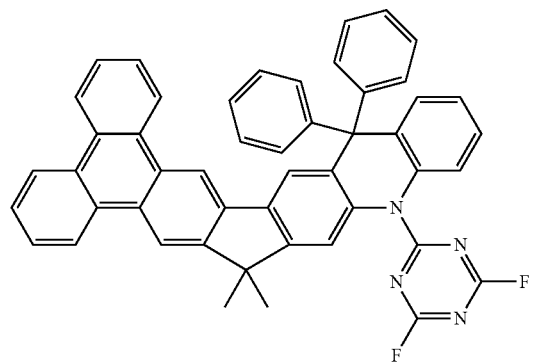
Compound 174
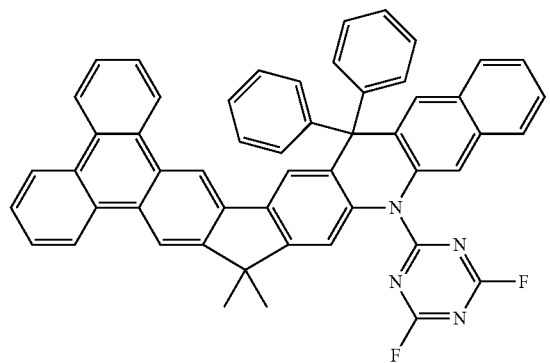
Compound 175
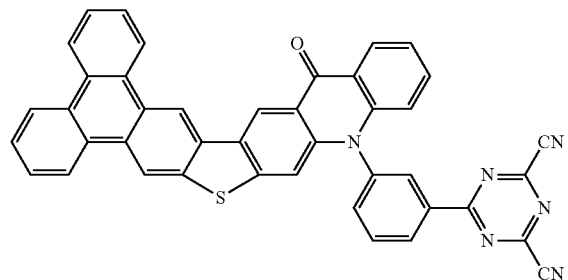
Compound 176
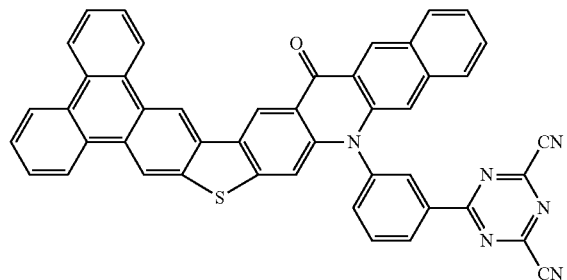
Compound 177
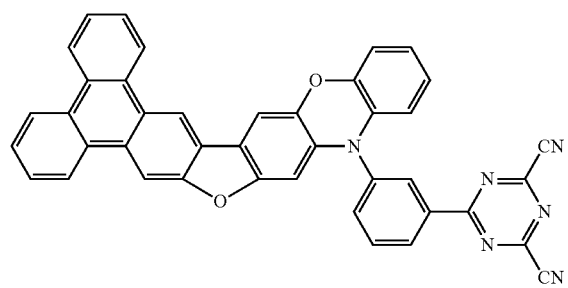
Compound 178
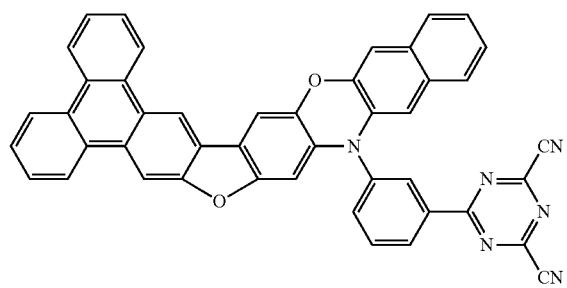
Compound 179
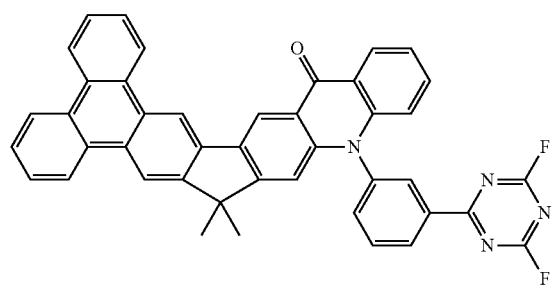
Compound 180
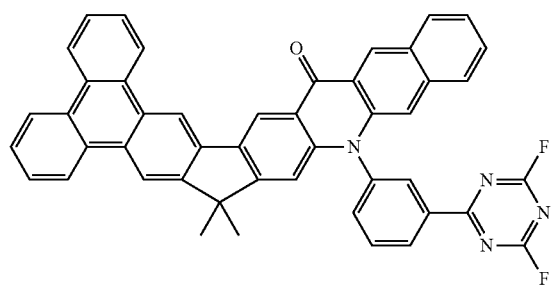

Compound 181
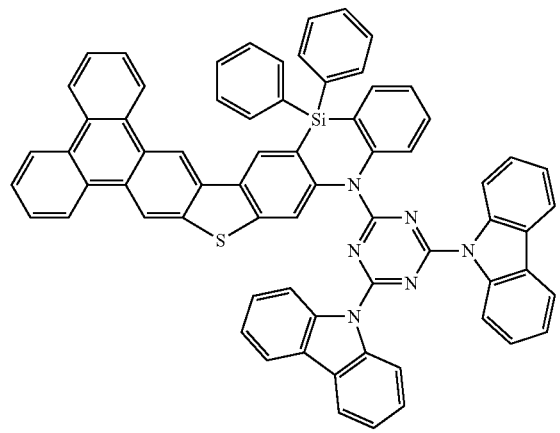
Compound 182
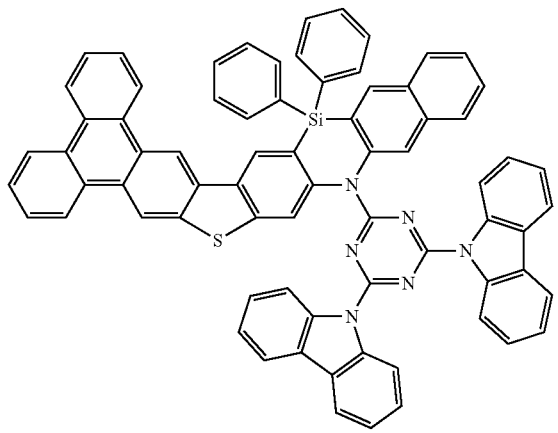
Compound 183
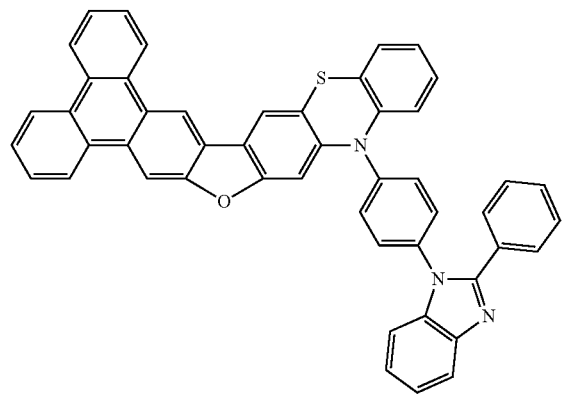
Compound 184
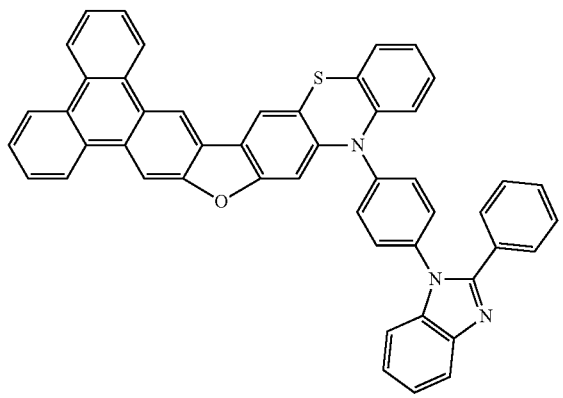
Compound 185
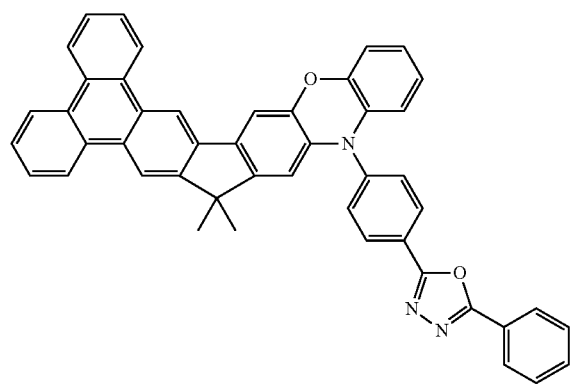
Compound 186
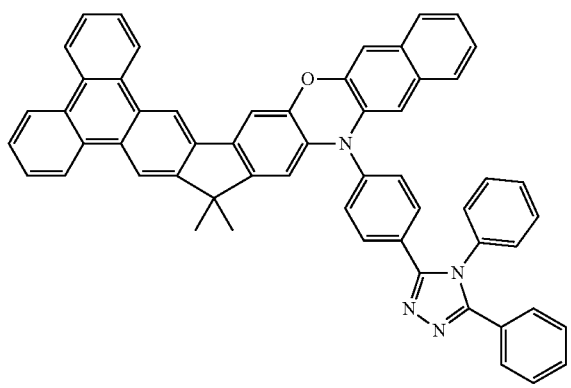
Compound 187
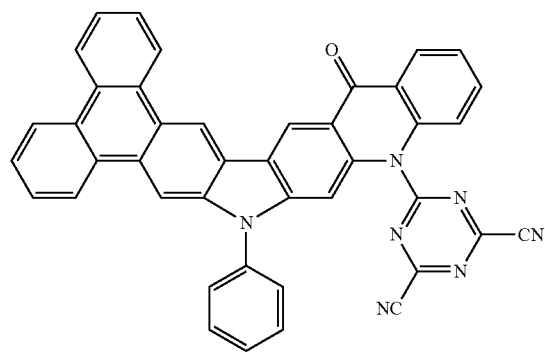
Compound 188
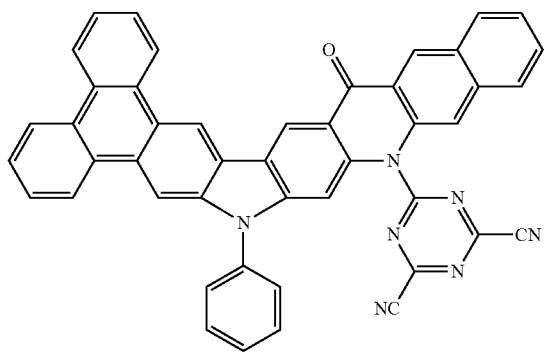

-continued
Compound 189
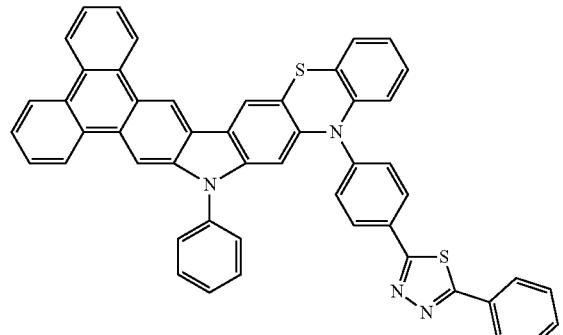
Compound 190
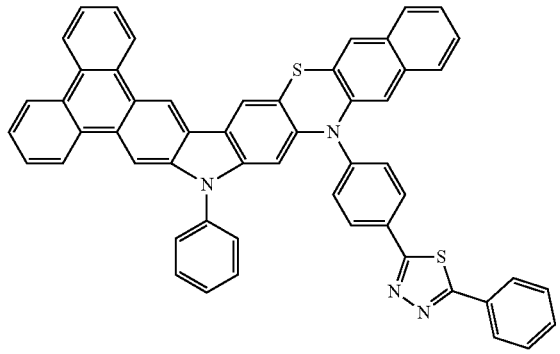
Compound 191
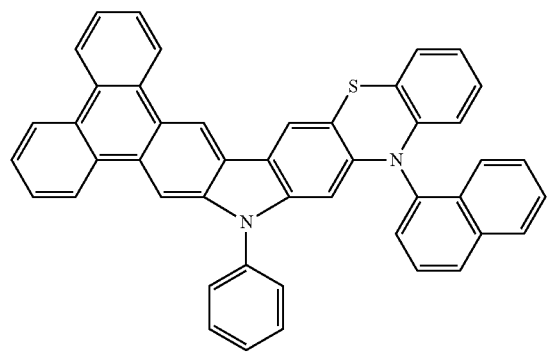
Compound 192
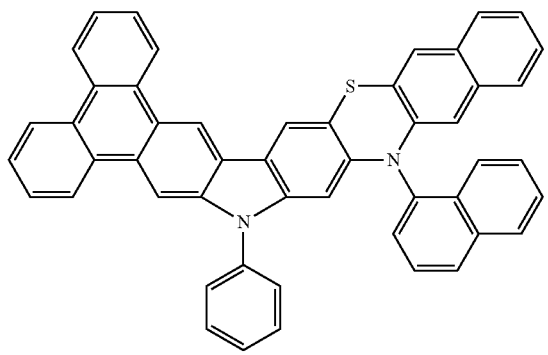
Compound 193
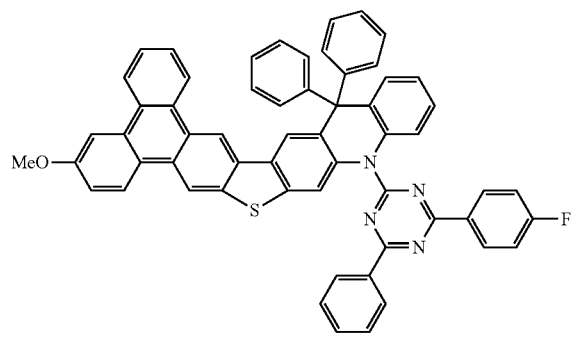
Compound 194
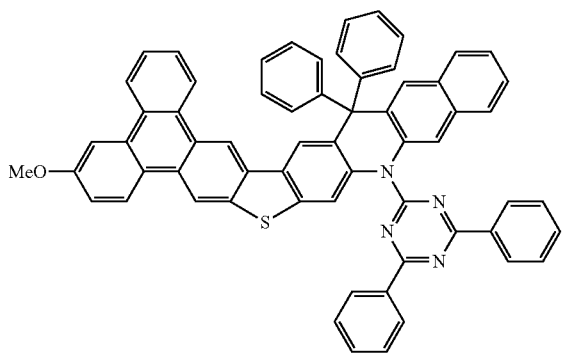
Compound 195
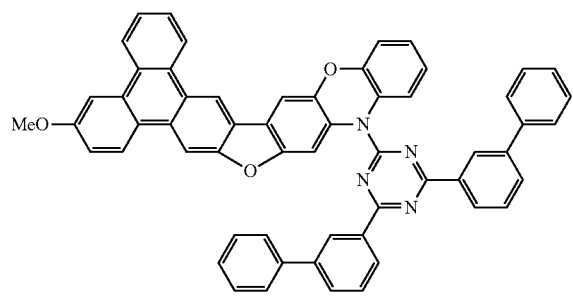
Compound 196
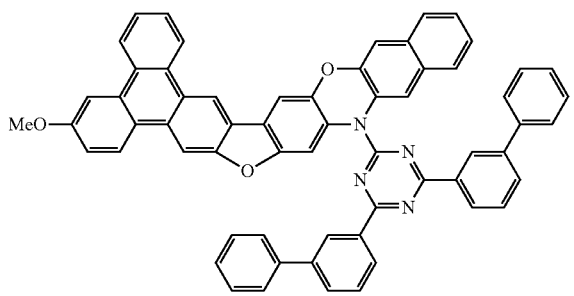

-continued
Compound 197
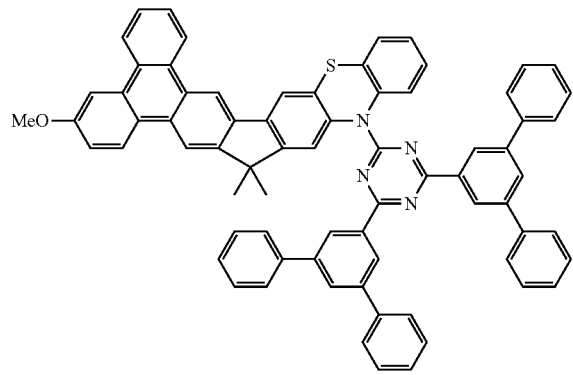
Compound 198
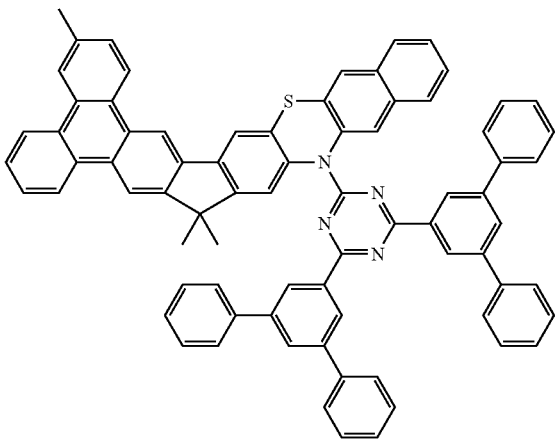
Compound 199
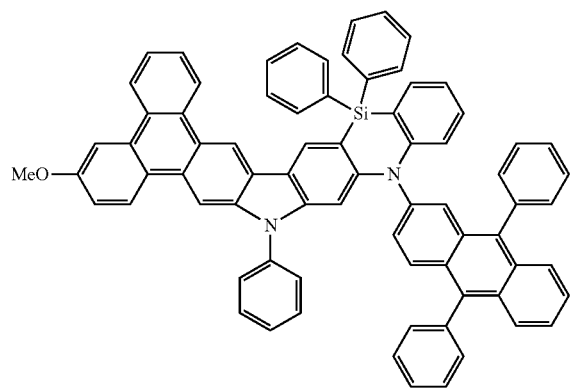
Compound 200
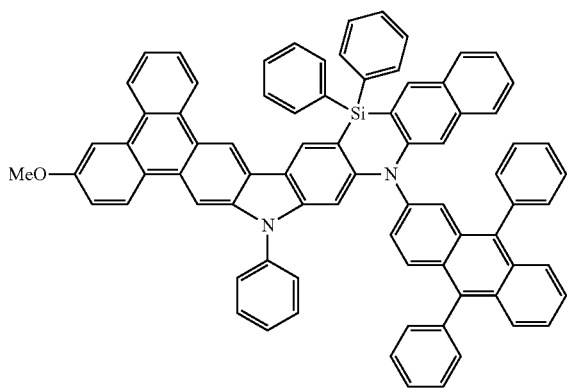
Compound 201
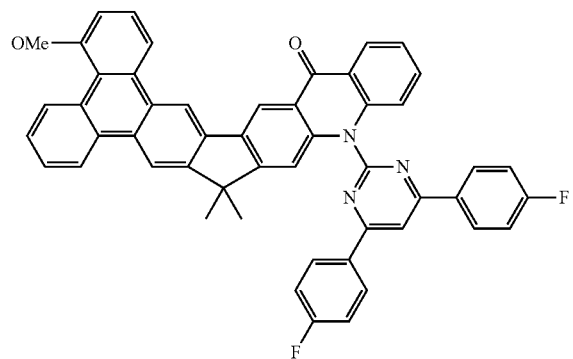
Compound 202
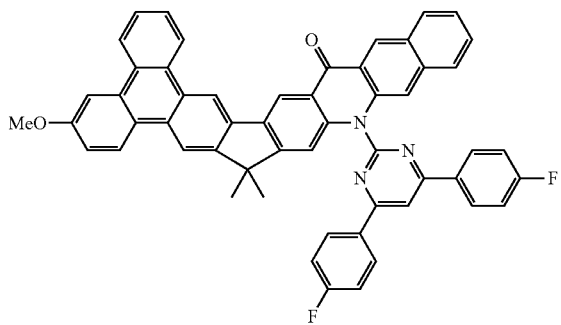
Compound 203
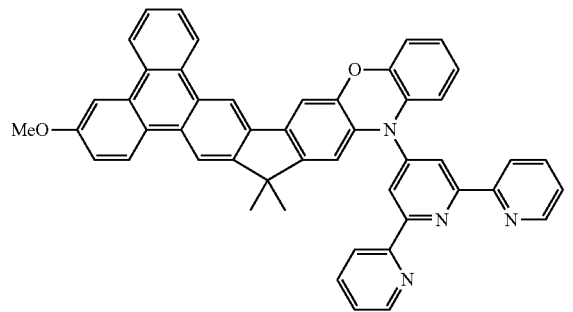
Compound 204
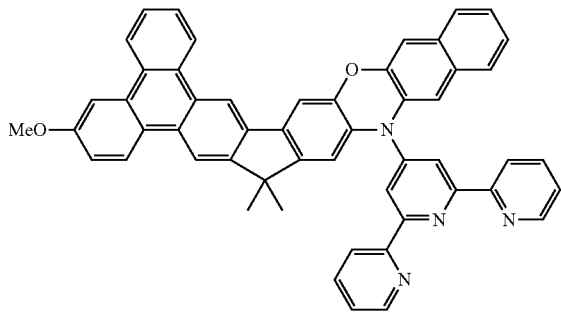

-continued
Compound 205
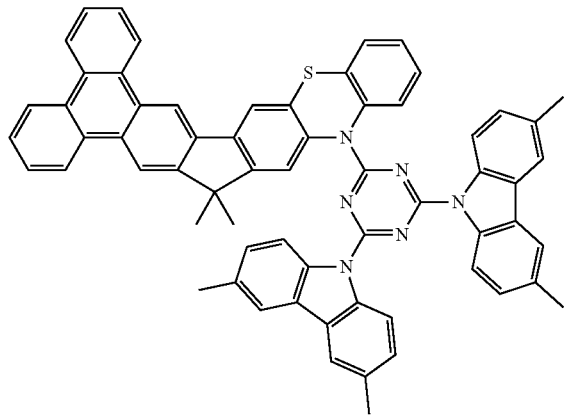
Compound 206
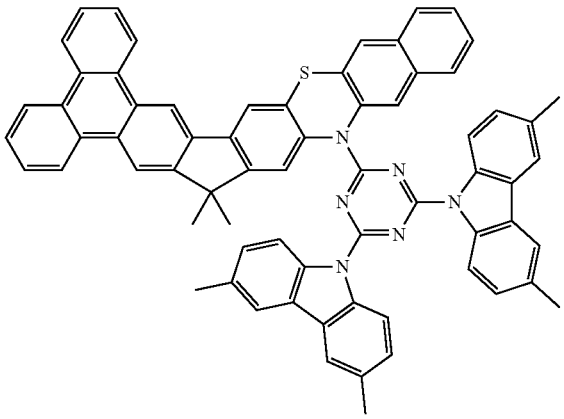
Compound 207
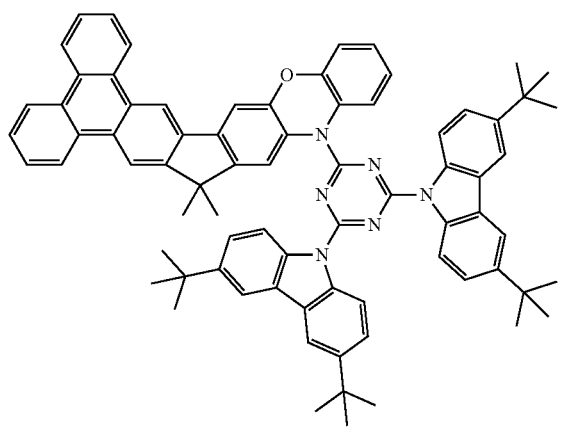
Compound 208
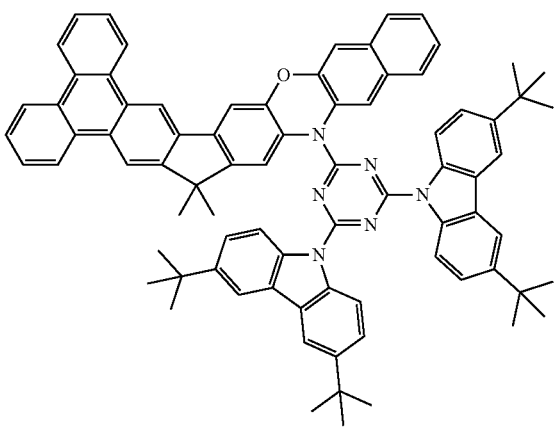
Compound 209
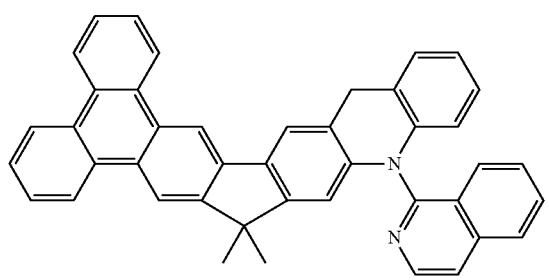
Compound 110
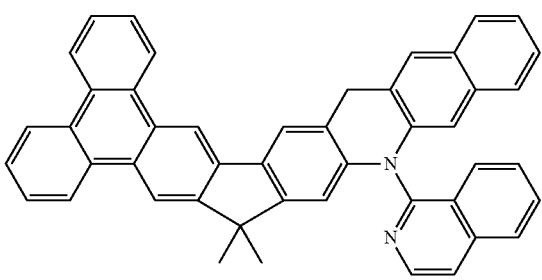
Compound 211
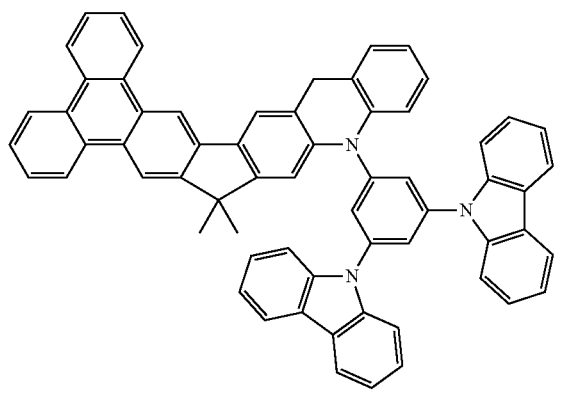
Compound 212
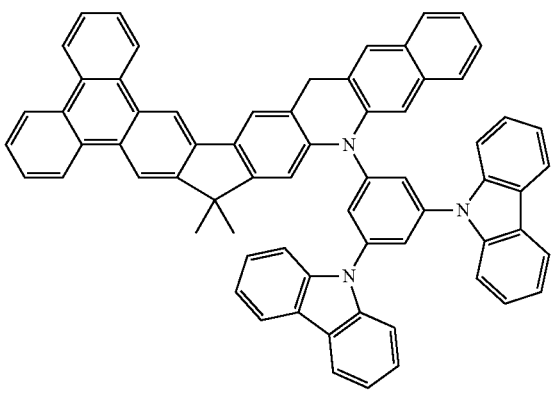

-continued
Compound 213
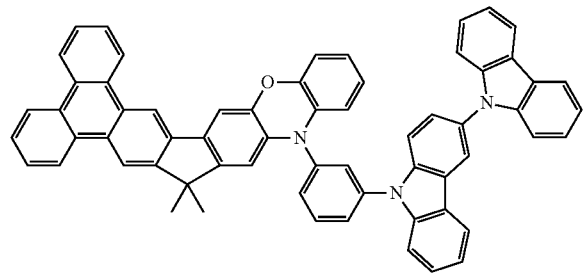
Compound 214
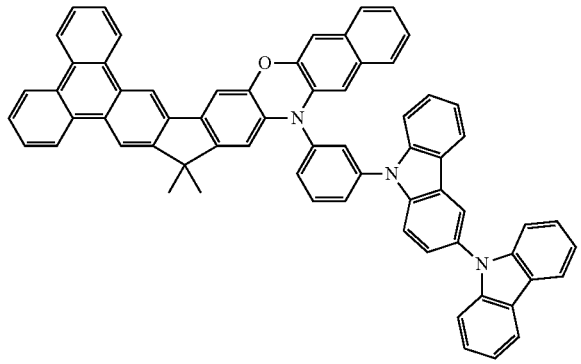
Compound 215
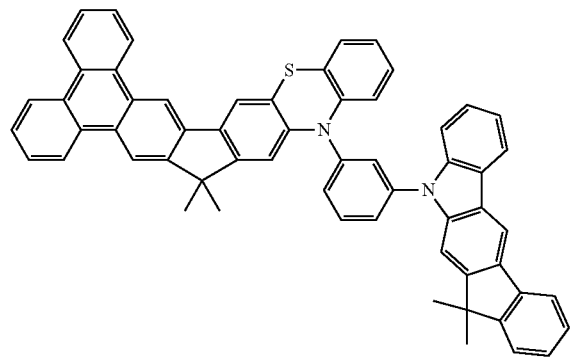
Compound 216
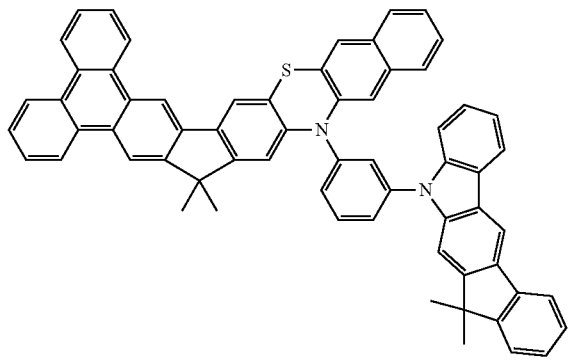
Compound 217
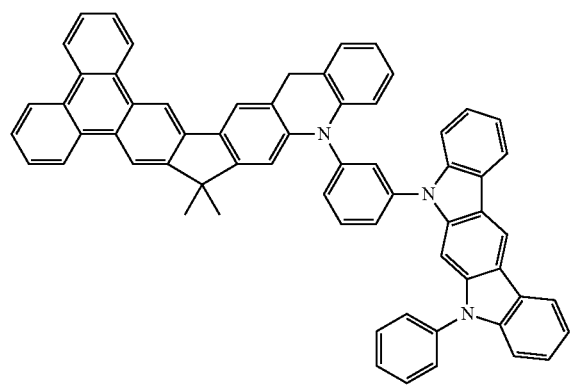
Compound 218
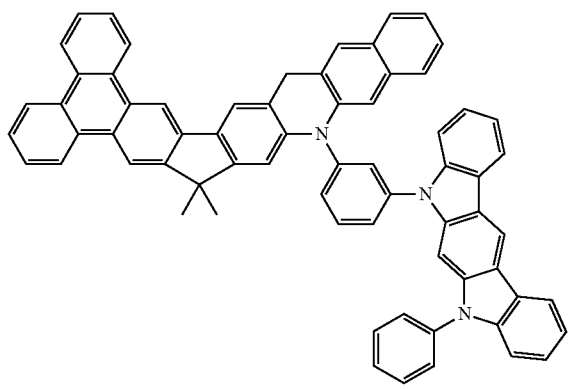
Compound 219
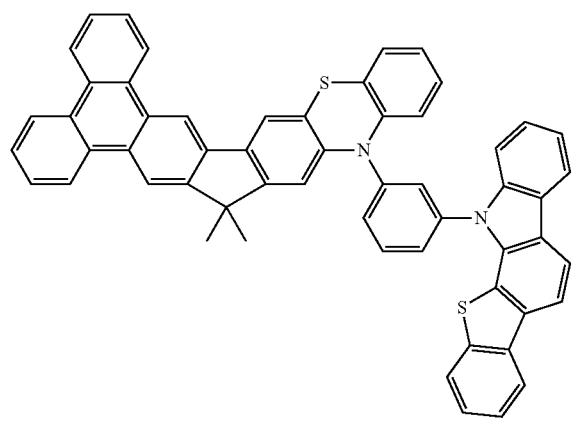
Compound 220
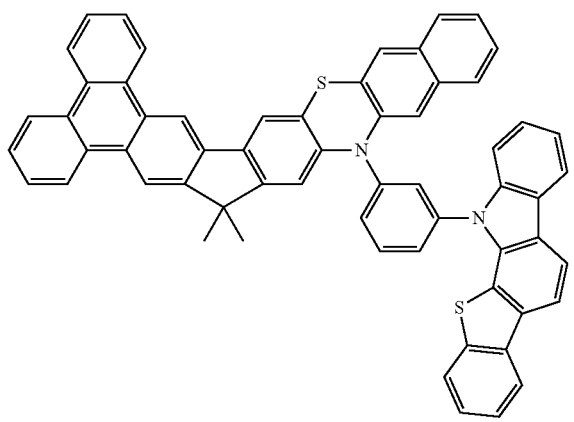

-continued
Compound 221
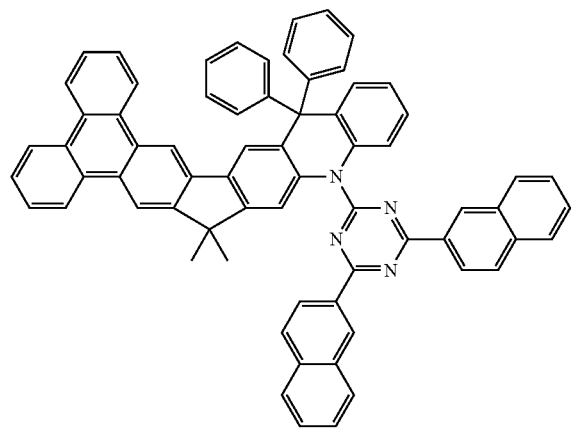
Compound 222
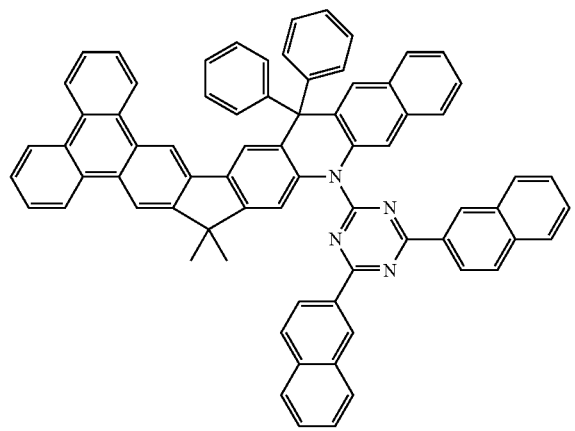
Compound 223
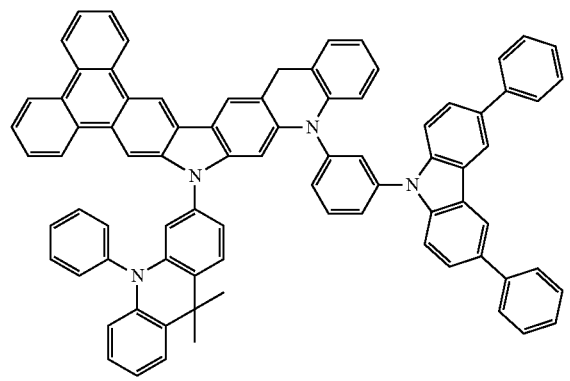
Compound 224
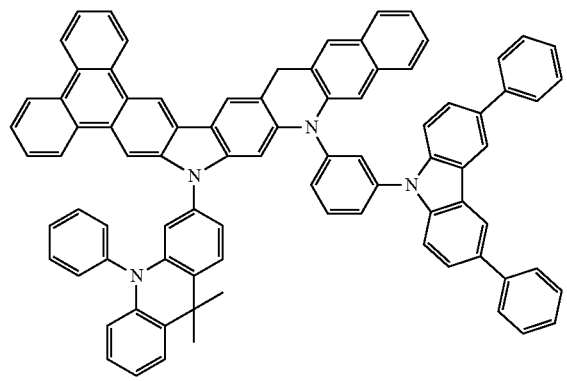
and
Compound 225
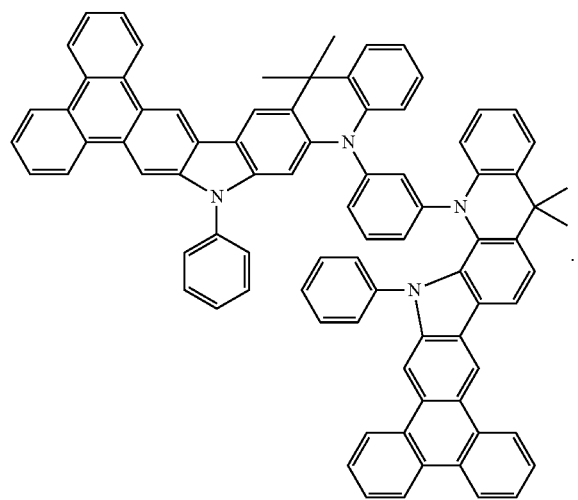

Detailed preparation for the material in the present invention could be clarified by exemplary embodiments, but the present invention is not limited to exemplary embodiments. EXAMPLE 1-6 show the preparation for some EXAMPLES of the material in the present invention. EXAMPLE 7 show the fabrication of organic EL device and I-V-B, half-life time of organic EL device testing report.

Example 1

Synthesis of Compound5

Synthesis of Intermediate A

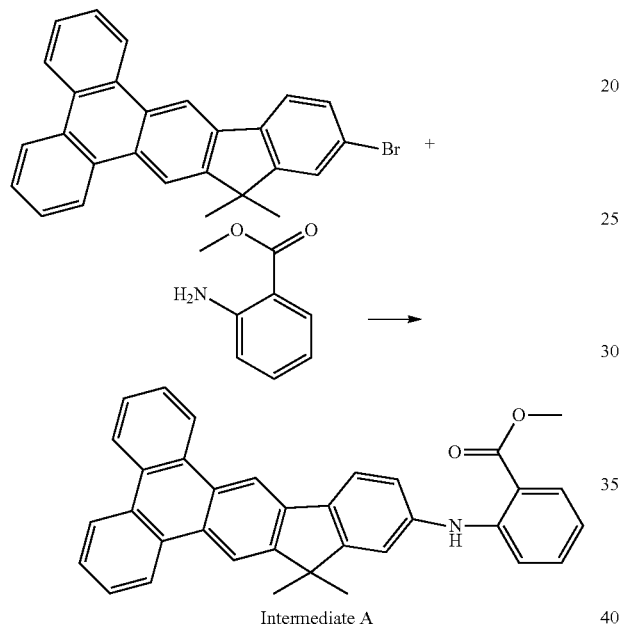

Intermediate A

A mixture of 5.0 g (11.8 mmol) of 12-bromo-10,10-dimethyl-10H-indeno[1,2-b]triphenylene, 2.0 g (13.0 mmol) of methyl 2-aminobenzoate, 0.13 g (0.59 mmol) of Pd(OAc)2, 0.17 g (0.59 mmol) tri-tert-butylphosphonium tetrafluoroborate, 3.9 g (17.7 mmol) of sodium tert-butoxide, 50 ml of Toluene was degassed and placed under nitrogen gas, and then heated at 110° C. for 16 h. After finishing the reaction, the mixture was allowed to cool to room temperature. The organic layer was extracted with dichloromethane and water, dried with anhydrous MgSO4, the solvent was removed and the residue was purified by column chromatography on silica to give product (3.2 g, 56%).

Synthesis of Intermediate B

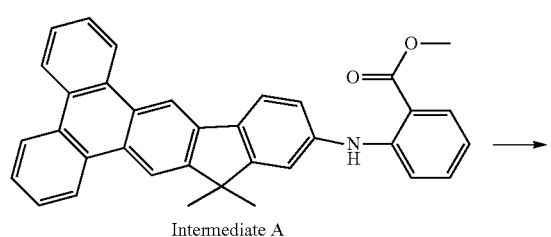

Intermediate A

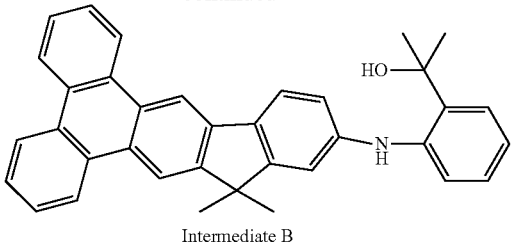

Intermediate B

Under the nitrogen gas, 3.2 g (6.6 mmol) of Intermediate A was stirred in dry THF, and methyl magnesium bromide (4.6 equivalent) was slowly dropped. The mixture was stirred for 16 h at room temperature. After completion of the reaction, distilled water was slowly added, and the mixture was extracted using ethyl acetate, wash with water. The organic layer was extracted with dichloromethane and water, dried with anhydrous MgSO4, the solvent was removed and the residue was purified by column chromatography on silica to give product (1 g, 32%).

Synthesis of Intermediate C

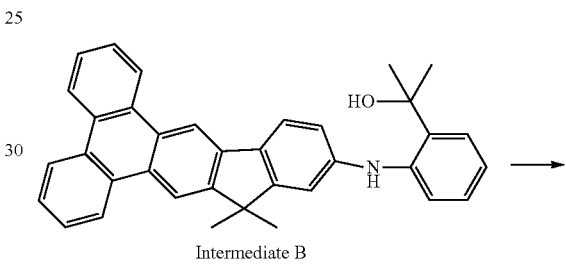

Intermediate B

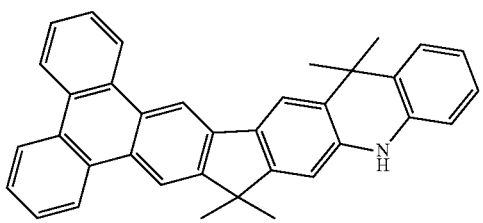

Intermediate C

A mixture of 3 g (6.0 mmol) of Intermediate B and excess phosphoric acid solvent (100 ml) was stirred at room temperature. After stirring the mixture for more than 16 h, distilled water (100-150 ml) was slowly added. The mixture was stirred for 0.5 to 1 hour, and the precipitated solids were filtered. The filtered solids were extracted using sodium hydroxide aqueous solution and dichloromethane solvent, and moisture was removed from the organic layer using magnesium sulfate. The residual solvent was removed then Intermediate C was obtained (2 g, 72%). MS (m/z, FAB+): 475.6

Synthesis of Compound5

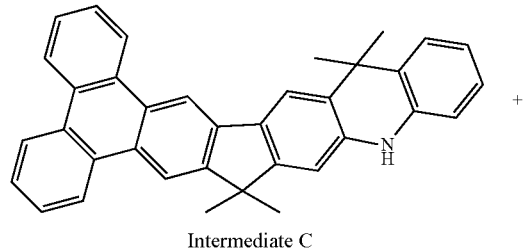

Intermediate C

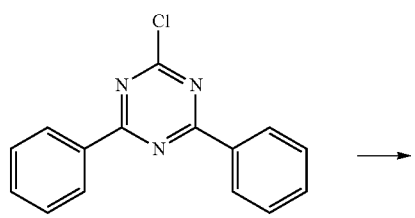

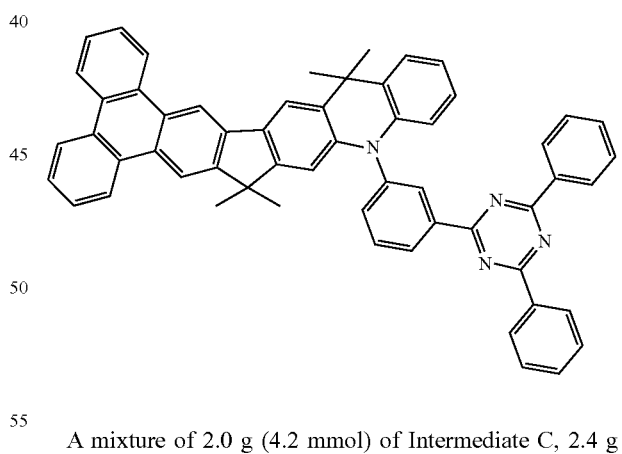

A DMF solution (30 ml) of Intermediate C (2 g, 4.2 mmol) was slowly added to a DMF solution (30 ml) of NaH (60% in oil) (0.84 g, 21.0 mmol). At ice-bath, 2-chloro-4,6-diphenyl-1,3,5-triazine (2.2 g, 8.4 mmol) was add to the mixture, then stirred at room temperature. After 30 min, the reaction mixture was poured into water to give a solid. The obtained solid was purified with sublimation to give Compound5(0.7 g, 40%). MS (m/z, FAB+): 706.8

Example 2

Synthesis of Compound11

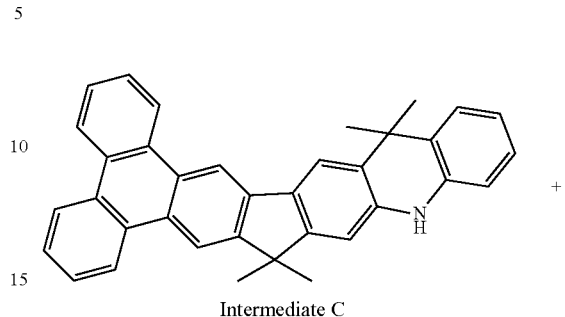

Intermediate C

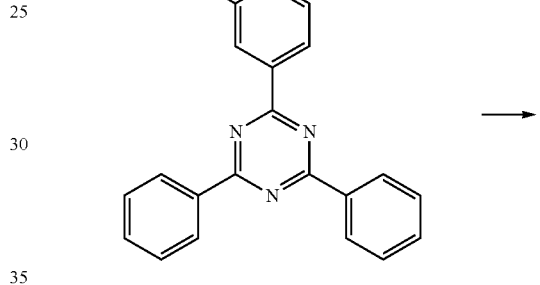

A mixture of 2.0 g (4.2 mmol) of Intermediate C, 2.4 g (6.3 mmol) of 2-(3-bromophenyl)-4,6-diphenyl-1,3,5-triazine, 0.07 g (0.3 mmol) of Pd(OAc)2, 0.09 g (0.3 mmol) tri-tert-butylphosphonium tetrafluoroborate, 0.9 g (9.46 mmol) of sodium tert-butoxide, 50 ml of Toluene was degassed and placed under nitrogen gas, and then heated at 120° C. for 16 h. After finishing the reaction, the mixture was allowed to cool to room temperature. The organic layer was extracted with dichloromethane and water, dried with anhydrous MgSO4, the solvent was removed and the residue was purified by column chromatography on silica to give Compound11 (1.9 g, 55%). MS (m/z, FAB+): 783.0

Example 3

Synthesis of Compound17

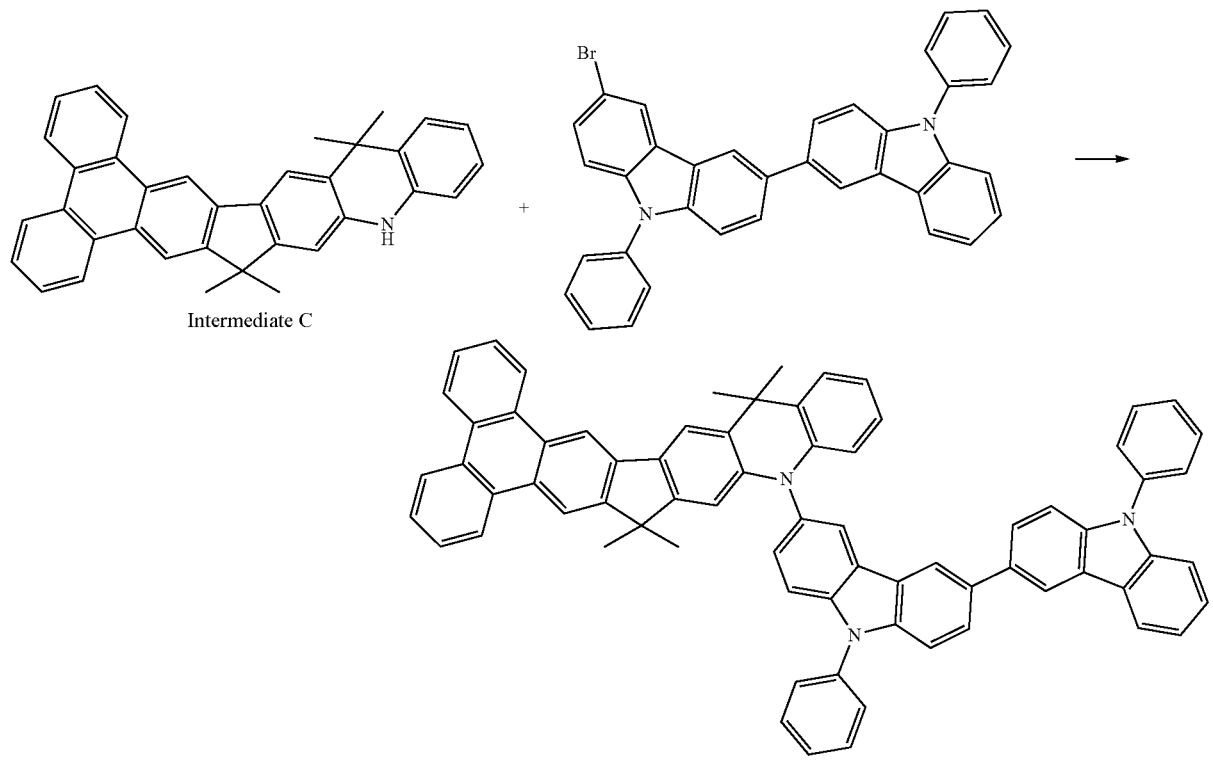

A mixture of 2.0 g (4.2 mmol) of Intermediate C, 3.5 g (6.3 mmol) of 6-bromo-9,9'-diphenyl-9H,9'H-3,3'-bicarbazole, 0.07 g (0.3 mmol) of Pd(OAc)2, 0.09 g (0.3 mmol) tri-tert-butylphosphonium tetrafluoroborate, 0.9 g (9.46 mmol) of sodium tert-butoxide, 50 ml of Toluene was degassed and placed under nitrogen gas, and then heated at 120° C. for 16 h. After finishing the reaction, the mixture was allowed to cool to room temperature. The organic layer was extracted with dichloromethane and water, dried with anhydrous MgSO4, the solvent was removed and the residue was purified by column chromatography on silica to give Compound17 (1.9 g, 48%). MS (m/z, FAB+): 957.8

Synthesis of Intermediate D

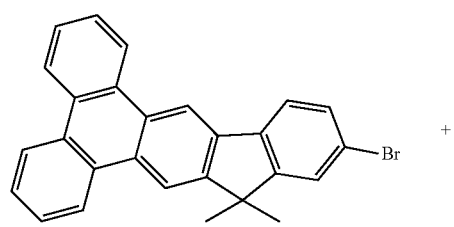

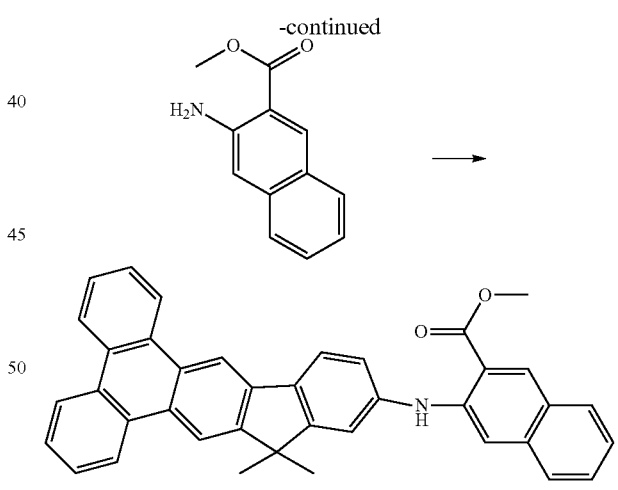

A mixture of 5.0 g (11.8 mmol) of 12-bromo-O, 10-dimethyl-10H-indeno[1,2-b]triphenylene, 2.6 g (13.0 mmol) of methyl 3-amino-2-naphthoate, 0.13 g (0.59 mmol) of Pd(OAc)2, 0.17 g (0.59 mmol) tri-tert-butylphosphonium tetrafluoroborate, 3.9 g (17.7 mmol) of sodium tert-butoxide, 80 ml of Toluene was degassed and placed under nitrogen gas, and then heated at 110° C. for 16 h. After finishing the reaction, the mixture was allowed to cool to room temperature. The organic layer was extracted with dichloromethane and water, dried with anhydrous MgSO4, the solvent was removed and the residue was purified by column chromatography on silica to give product (3.2 g, 51%).

Synthesis of Intermediate E

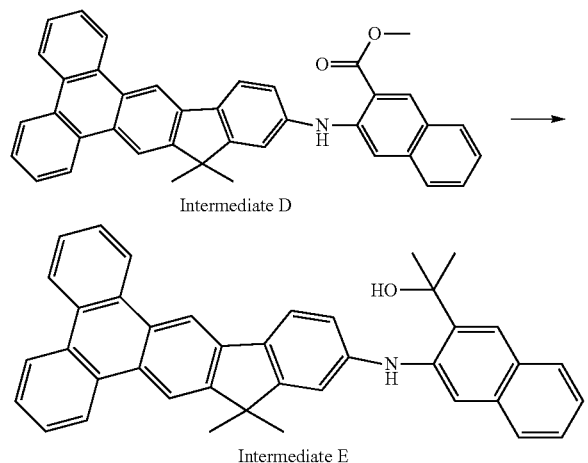

Under the nitrogen gas, 3.2 g (5.8 mmol) of Intermediate D was stirred in dry THF, and methyl magnesium bromide (4.6 equivalent) was slowly dropped. The mixture was stirred for 16 h at room temperature. After completion of the reaction, distilled water was slowly added, and the mixture was extracted using ethyl acetate, wash with water. The organic layer was extracted with dichloromethane and water, dried with anhydrous MgSO4, the solvent was removed and the residue was purified by column chromatography on silica to give product (1.1 g, 36%).

Synthesis of Intermediate F

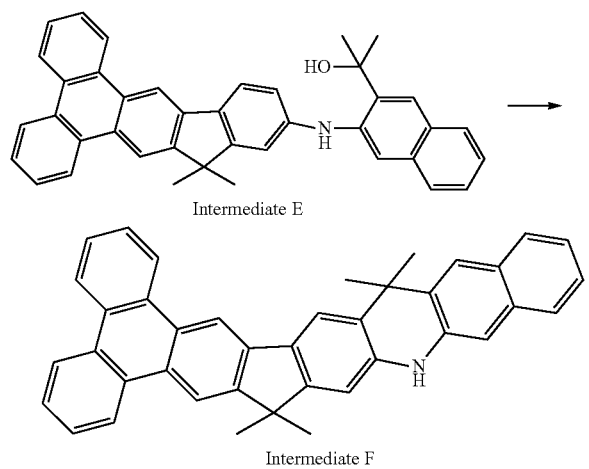

A mixture of 1.1 g (2.1 mmol) of Intermediate E and excess phosphoric acid solvent (66 ml) was stirred at room temperature. After stirring the mixture for more than 16 h, distilled water (~120 ml) was slowly added. The mixture was stirred for 1 hour, and the precipitated solids were filtered. The filtered solids were extracted using sodium hydroxide aqueous solution and dichloromethane solvent, and moisture was removed from the organic layer using magnesium sulfate. The residual solvent was removed then Intermediate C was obtained (0.8 g, 76%). MS (m/z, FAB+): 526.1

Example 4

Synthesis of Compound6

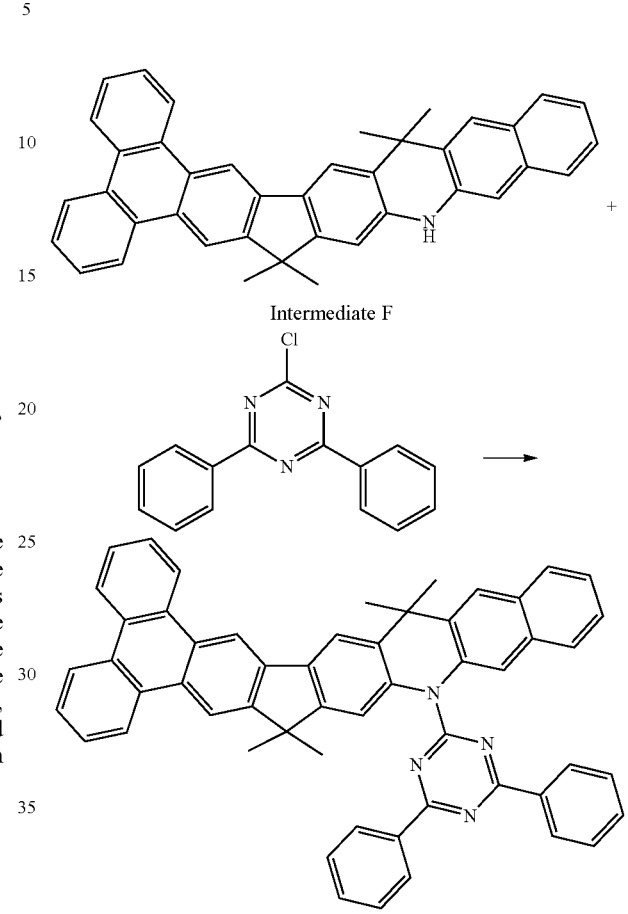

A DMF solution (30 ml) of Intermediate F (1 g, 1.9 mmol) was slowly added to a DMF solution (30 ml) of NaH (60% in oil) (0.38 g, 9.5 mmol). At ice-bath, 2-chloro-4,6-diphenyl-1,3,5-triazine (1.5 g, 5.7 mmol) was add to the mixture, then stirred at room temperature. After 30 min, the reaction mixture was poured into water to give a solid. The obtained solid was purified with sublimation to give compound6 (0.6 g, 42%). MS (m/z, FAB+): 756.5

Example 5

Synthesis of Compound12

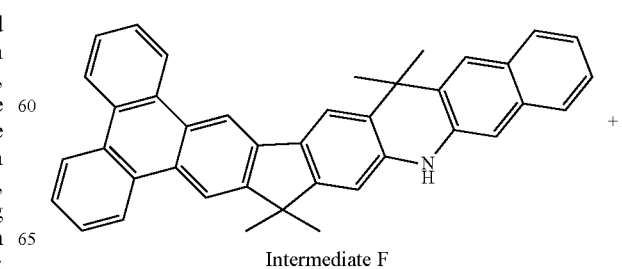

-continued

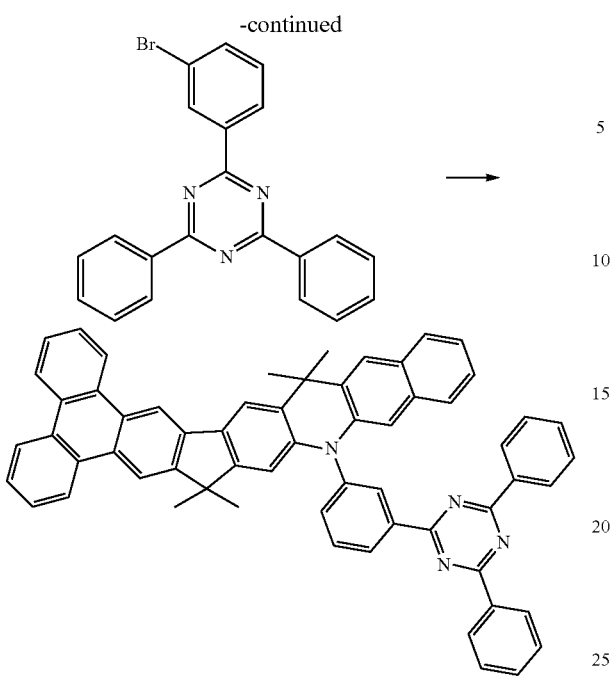

A mixture of 2.2 g (4.2 mmol) of Intermediate F, 2.4 g (6.3 mmol) of 2-(3-bromophenyl)-4,6-diphenyl-1,3,5-triazine, 0.07 g (0.3 mmol) of Pd(OAc)2, 0.09 g (0.3 mmol) tri-tert-butylphosphonium tetrafluoroborate, 0.9 g (9.46 mmol) of sodium tert-butoxide, 50 ml of Toluene was degassed and placed under nitrogen gas, and then heated at 120° C. for 16 h. After finishing the reaction, the mixture was allowed to cool to room temperature. The organic layer was extracted with dichloromethane and water, dried with anhydrous MgSO4, the solvent was removed and the residue was purified by column chromatography on silica to give product. The obtained solid was purified with sublimation to give compound12 (1.6 g, 48%). MS (m/z, FAB+): 832.9

Example 6

Synthesis of Compound18

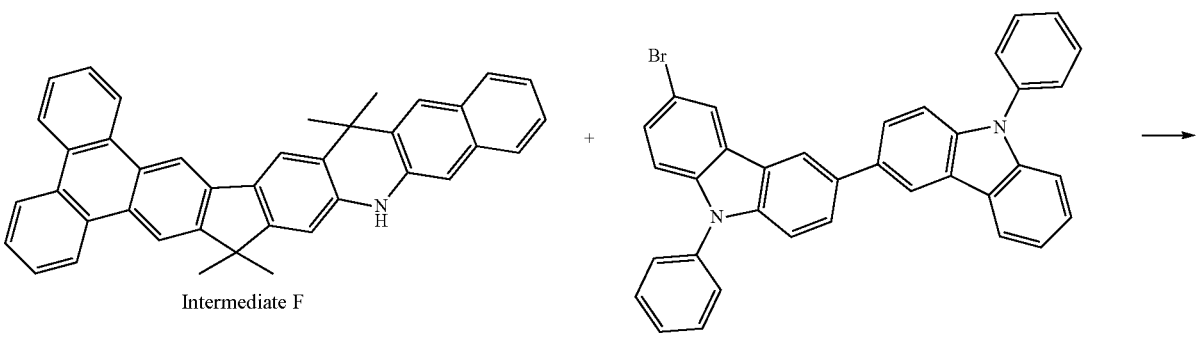

Intermediate F

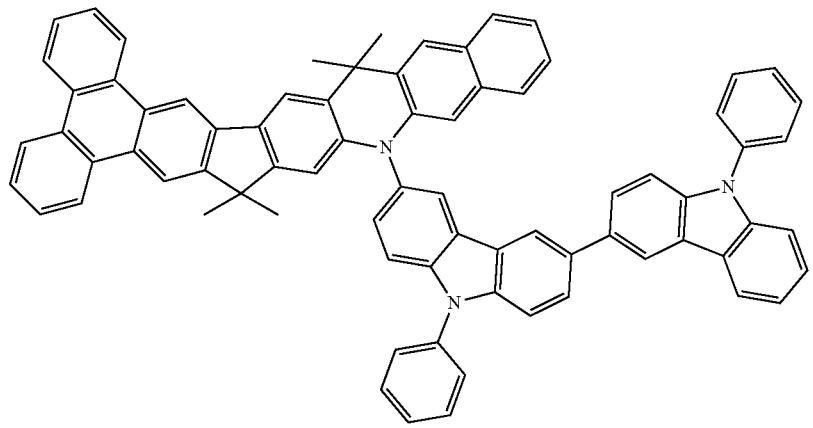

A mixture of 2.2 g (4.2 mmol) of Intermediate F, 3.5 g (6.3 mmol) of 6-bromo-9,9'-diphenyl-9H,9'H-3,3'-bicarbazole, 0.07 g (0.3 mmol) of Pd(OAc)2, 0.09 g (0.3 mmol) tri-tert-butylphosphonium tetrafluoroborate, 0.9 g (9.46 mmol) of sodium tert-butoxide, 50 ml of Toluene was degassed and placed under nitrogen gas, and then heated at 120° C. for 16 h. After finishing the reaction, the mixture was allowed to cool to room temperature. The organic layer was extracted with dichloromethane and water, dried with anhydrous MgSO4, the solvent was removed and the residue was purified by column chromatography on silica to give product. The obtained solid was purified with sublimation to give compound18 (1.7 g, 41%). MS (m/z, FAB+): 1007.9

Measurement Method of Delayed Fluorescence Compound for Photophysical Properties Photophysical Characterization: Synthesized compounds were subject to purification by temperature-gradient sublimation in high vacuum before use in subsequent studies. Thin films for photophysical characterization were prepared by thermal evaporation on quartz substrates at 1-2 A/sec in a vacuum chamber with a base pressure of <10-6 torr. Absorption spectra of the resulting thin films and dilute solutions were characterized by a UV-vis-NIR spectrophotometer (UV-1650 PC, Shimadzu). Photoluminescence (PL) spectra, photoluminescence quantum yields (PLQYs), and phosphorescence spectra were characterized by a spectrofluorimeter (FluoroMax-P, Horiba Jobin Yvon Inc.). PLQYs of thin films or dilute solutions were determined using this spectrofluorimeter equipped with a calibrated integrating sphere. The selected monochromatic excitation light was used to excite samples placed in the calibrated integrating sphere. By comparing the spectral intensities of the monochromatic excitation light and the PL emission, the PL quantum yields were determined. Phosphorescence spectra of thin films or dilute solutions were conducted at 77K (the liquid nitrogen temperature) by the spectrofluorometer equipped with a microsecond flash lamp as the pulsed excitation source. A 10-ms delay time was inserted between the pulsed excitation and the collection of the emission spectrum. Time-resolved PL (PL decay curves) was measured by monitoring the decay of the intensity at the PL peak wavelength using the time-correlated single-photon counting technique with a fluorescence lifetime system (Fluoro-Cube, Horiba Jobin Yvon Inc.) and nanosecond pulsed light excitation from a UV light-emitting diode (300 nm). The samples were placed in a vacuum cryostat chamber with the temperature control. The PL spectra of the prompt and delayed components were collected using this same fluorescence lifetime system with a 200-ns delay time and a 10-us delay time between the pulsed excitation and the collection of the emission spectrum. Electrochemical Characterization: Cyclic voltammetry by a CHI 619B potentiostat was used to measure oxidation/reduction potentials. The oxidation potential was determined by cyclic voltammetry (CV) using 0.1M n-Bu4NPF6 (TBAPF6) in CH2Cl2 as a supporting electrolyte and a scan rate of 100 mV s−1. The reduction potential was recorded using 0.1M n-Bu4NClO4 (TBAP) in DMF as a supporting electrolyte and a scan rate of 100 mV s−1. A standard 3-electrode cell comprising silver/silver chloride (Ag/AgCl), a platinum wire and a glassy carbon electrode as the reference, counter, and working electrodes, respectively, were used. All potentials were recorded versus Ag/AgCl (saturated) as a reference electrode. Oxidation of the ferrocene/ferrocenium (Fc/Fc+) redox couple in CH2Cl2/TBAPF6 occurs at E'o=+ 0.47V and reduction of the ferrocene/ferrocenium (Fc/Fc+) redox couple in DMF/TBAP occurs at E"o=+0.51 V vs. Ag/AgCl (saturated) collecting the total emission fluxes with a calibrated integrating-sphere measurement system.

General Method of Producing Organic El Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device, and N,N-Bis (naphthalene-1-yl)-N,N-bis (phenyl)-benzidine (NPB) is most widely used as the hole transporting layer, N-(biphenyl-4-yl)-9,9-dimethyl-N-(4'-phenylbiphenyl-4-yl)-9H-fluoren-2-amine (EB2) is used as electron blocking layer, and the chemical structure shown below:

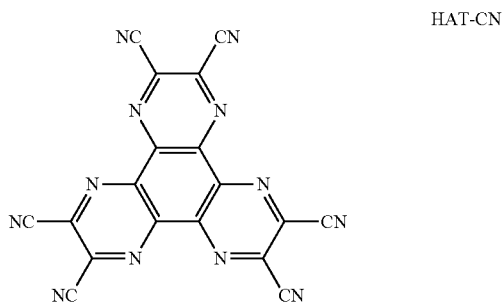

HAT-CN

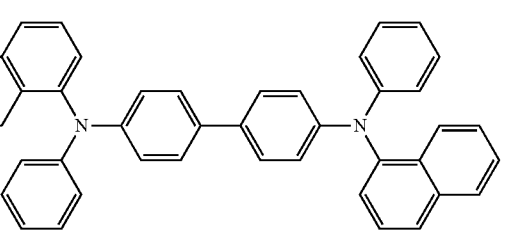

NPB

-continued

EB2

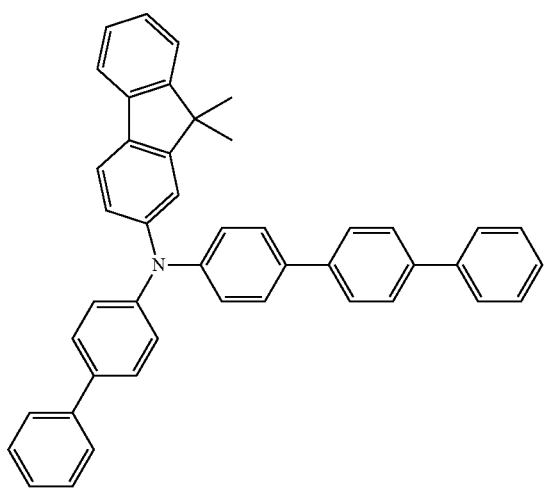

In the present invention the phosphorescent emitting host used as the following formulas for comparable with EX1 to EX6 in the present invention:

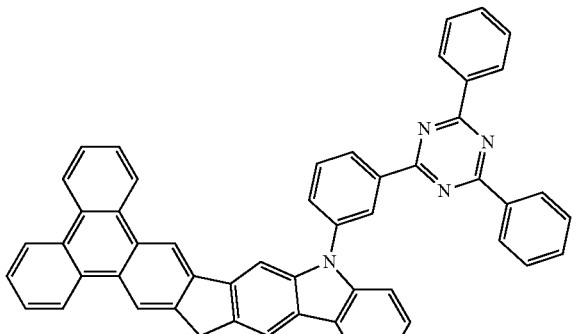

wherein X is a divalent bridge selected from the atom or group consisting from O, S, $C(R_8)_2$, $N(R_9)$ and $Si(R_{10})_2$, m represents an integer of 0 to 4, n represents an integer of 0 to 8, $R_1$ to $R_4$ and $R_8$ to $R_{10}$ are independently selected from the group consisting of a hydrogen atom, a halide, a substituted or unsubstituted alkyl group having 1 to 20 carbon atoms, a substituted or unsubstituted aryl group having 6 to 30 carbon atoms and a substituted or unsubstituted heteroaryl group having 3 to 30 carbon atoms; wherein the phosphorescent light emitting host is selected from the group consisting of:

H5
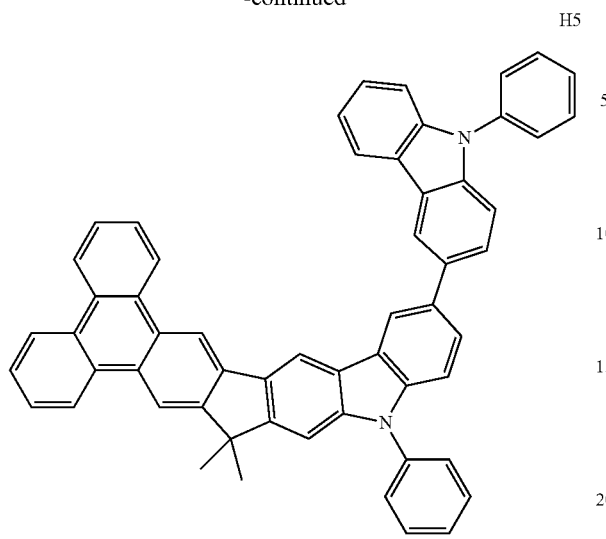
H6
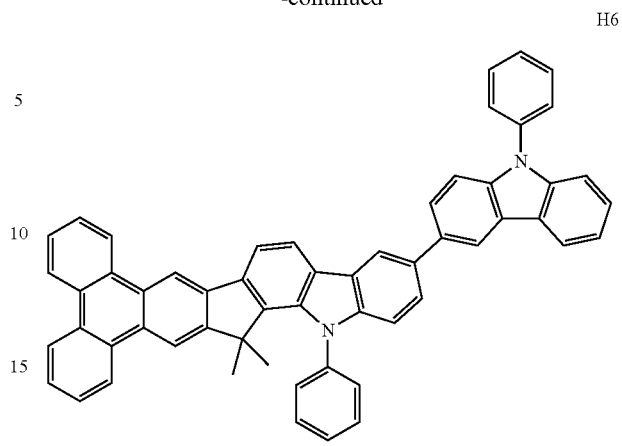
In the present invention another suitable phosphorescent emitting host used to co-deposition with H1 to H3 and EX1 to EX6 in the present invention as the following formulas:
H7
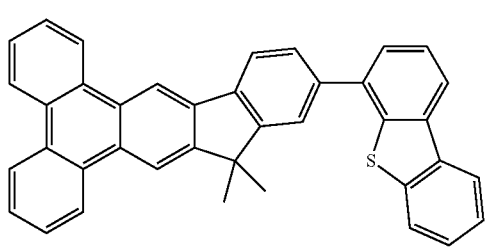
H8
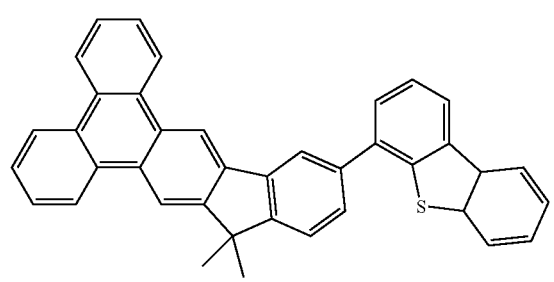
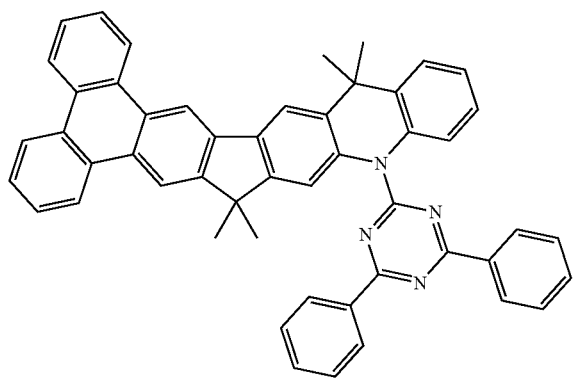
Compound5(C5)
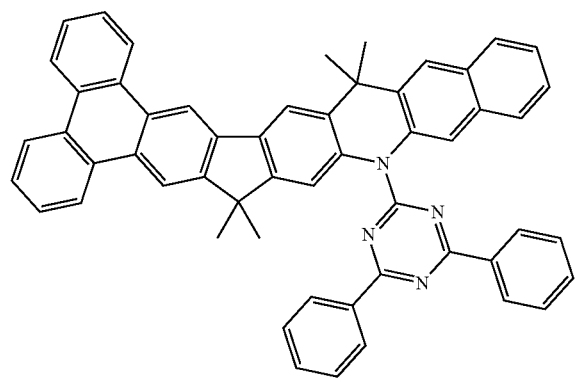
Compound6(C6)
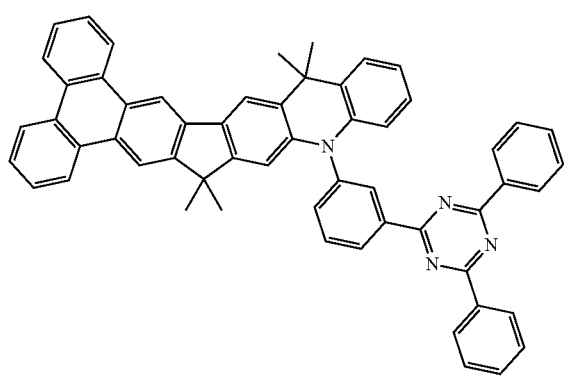
Compound11(C11)
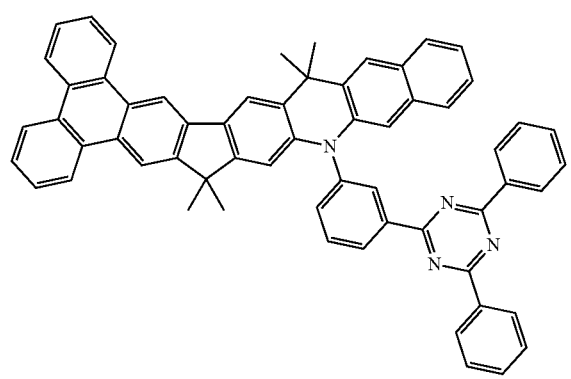
Compound12(C12)

Compound17(C17)

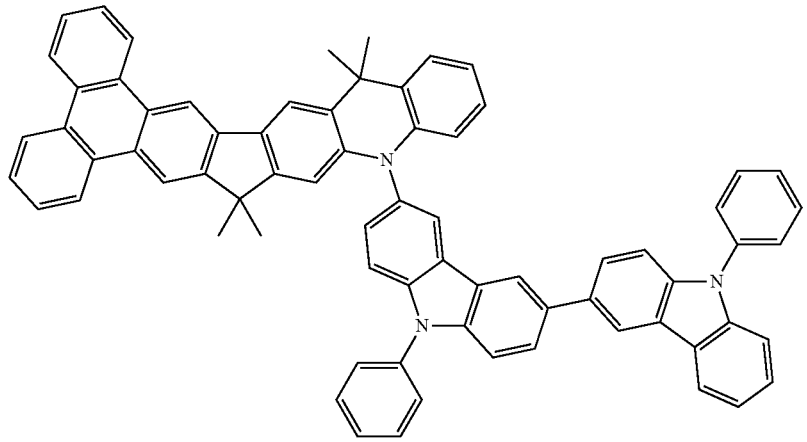

Compound18(C18)

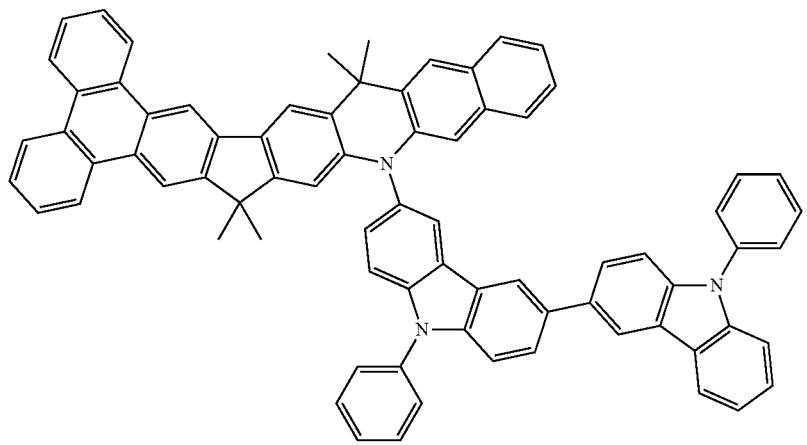

1,3-di(9H-carbazol-9-yl)benzene(mCP) is used as delayed fluorescence host for light emitting layer, and doped with EX1 to EX6 for organic EL device in the present invention.

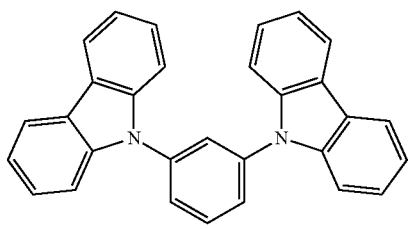

mCP

Organic iridium complexes are widely used as phosphorescent dopant for light emitting layer, and Ir(ppy)$_3$ is widely used for phosphorescent dopant of light emitting layer for doping in phosphorescent emitting host in the present invention.

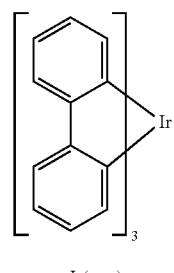

Ir(ppy)$_3$

HB3 (see the following chemical structure) is used as hole blocking material (HBM) and 2-(10,10-dimethyl-10H-indeno[2,1-b]triphenylen-12-yl)-4,6-diphenyl-1,3,5-triazine (ET2) is used as electron transporting material to co-deposit with 8-hydroxyquinolato-lithium (LiQ) in organic EL device. The prior art of other OLED materials for producing standard organic EL device control and comparable material in this invention shown its chemical structure as follows:

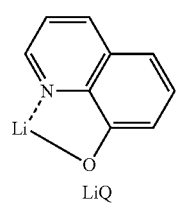

LiQ

ET2

HB3

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 7

Using a procedure analogous to the above mentioned general method, phosphorescent emitting organic EL device having the following device structure was produced (See FIG. 1). Device: ITO/HAT-CN (20 nm)/NPB (110 nm)/EB2 (5 nm)/emitting host doped 12% phosphorescent emitting dopant (30 nm)/HBM (10 nm)/ET2 doped 45% LiQ(35 nm)/LiQ(1 nm)/Al(160 nm), and delayed fluorescence device having the following device structure was produced (See FIG. 1). Device: ITO/HAT-CN(20 nm)/NPB (110 nm)/EB2 (5 nm)/mCP doped 20% delayed fluorescence compound (25 nm)/HBM(10 nm)/ET2 doped 45% LiQ(35 nm)/LiQ(1 nm)/Al(160 nm). (HBM=hole blocking material) The I—V-B (at 1000 nits) and half-life time of phosphorescent emitting organic EL device and delayed fluorescence device testing report as Table 1. The $T_{70}$ is defined that the initial luminance of 3000 $cd/m^2$ has dropped to 2100 $cd/m^2$.

TABLE 1

| Emitting host (Cohost = 1:1) | Emitting dopant | HBM | Voltage (V) | Efficiency (cd/A) | $T_{70}$ |
|---|---|---|---|---|---|
| Compound5 | $Ir(ppy)_3$ | HB3 | 4.5 | 35 | 510 |
| Compound6 | $Ir(ppy)_3$ | HB3 | 4.7 | 32 | 430 |
| Compound11 | $Ir(ppy)_3$ | HB3 | 4.5 | 38 | 540 |
| Compound12 | $Ir(ppy)_3$ | HB3 | 4.9 | 41 | 450 |
| Compound17 | $Ir(ppy)_3$ | HB3 | 5.0 | 26 | 390 |
| Compound18 | $Ir(ppy)_3$ | HB3 | 5.2 | 20 | 370 |
| H1 | $Ir(ppy)_3$ | HB3 | 4.5 | 30 | 330 |
| H2 | $Ir(ppy)_3$ | HB3 | 4.0 | 28 | 350 |
| H3 | $Ir(ppy)_3$ | HB3 | 4.2 | 25 | 240 |
| Compound5 + H5 | $Ir(ppy)_3$ | HB3 | 3.6 | 58 | 620 |
| Compound5 + H7 | $Ir(ppy)_3$ | HB3 | 3.5 | 55 | 590 |
| Compound11 + H6 | $Ir(ppy)_3$ | HB3 | 3.2 | 50 | 550 |
| Compound11 + H8 | $Ir(ppy)_3$ | HB3 | 3.0 | 52 | 580 |
| Compound5 + H5 | $Ir(ppy)_3$ | C5 | 4.0 | 55 | 460 |
| Compound5 + H5 | $Ir(ppy)_3$ | C6 | 4.3 | 50 | 460 |
| Compound5 + H5 | $Ir(ppy)_3$ | C11 | 4.0 | 44 | 450 |
| mCP | C5 | HB3 | 6.5 | 22 | 75 |
| mCP | C6 | HB3 | 6.0 | 28 | 80 |
| mCP | C11 | HB3 | 6.8 | 16 | 65 |

In the above preferred embodiments for organic EL device test report (see Table 1), we shown that the material with a general formula(1) or formula(2) used as phosphorescent emitting host and hole blocking material in the present invention display good performance than the prior art of OLED materials. Additional, C5, C6 and C11 used as delayed fluorescence dopant to co-deposit with mCP can show good efficiency reach to 28 cd/A.

To sum up, the present invention discloses a material which can be used for organic EL device is disclosed. More specifically, an organic EL device employing the material as phosphorescent emitting host, delayed fluorescence dopant, and hole blocking layer (HBL). The mentioned the material is represented by the following formula(1) or formula(2):

formula(1)

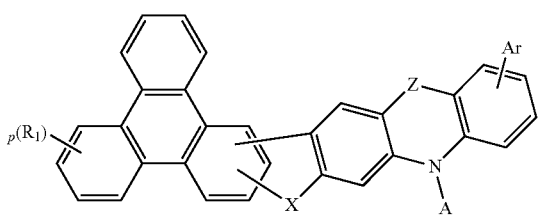

-continued

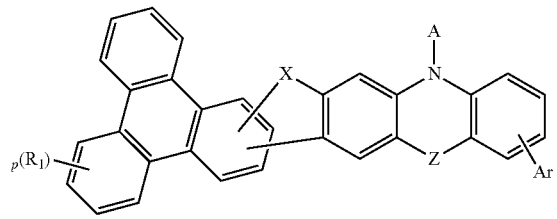

formula(2)

wherein p represents an integer of 0 to 8, X independently represents a divalent bridge selected from the atom or group consisting from O, S, C($R_2$)($R_3$), N($R_4$) and Si($R_5$)($R_6$), Z independently represents a divalent bridge selected from the atom or group consisting from C($R_7$)($R_8$), N($R_9$), Si($R_{10}$) ($R_{11}$) and C=O, Ar represents a hydrogen atom, or a fused carbocyclic ring; A is selected from the group consisting of a hydrogen, a substituted or unsubstituted aryl group having 6 to 60 carbon atoms or a substituted or unsubstituted heteroaryl group having 3 to 60 carbon atoms, and provided that A represents a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted quinoline group, a substituted or unsubstituted isoquinoline group, a substituted or unsubstituted quinazoline group, a substituted or unsubstituted phenanthroline group, a substituted or unsubstituted dihydroacridine group, a substituted or unsubstituted phenothiazine group, a substituted or unsubstituted phenoxazine group, and a substituted or unsubstituted dihydrophenazine group; $R_1$ to $R_{11}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. A material with a general formula(1) or formula(2) as follows:

formula(1)

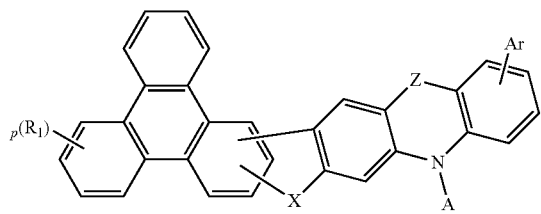

-continued

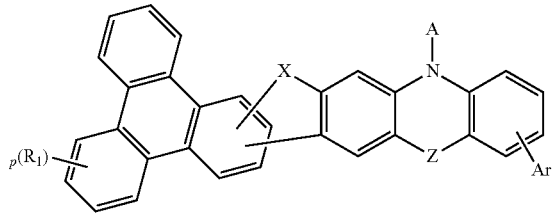

formula(2)

wherein p represents an integer of 0 to 8, X independently represents a divalent bridge selected from the atom or group consisting from O, S, C($R_2$)($R_3$), N($R_4$) and Si($R_5$)($R_6$), Z independently represents a divalent bridge selected from the atom or group consisting from C($R_7$)($R_8$), N($R_9$), Si($R_{10}$) ($R_{11}$) and C=O, Ar represents a hydrogen atom, or a fused carbocyclic ring; A is a hydrogen, a substituted or unsubstituted aryl group having 6 to 60 carbon atoms or a substituted or unsubstituted heteroaryl group having 3 to 60 carbon atoms, and provided that when A is a substituted or unsubstituted heteroaryl group having 3 to 60 carbon atoms, A represents a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted triazinyl group, a substituted or unsubstituted diazinyl group, a substituted or unsubstituted pyridinyl group, a substituted or unsubstituted quinoline group, a substituted or unsubstituted isoquinoline group, a substituted or unsubstituted quinazoline group, a substituted or unsubstituted phenanthroline group, a substituted or unsubstituted dihydroacridine group, a substituted or unsubstituted phenothiazine group, a substituted or unsubstituted phenoxazine group, or a substituted or unsubstituted dihydrophenazine group; $R_1$ to $R_{11}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

2. The material according to claim 1, wherein the A is represented by the following formula(3) to formula(6):

Formula(3)

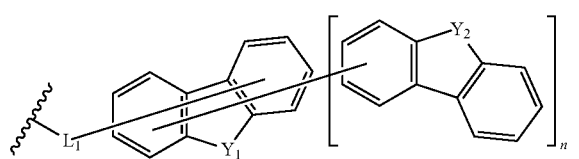

Formula(4)

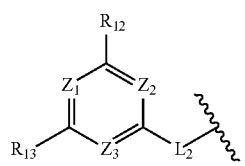

-continued

Formula(5)

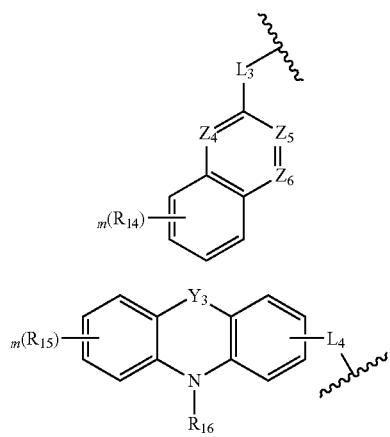

Formula(6)

wherein $L_1$ to $L_4$ represent a single bond, a substituted or unsubstituted arylene group having 6 to 30 ring carbon atoms, or a substituted or unsubstituted heterarylene group having 3 to 30 ring carbon atoms, m represents an integer of 0 to 4, n represents an integer of 0 or 1, $Y_1$ to $Y_3$ independently represent a divalent bridge selected from the atom or group consisting from O, S, $C(R_{17})(R_{18})$ and $N(R_{19})$, $Z_1$ to $Z_6$ represent a nitrogen atom or $C(R_s)$, and each $R_s$ represents a hydrogen, a phenyl, a substituted or unsubstituted alkyl group having 1 to 30 carbon atoms, and a substituted or unsubstituted aryl group having 6 to 30 carbon atoms; $R_{12}$ to $R_{19}$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

3. The material according to claim 1, wherein the material is selected from the group consisting of:

Compound 1

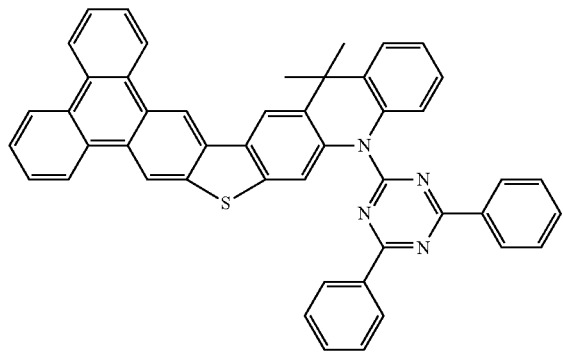

Compound 2

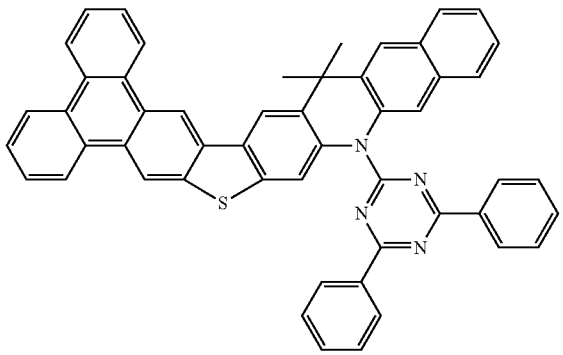

Compound 3

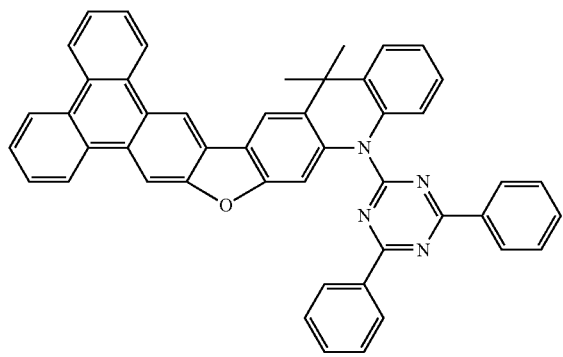

Compound 4

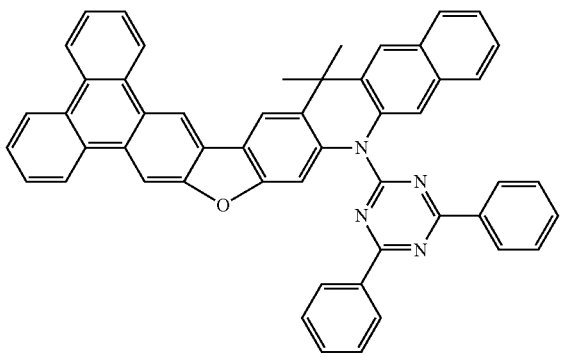

Compound 5

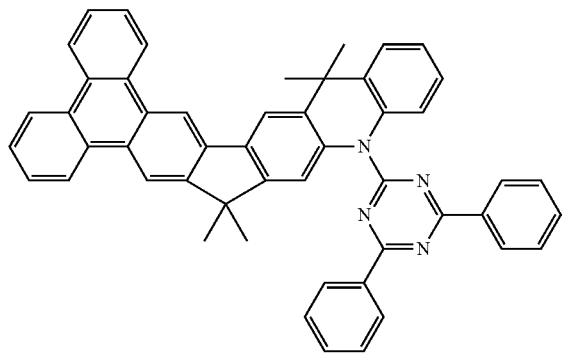

Compound 6

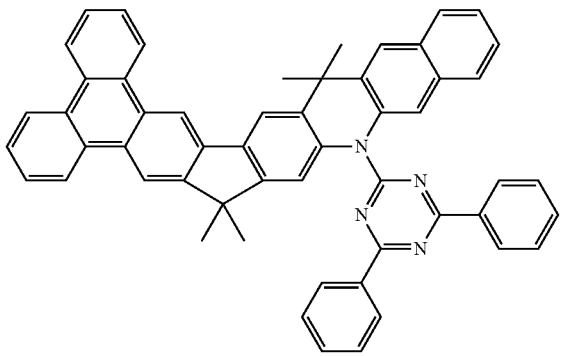

-continued
Compound 7
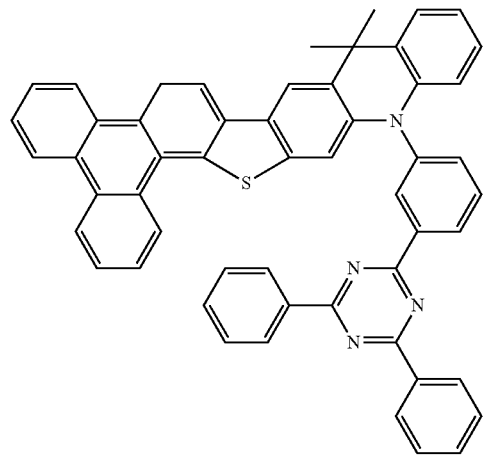
Compound 8
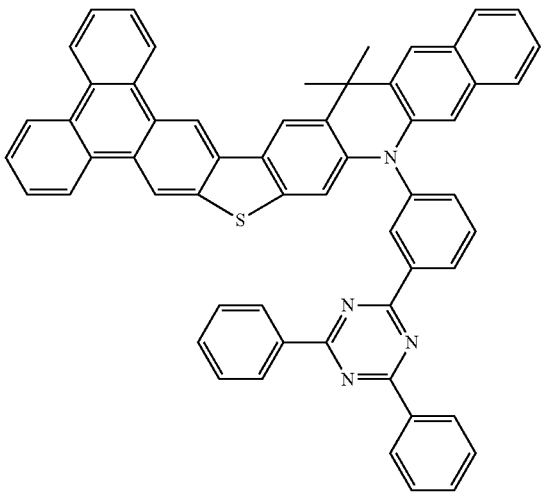
Compound 9
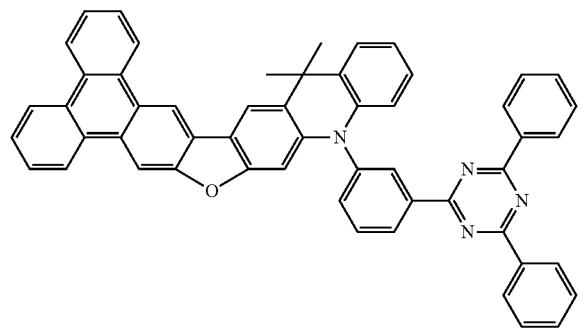
Compound 10
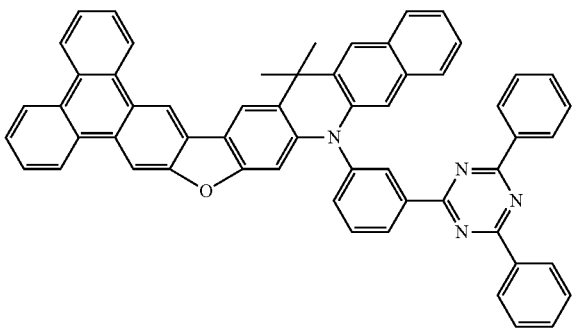
Compound 11
Compound 12
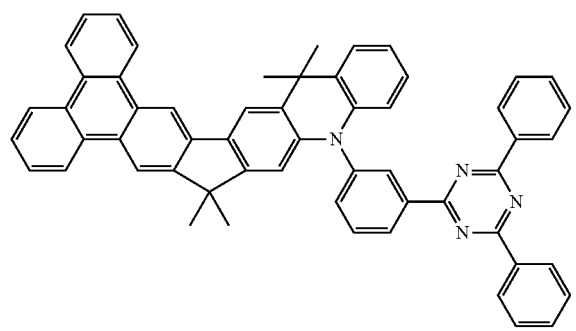
Compound 13
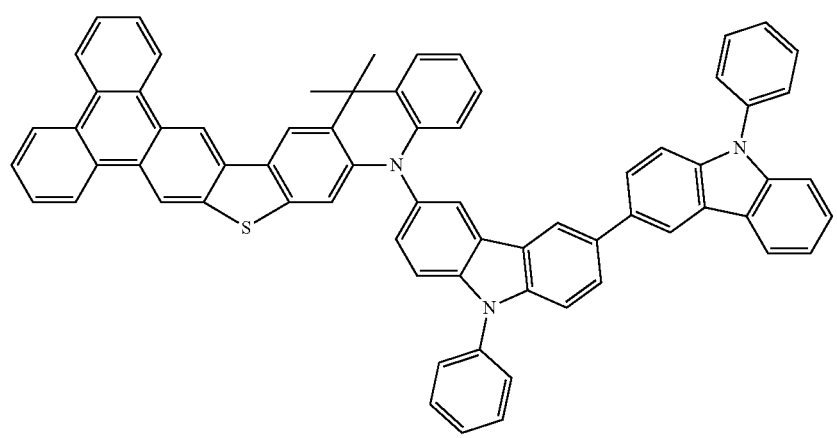

-continued
Compound 14
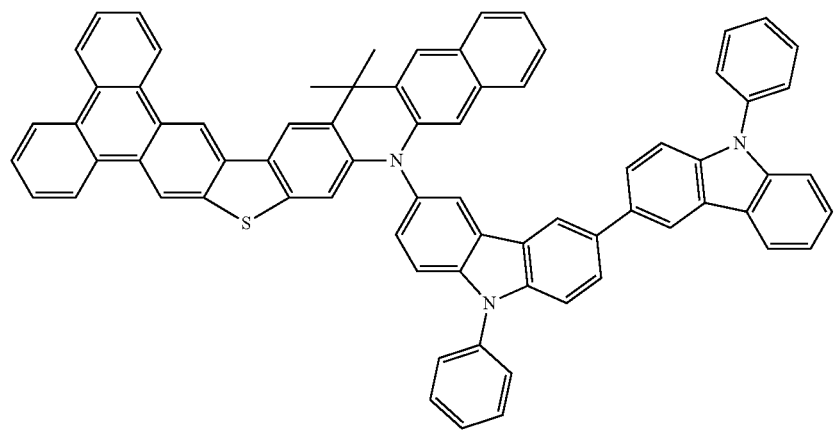
Compound 15
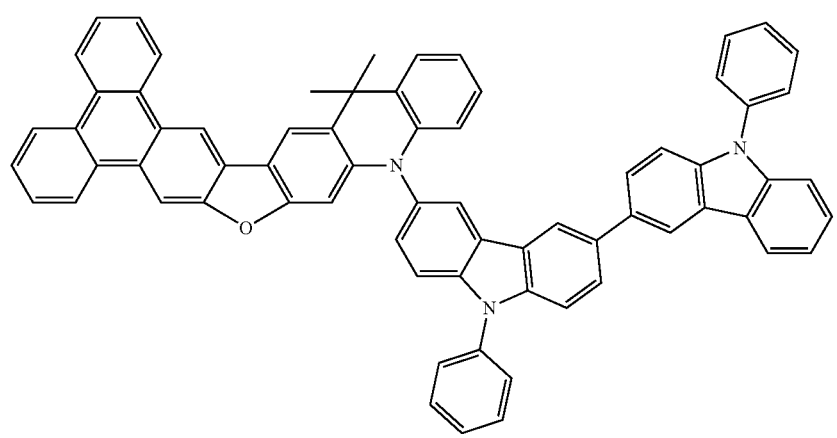
Compound16
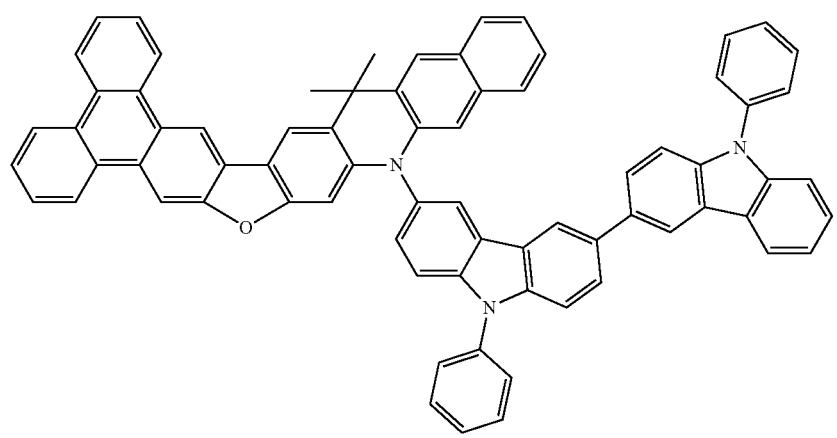

-continued
Compound 17
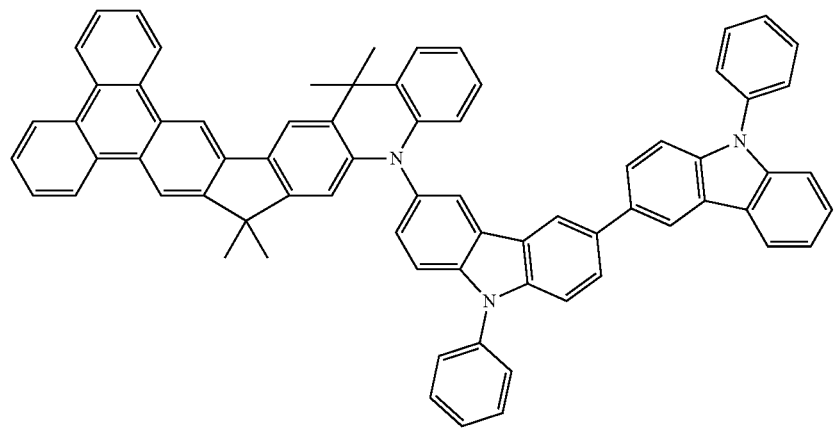
Compound 18
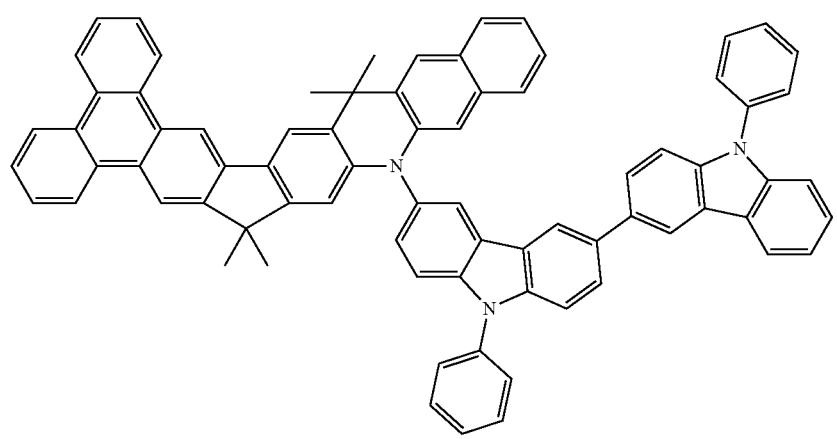
Compound 19
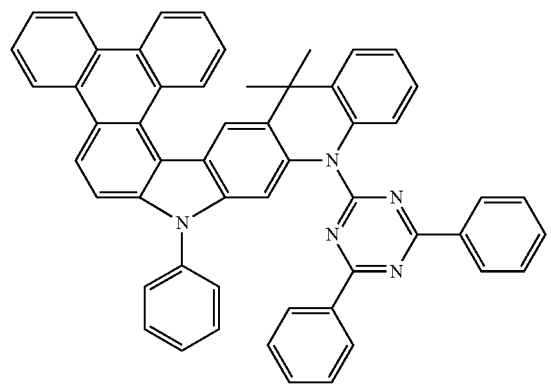
Compound 20
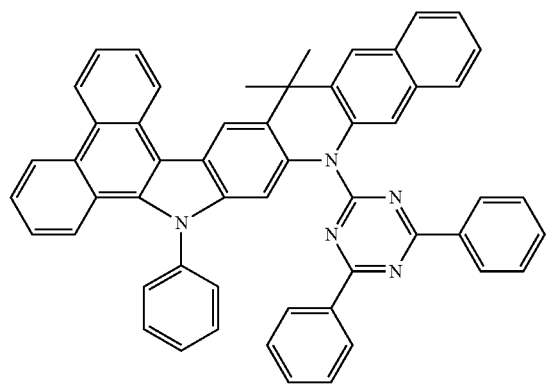
Compound 21
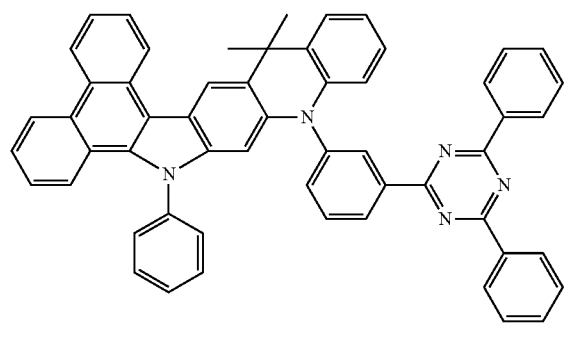
Compound 22
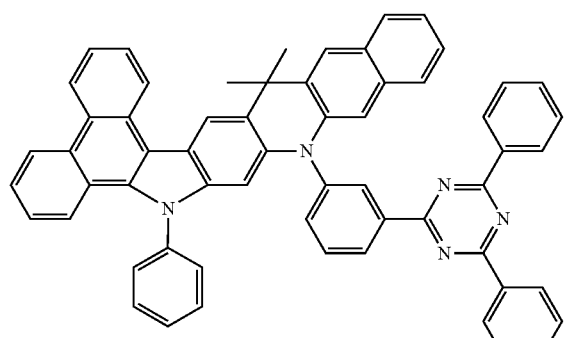

Compound 23
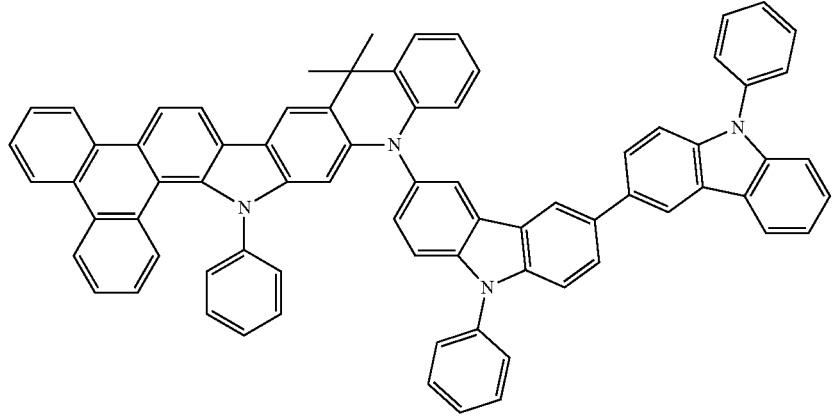
Compound 24
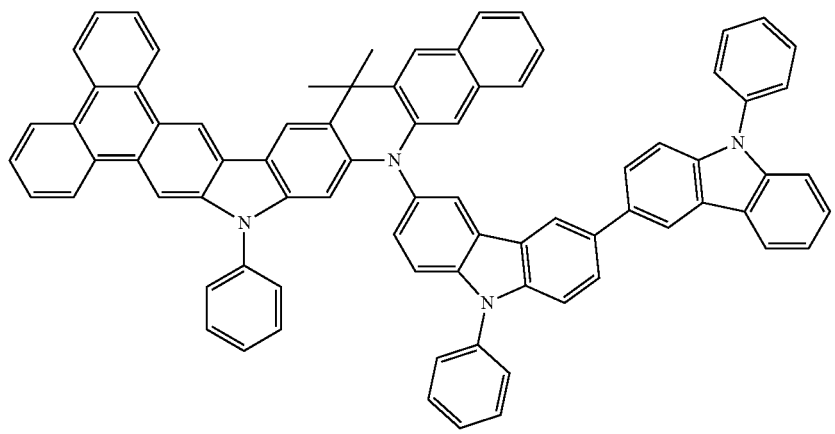
Compound 25
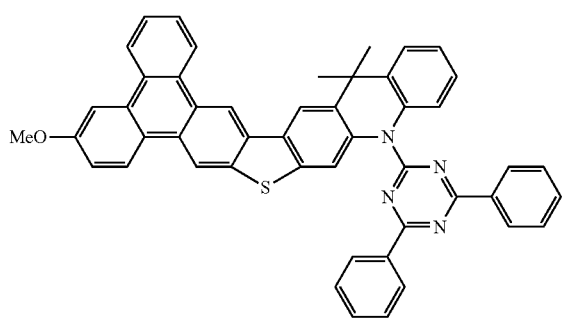
Compound 26
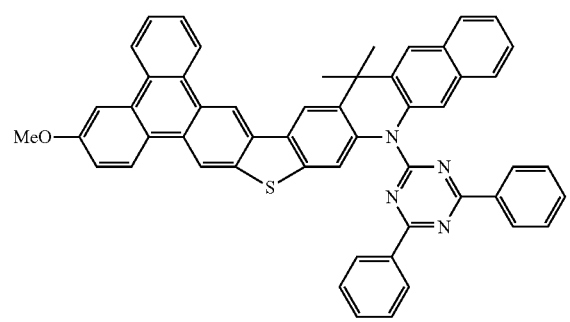
Compound 27
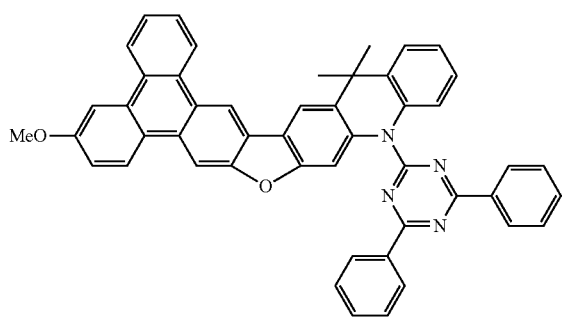
Compound 28
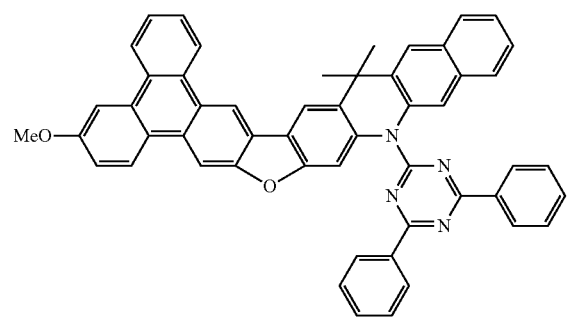

-continued
Compound 29
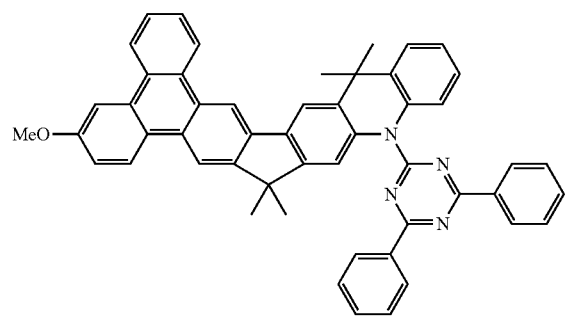
Compound 30
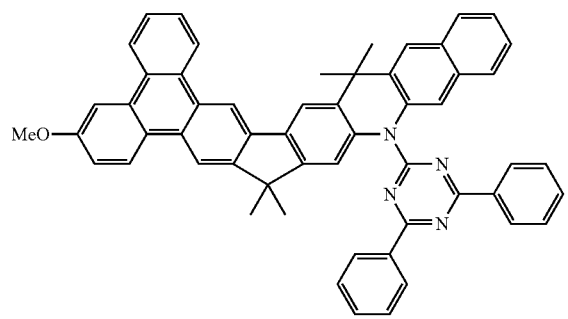
Compound 31
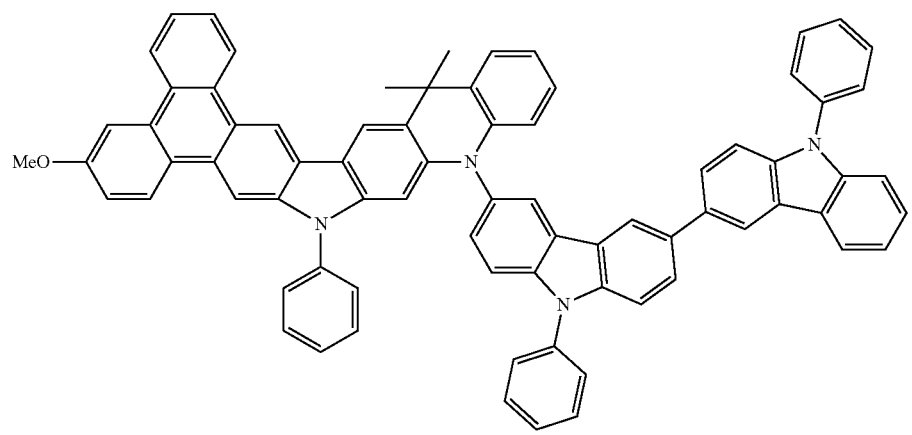
Compound 32
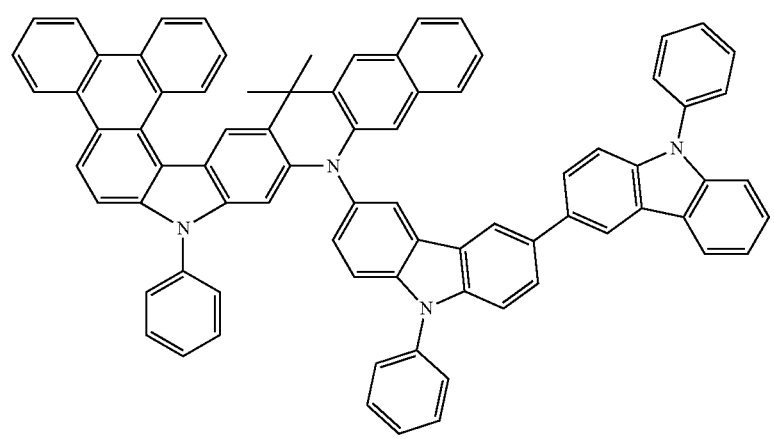

Compound 33
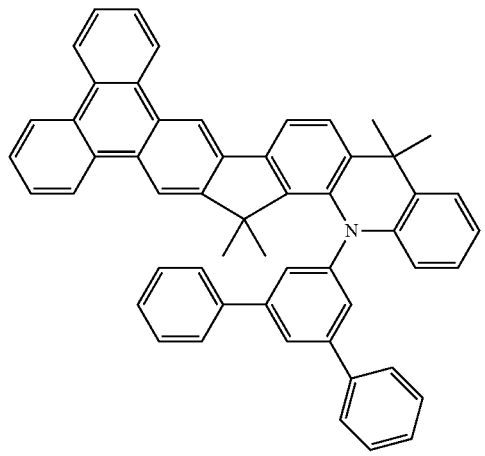
Compound 35
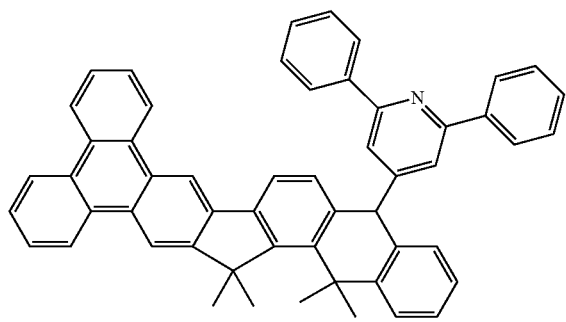
Compound 37
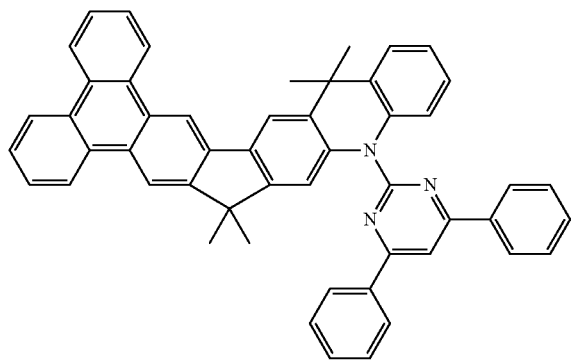
Compound 39
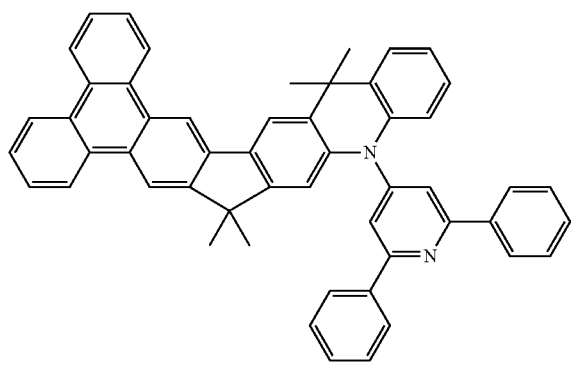
Compound 34
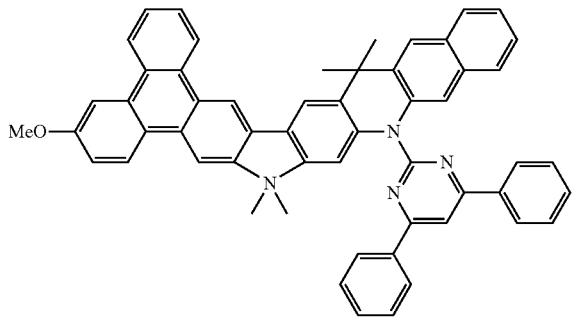
Compound 36
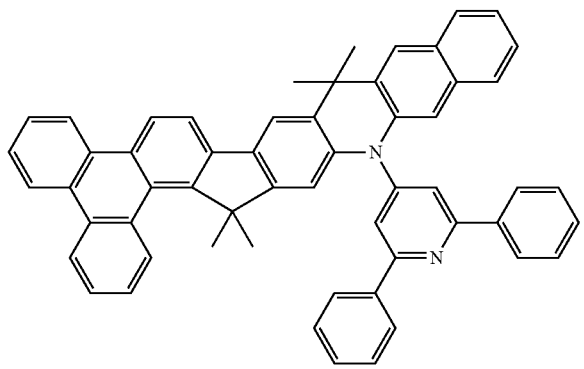
Compound 38
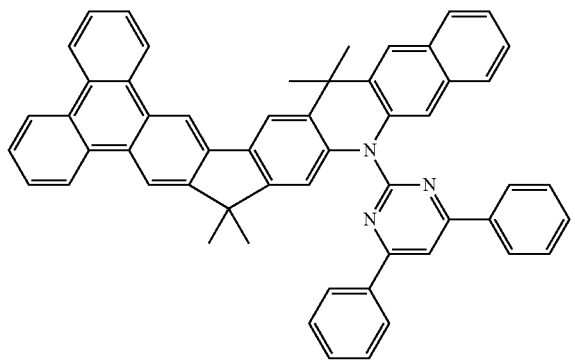
Compound 40
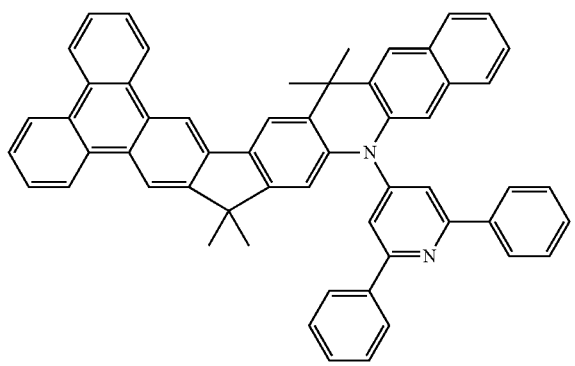

-continued
Compound 41
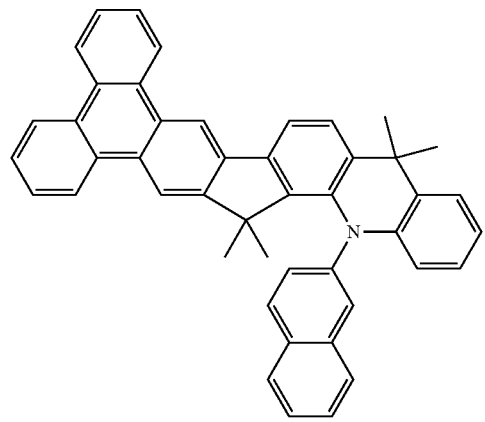
Compound 42
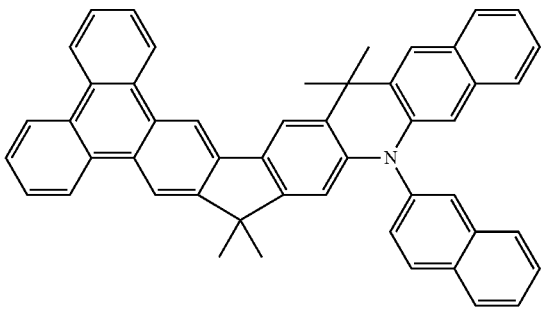
Compound 43
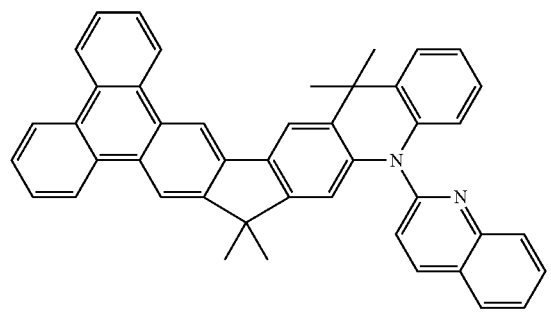
Compound 44
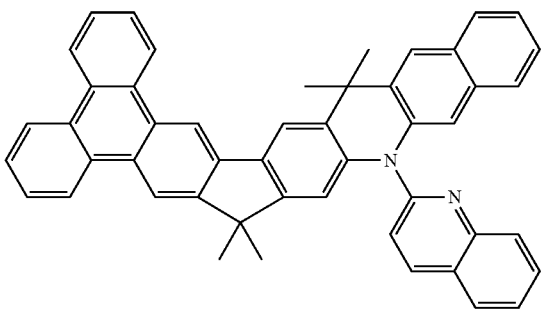
Compound 45
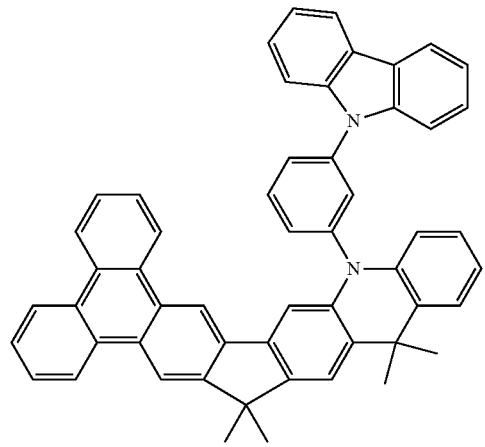
Compound 46
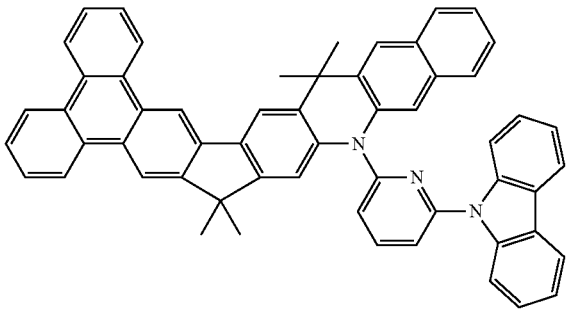
Compound 47
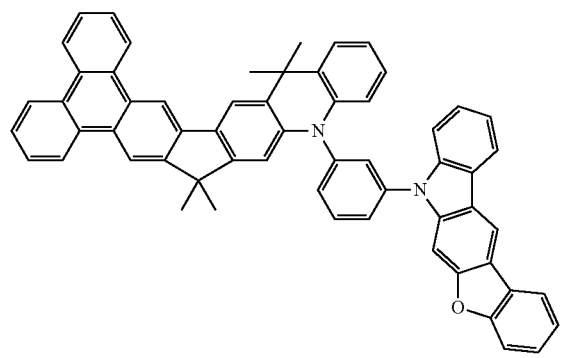
Compound 48
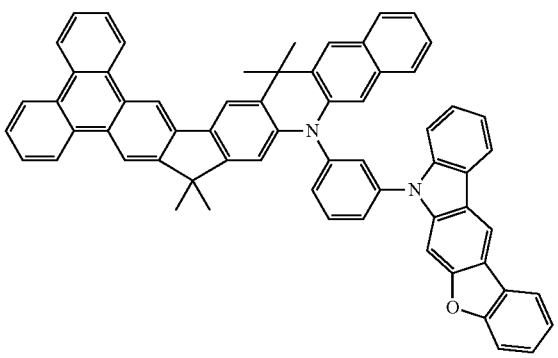

-continued
Compound 49
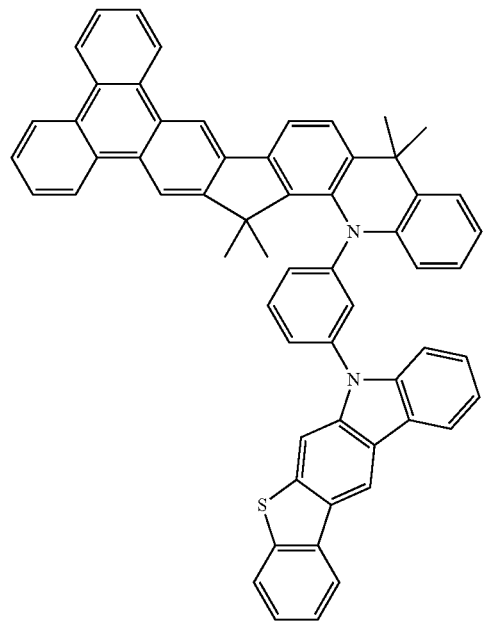
Compound 50
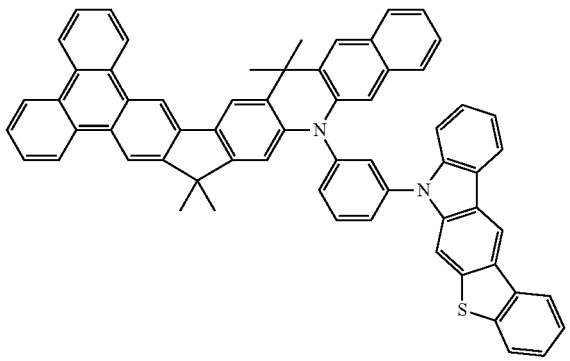
Compound 51
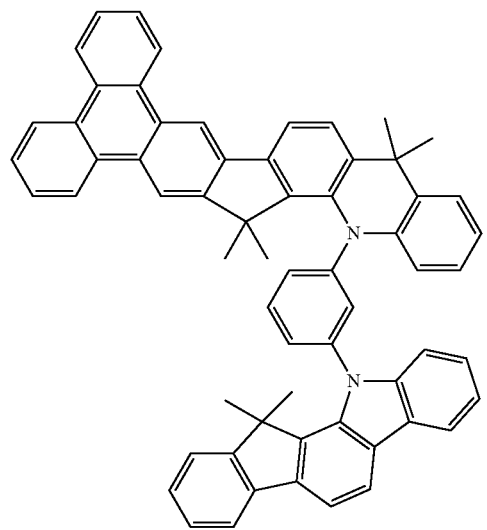
Compound 52
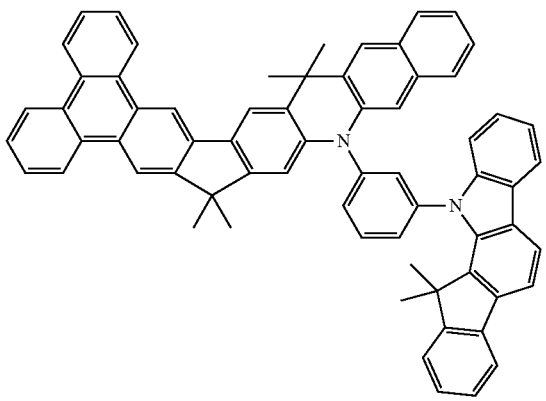

-continued
Compound 61
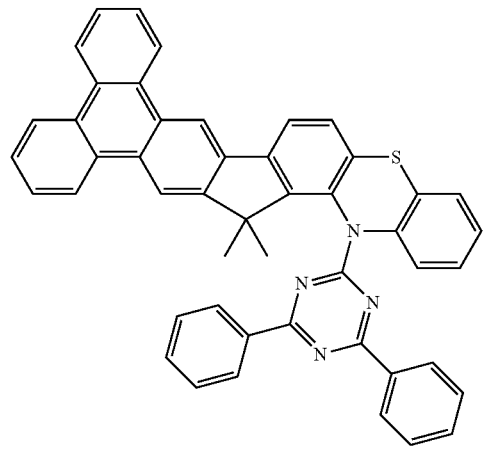
Compound 62
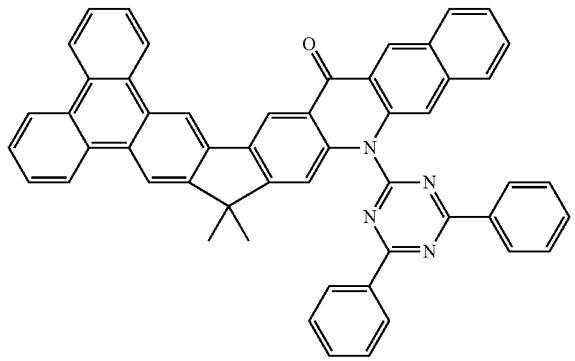
Compound 63
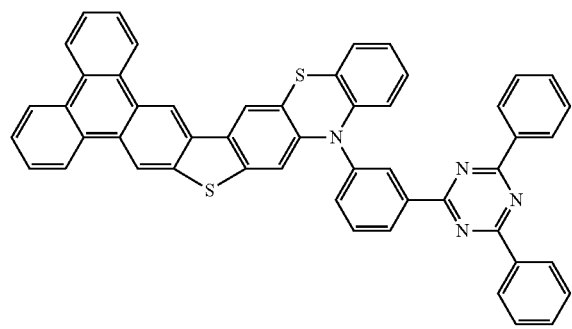
Compound 64
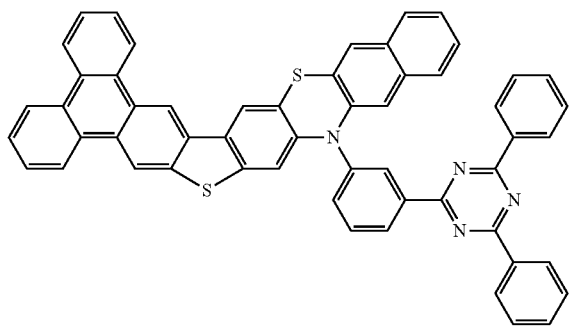
Compound 65
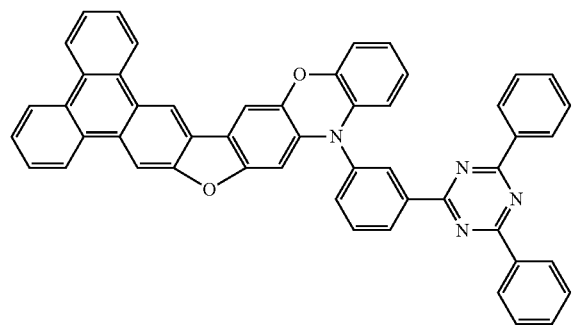
Compound 66
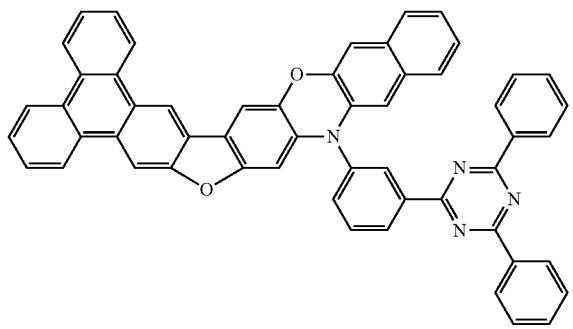
Compound 67
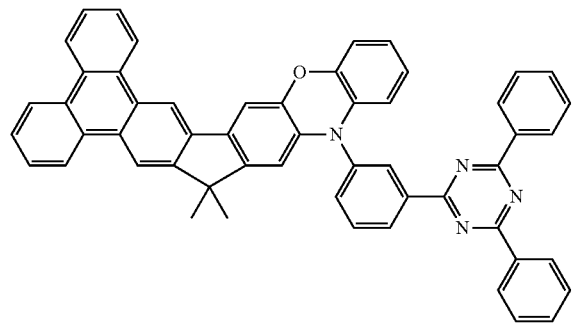
Compound 68
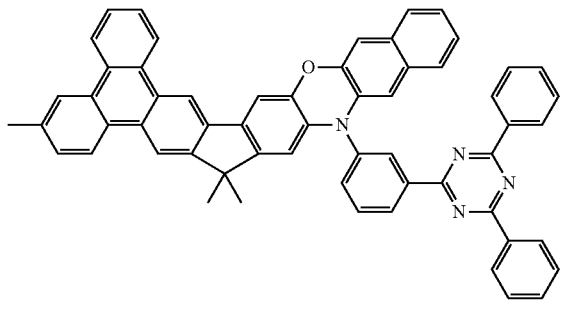

-continued
Compound 69
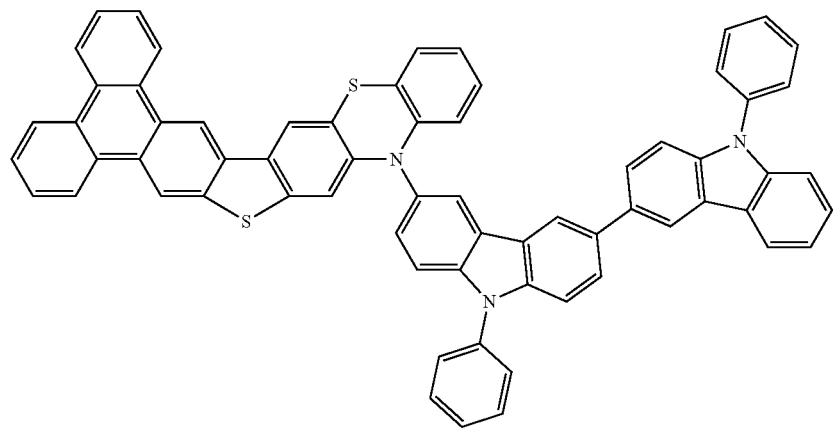
Compound 70
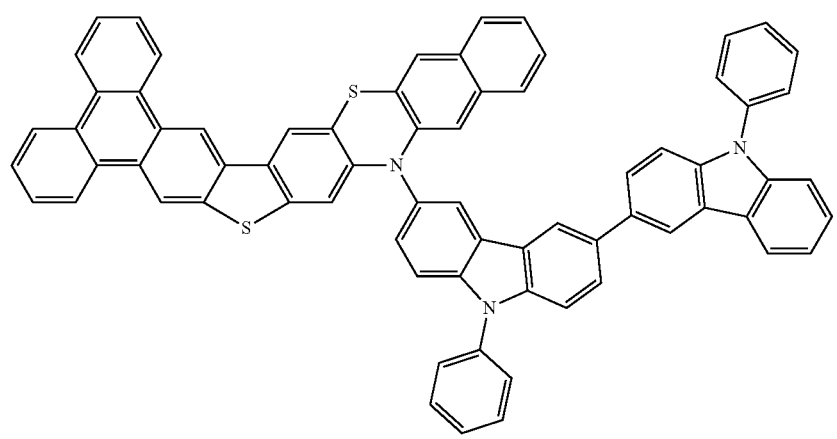
Compound 71
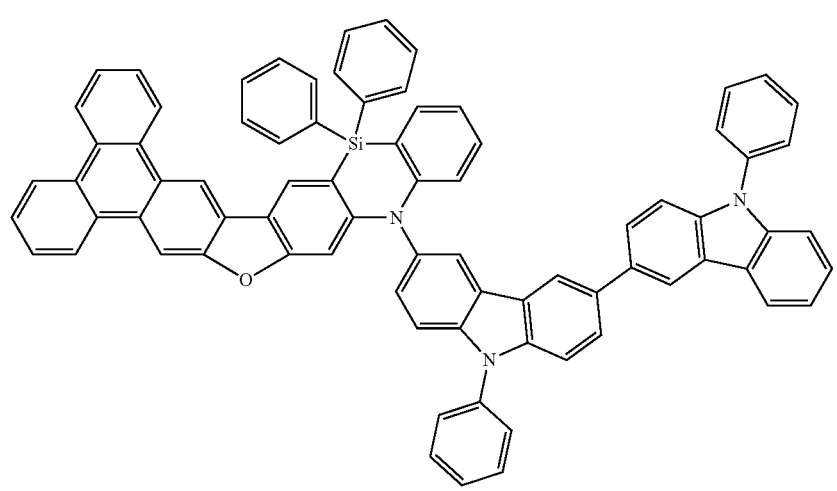

Compound 72
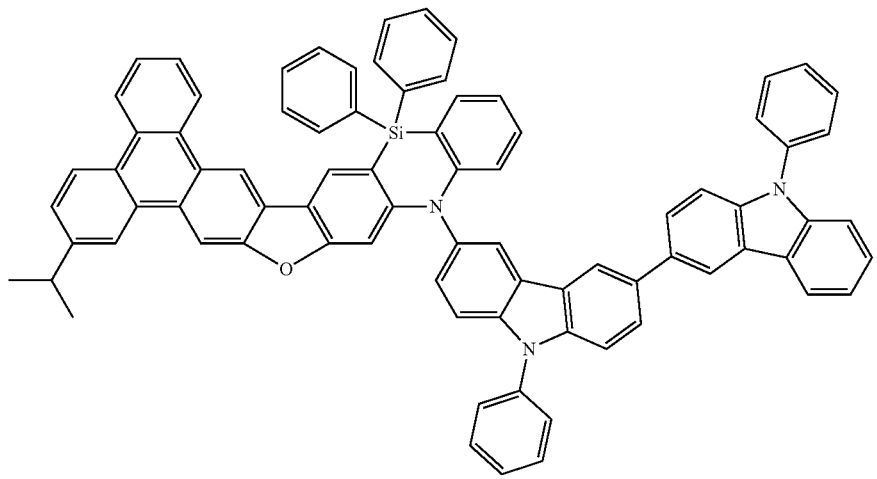
Compound 73
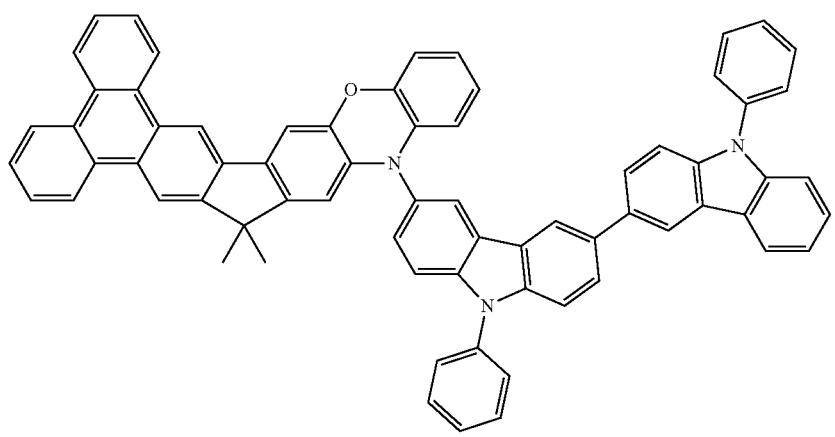
Compound 74
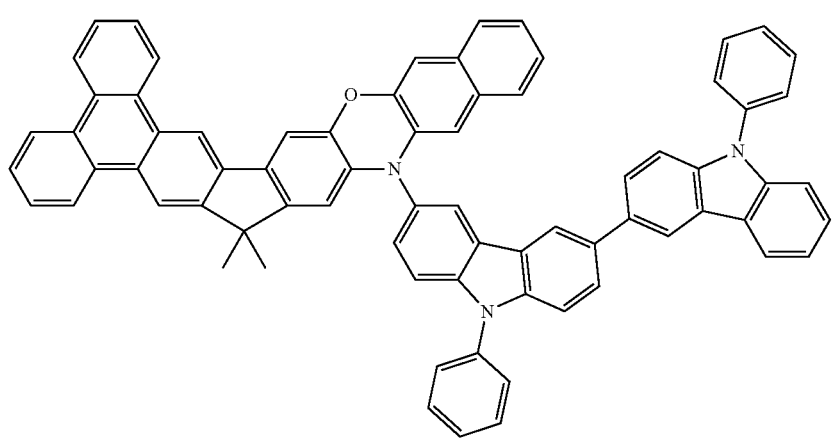

-continued
Compound 75
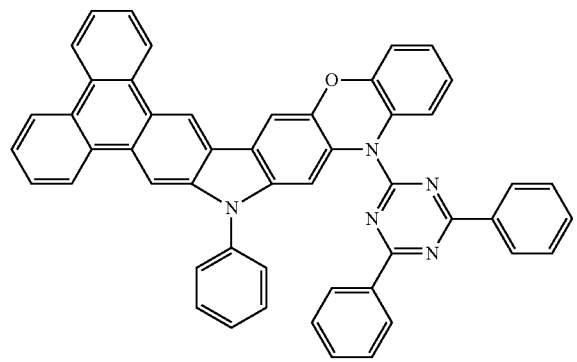
Compound 76
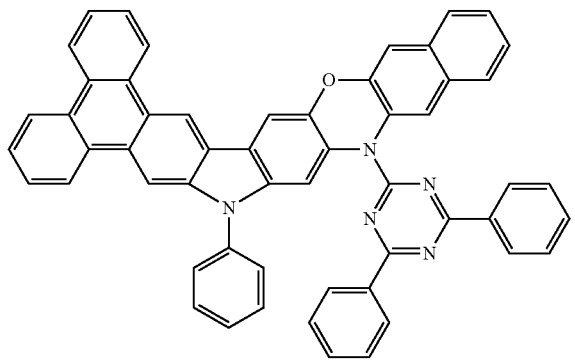
Compound 77
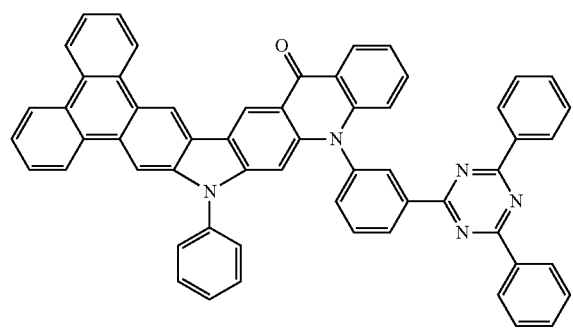
Compound 78
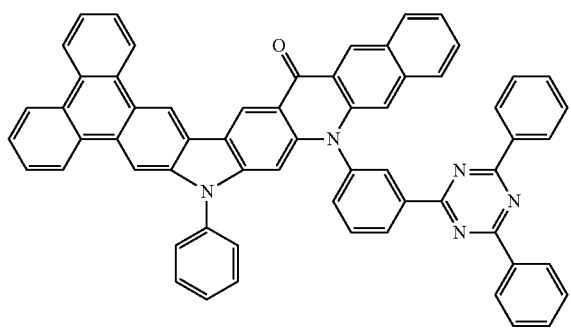
Compound 79
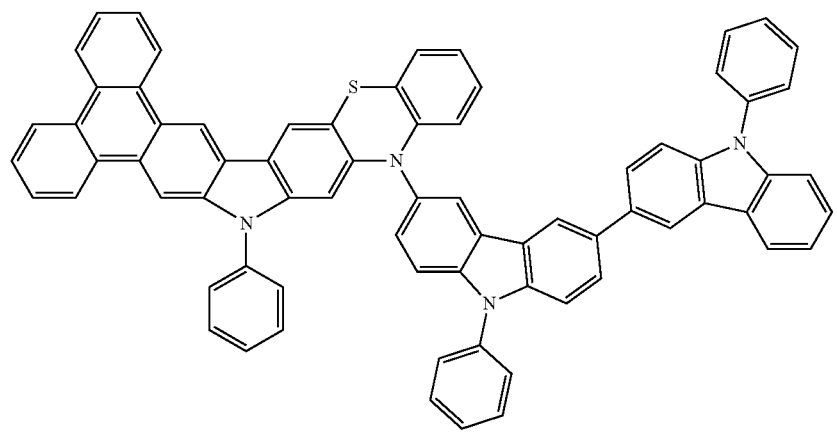
Compound 80
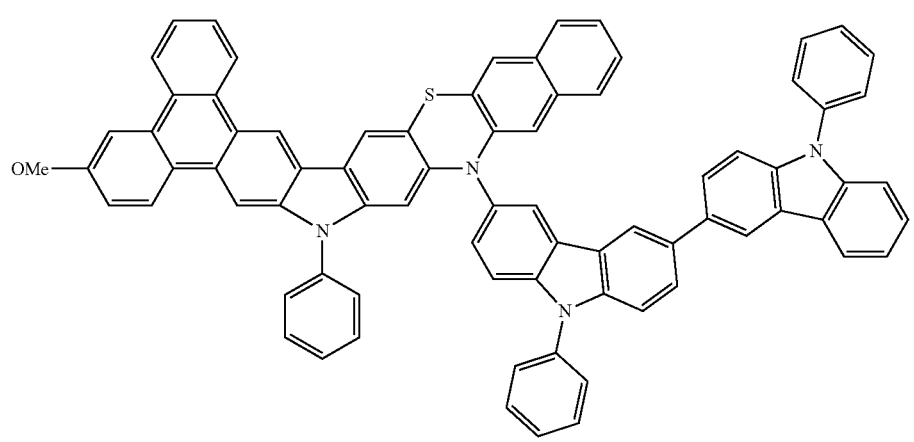

-continued
Compound 81
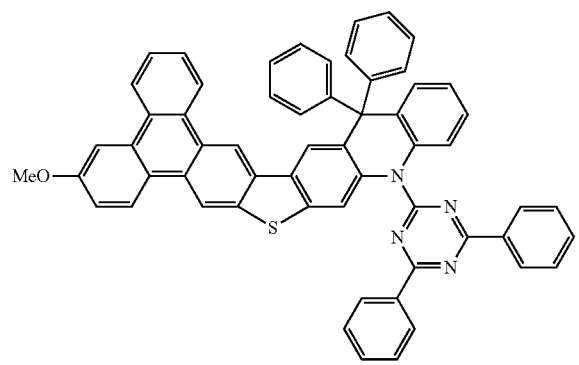
Compound 82
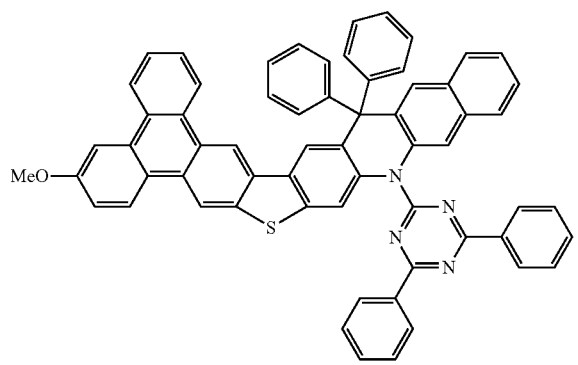
Compound 83
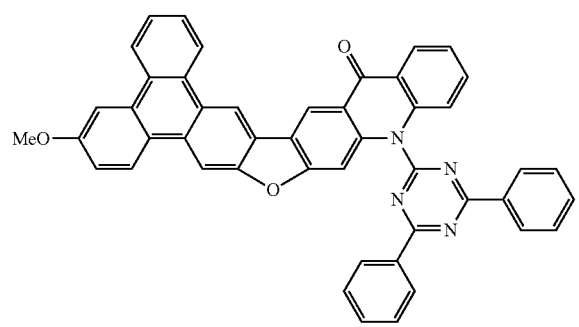
Compound 84
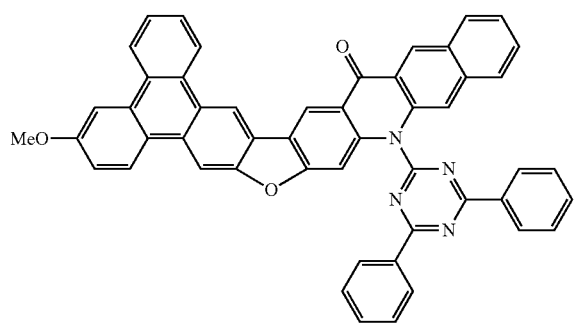
Compound 85
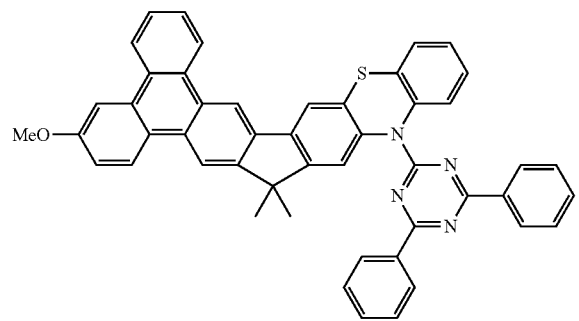
Compound 86
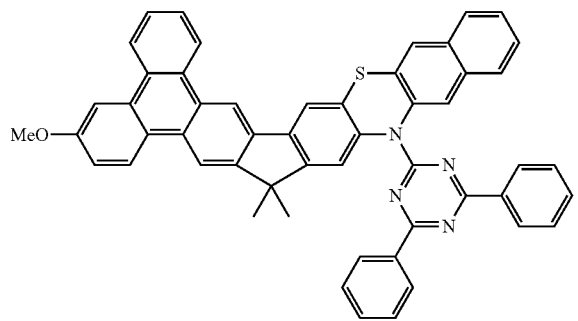
Compound 87
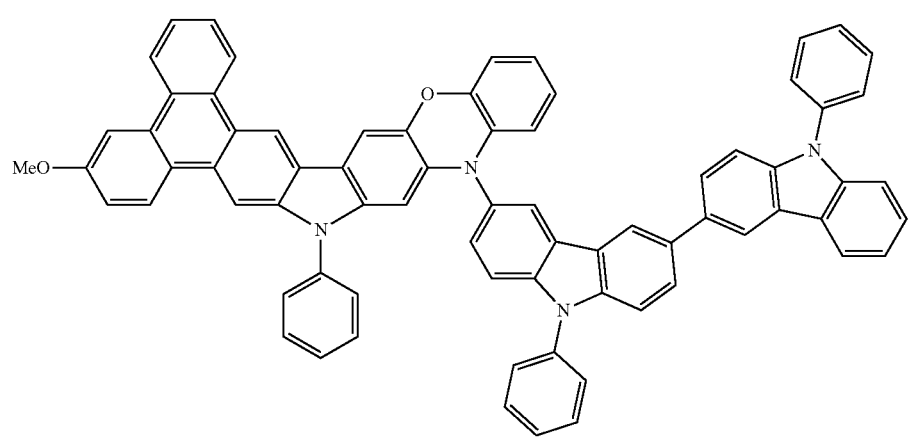

-continued
Compound 88
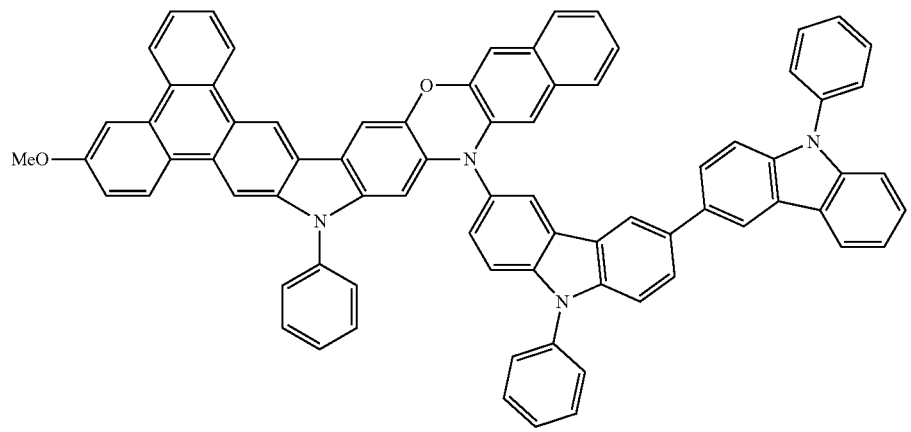
Compound 89
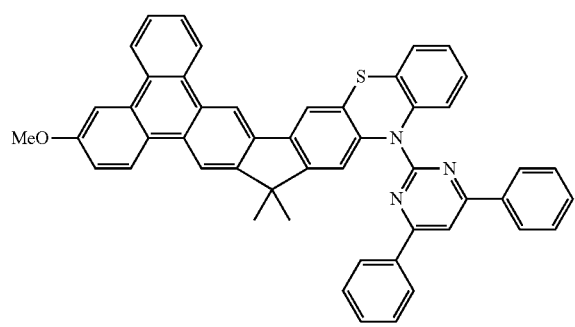
Compound 90
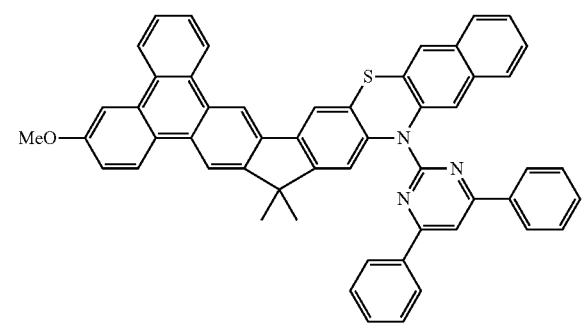
Compound 91
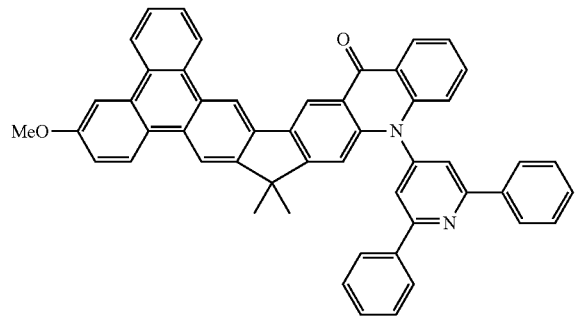
Compound 92
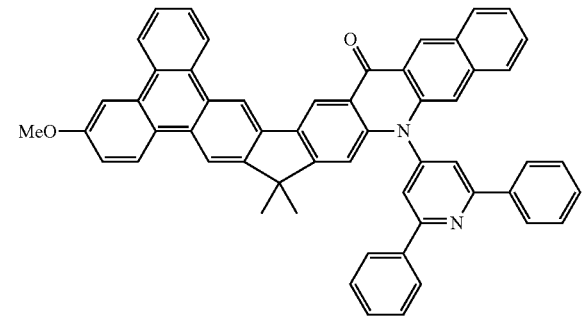
Compound 93
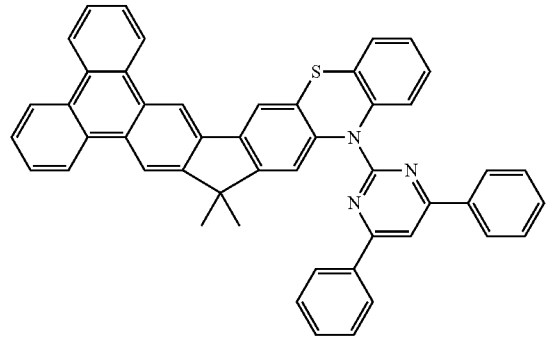
Compound 94
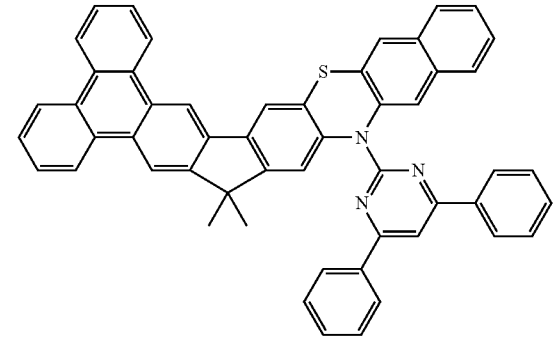

-continued
Compound 95
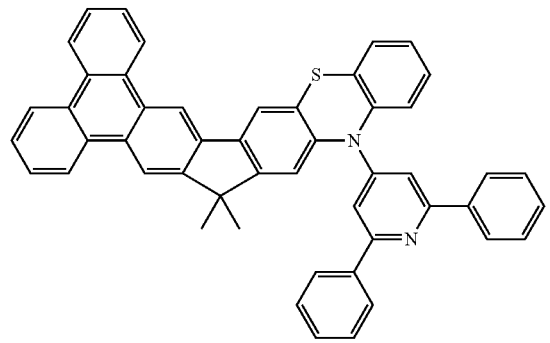
Compound 96
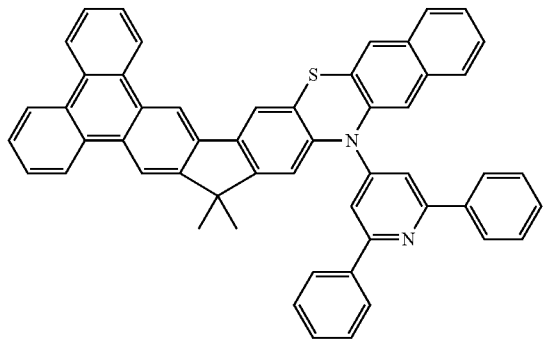
Compound 97
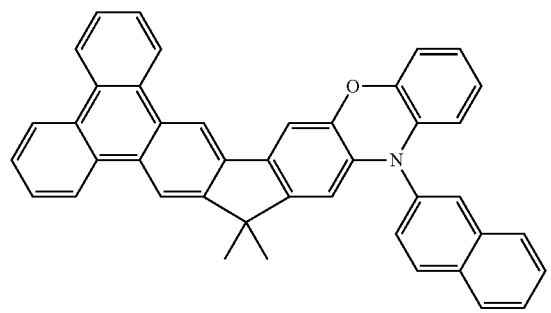
Compound 98
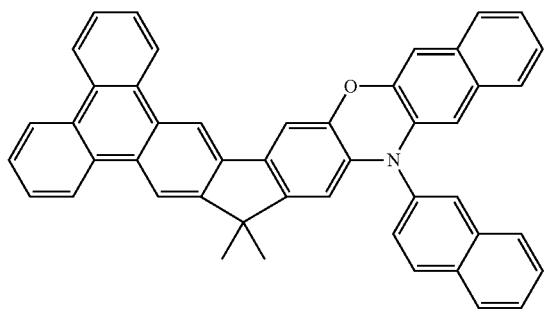
Compound 99
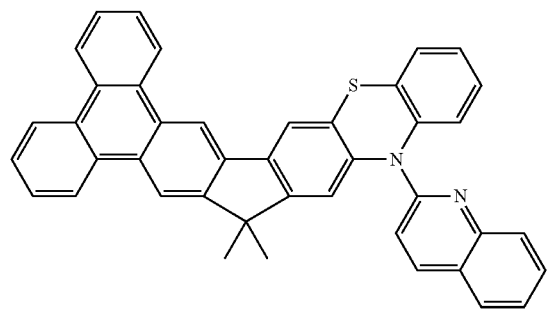
Compound 100
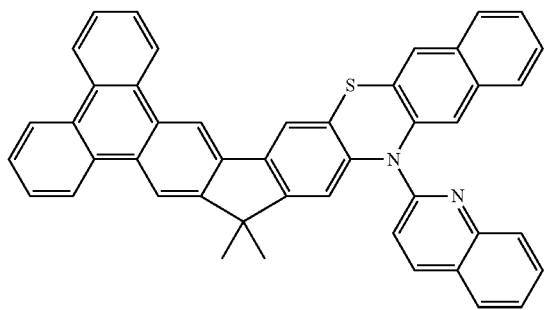
Compound 101
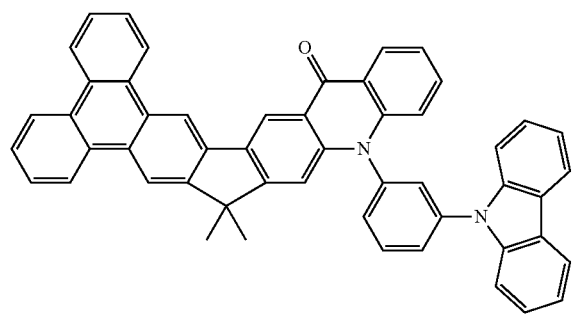
Compound 102
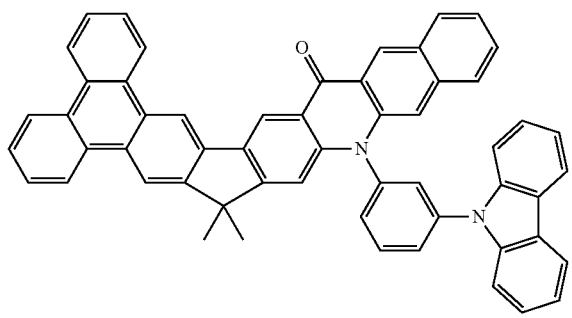

-continued
Compound 103
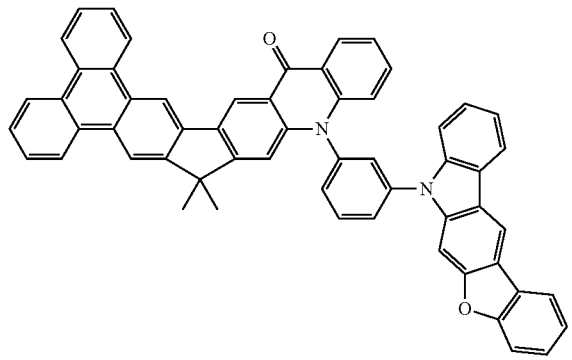
Compound 104
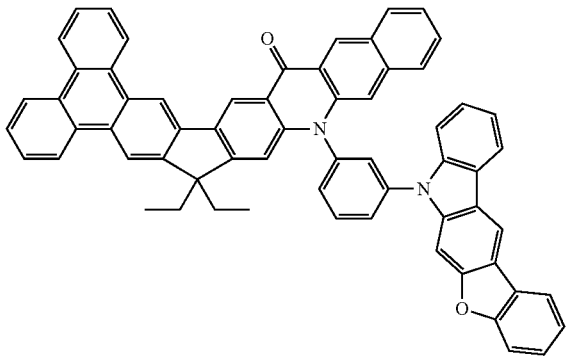
Compound 105
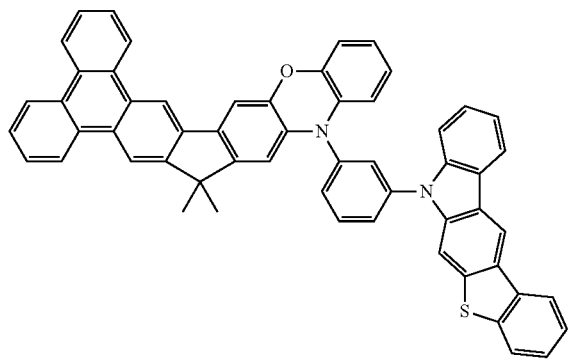
Compound 106
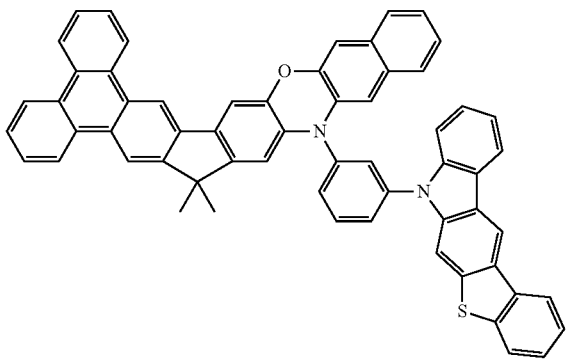
Compound 107
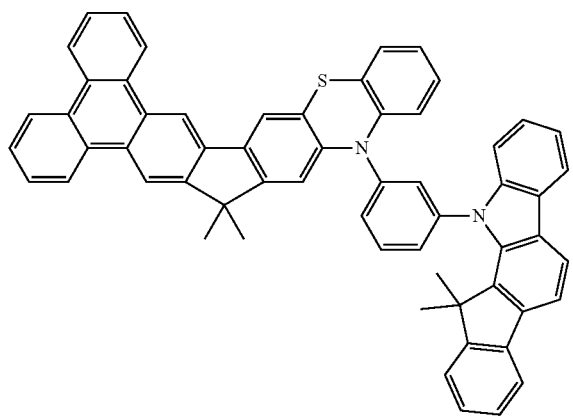
Compound 108
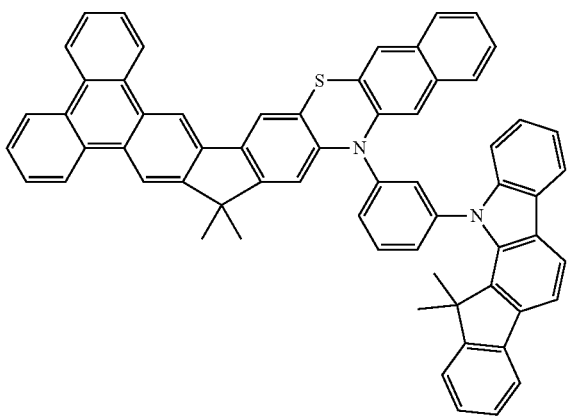
Compound 109
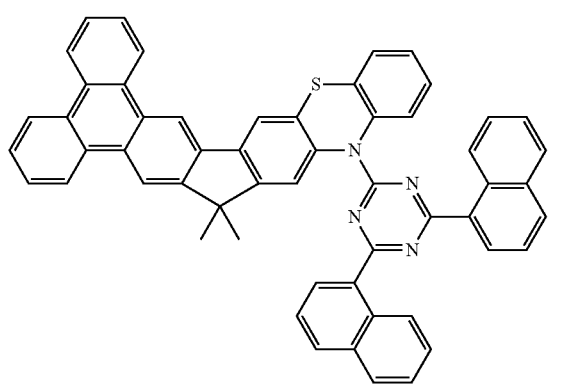
Compound 110
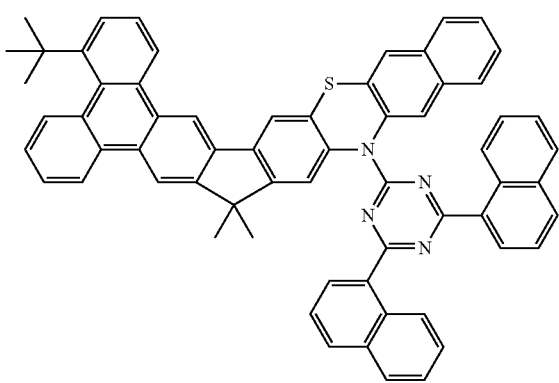

-continued
Compound 111
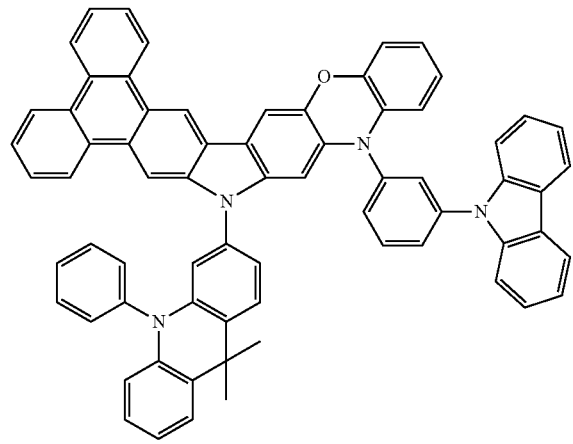
Compound 112
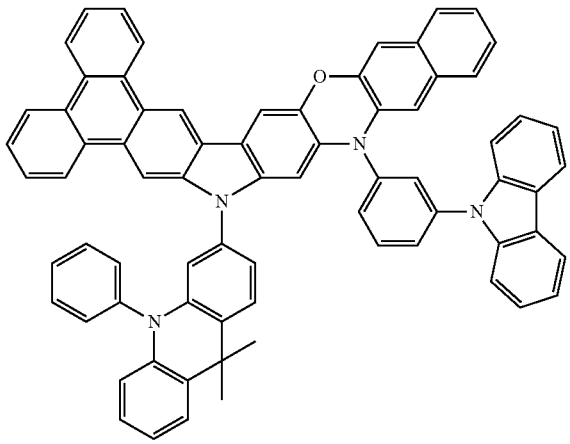
Compound 113
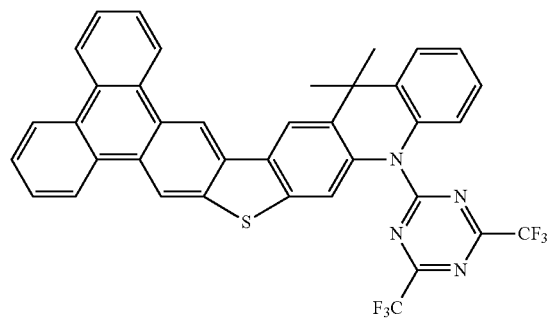
Compound 114
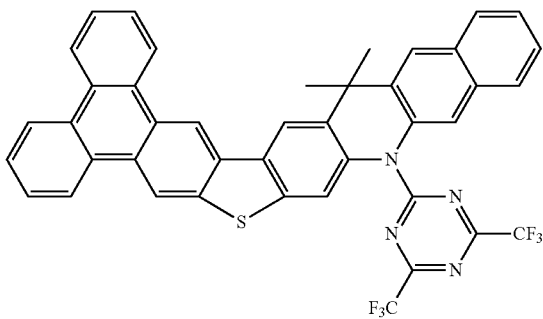
Compound 115
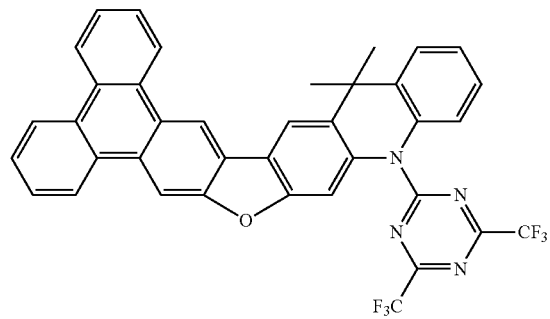
Compound 116
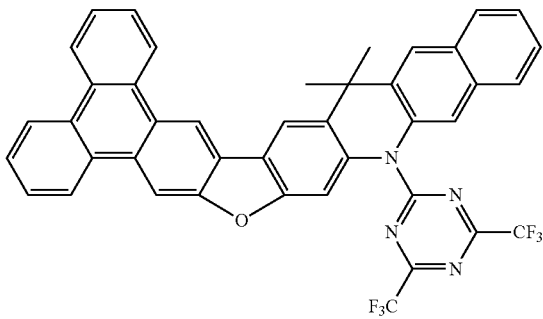
Compound 117
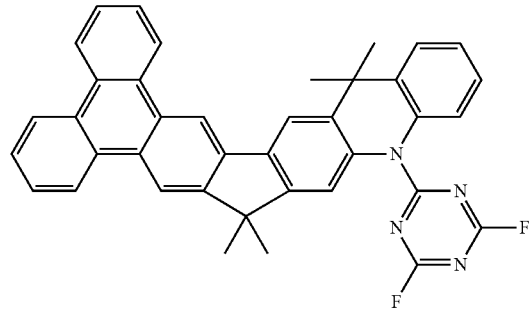
Compound 118
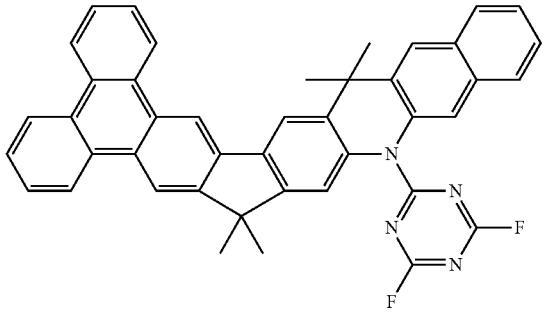

-continued
Compound 119
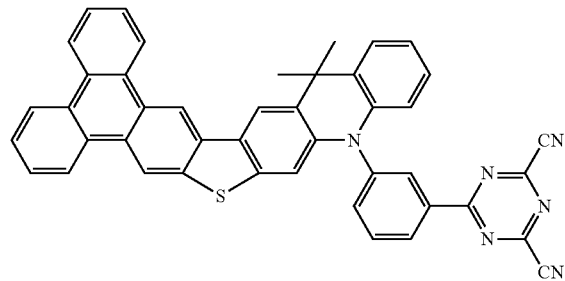
Compound 120
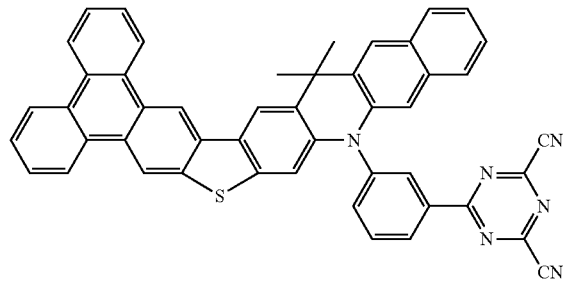
Compound 121
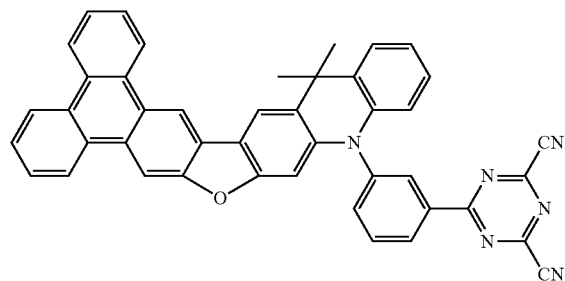
Compound 122
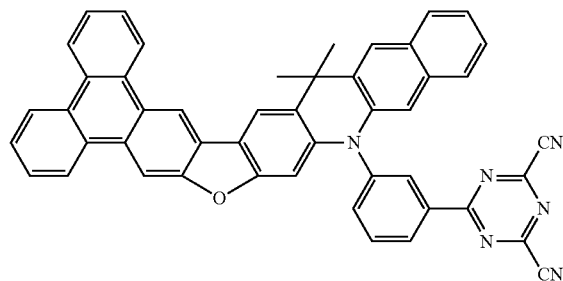
Compound 123
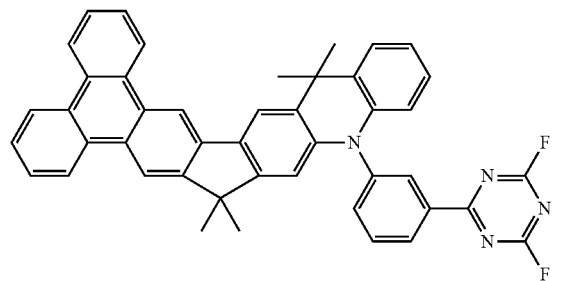
Compound 124
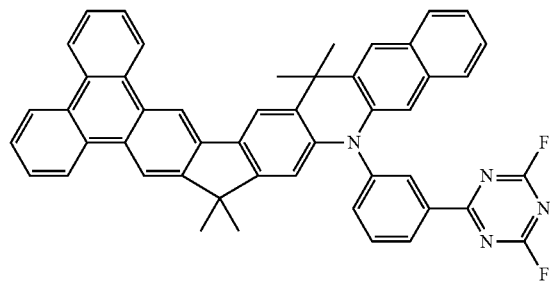
Compound 125
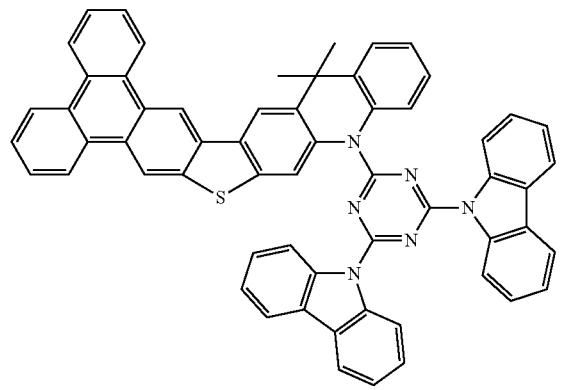
Compound 126
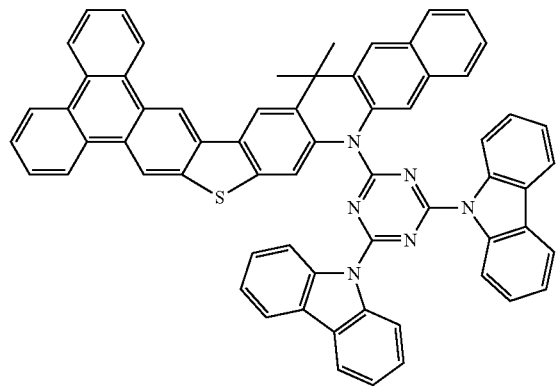

-continued
Compound 127
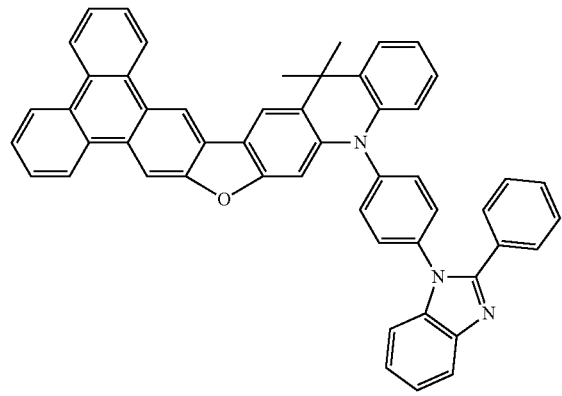
Compound 128
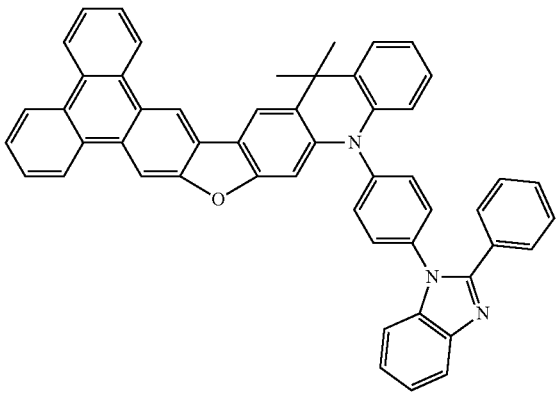
Compound 129
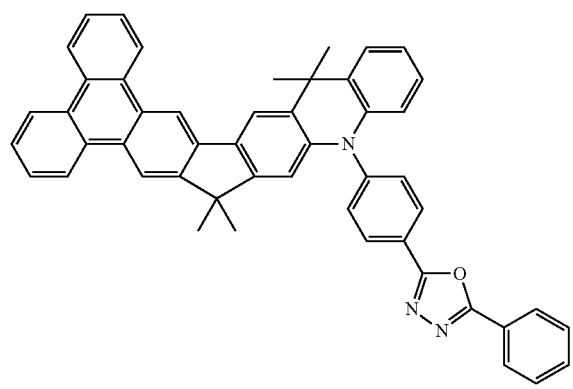
Compound 130
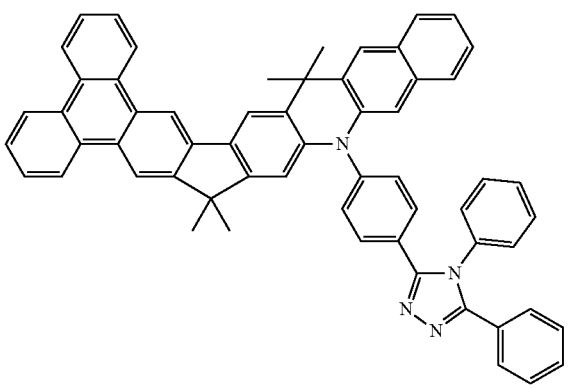
Compound 131
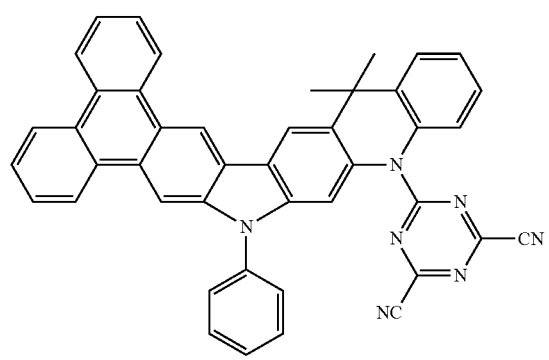
Compound 132
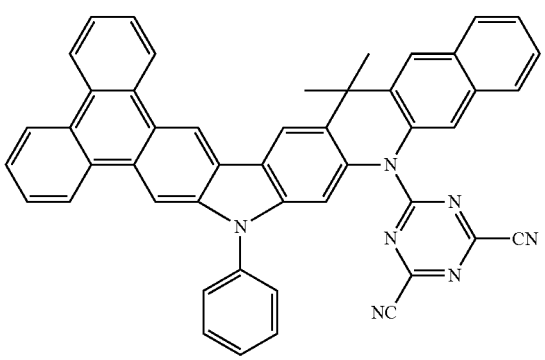
Compound 133
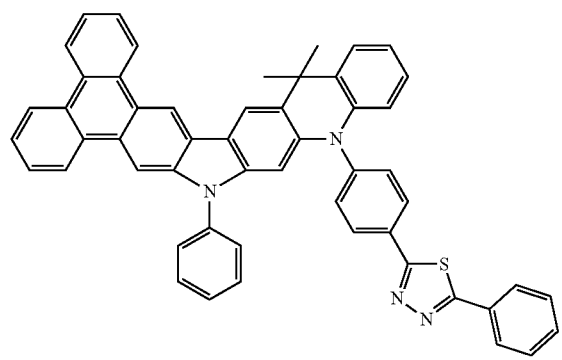
Compound 134

-continued
Compound 135
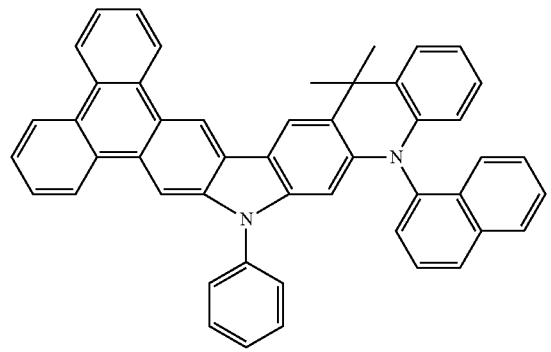
Compound 136
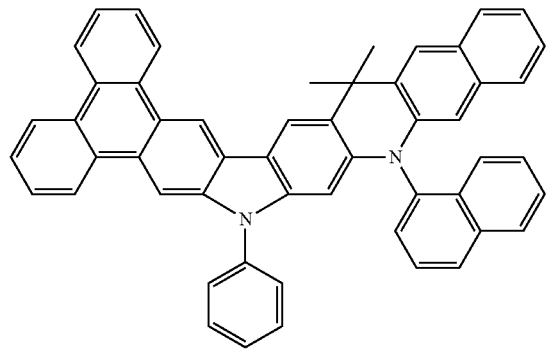
Compound 137
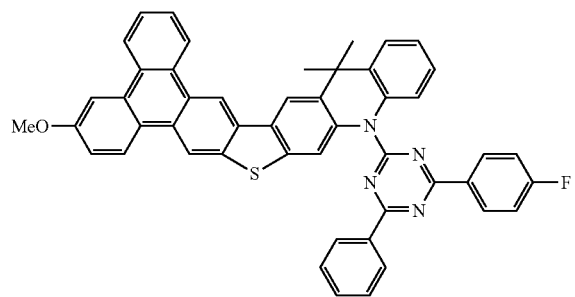
Compound 138
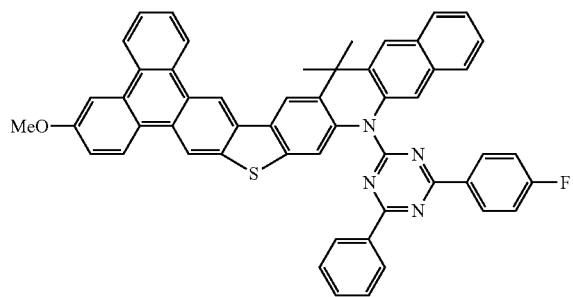
Compound 139
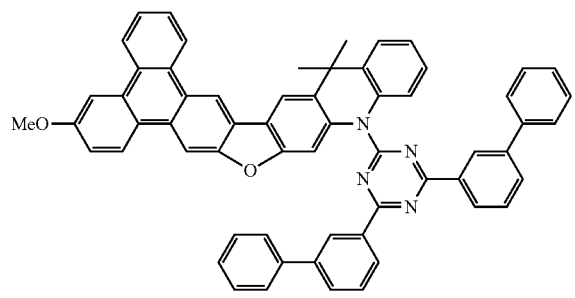
Compound 140
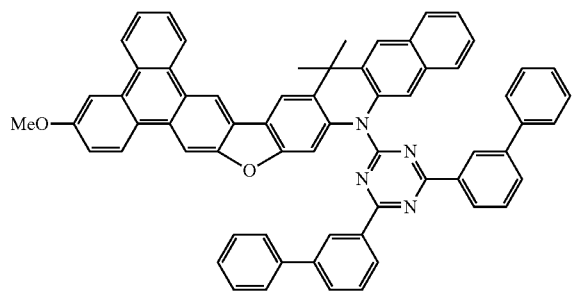
Compound 141
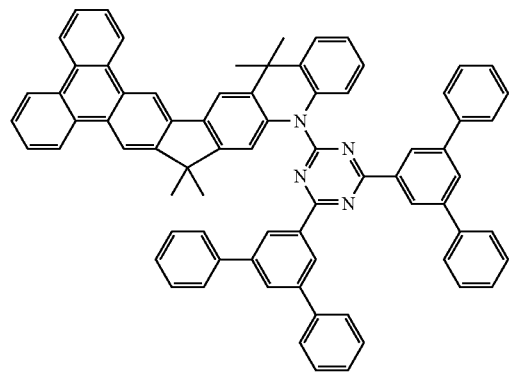
Compound 142
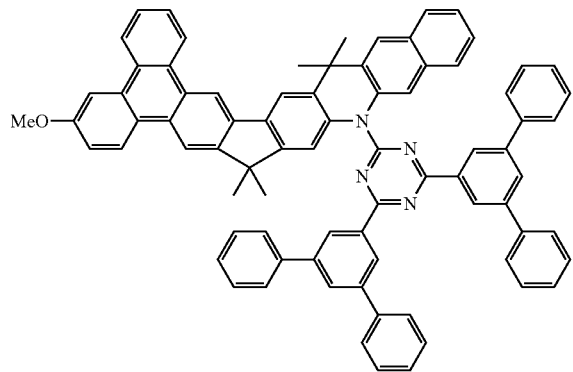

-continued
Compound 143
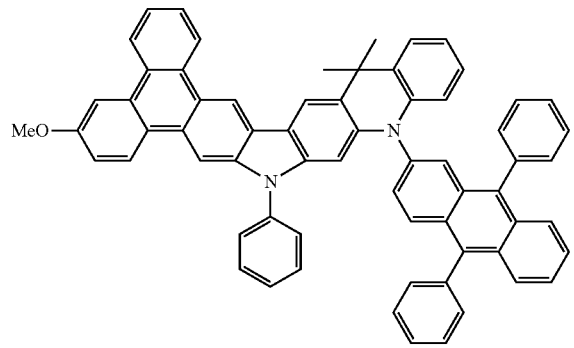
Compound 144
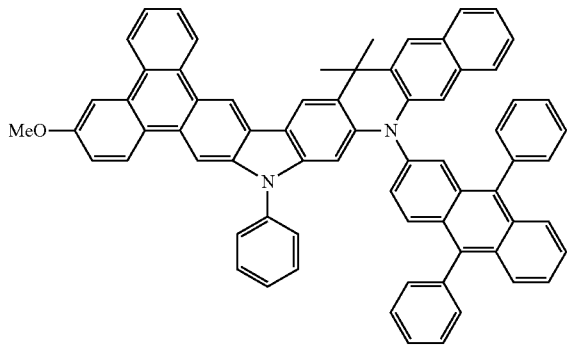
Compound 145
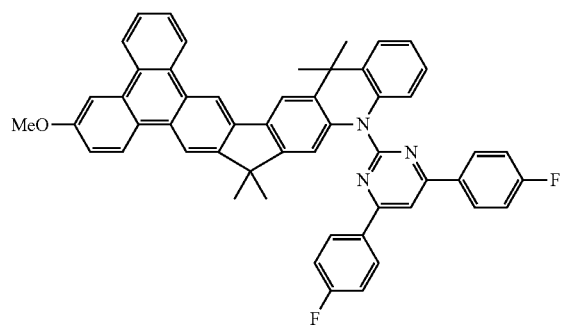
Compound 146
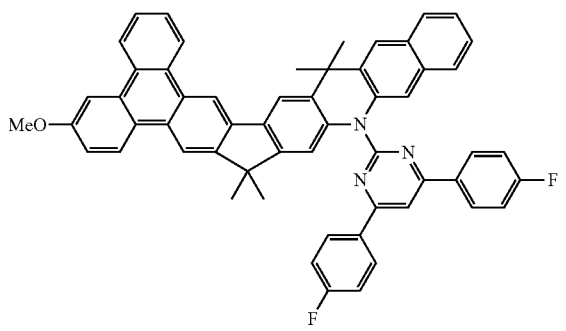
Compound 147
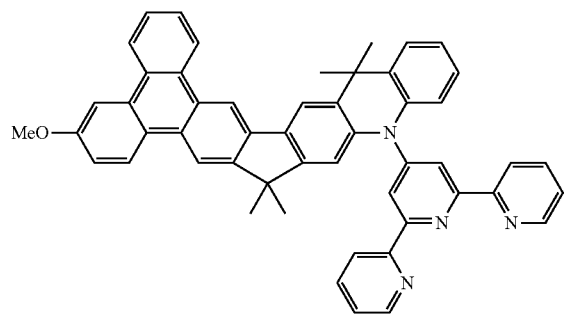
Compound 148
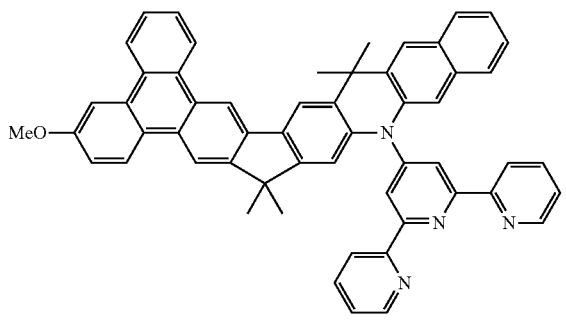
Compound 149
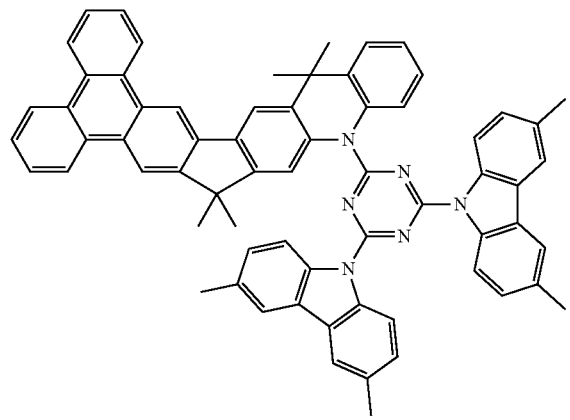
Compound 150
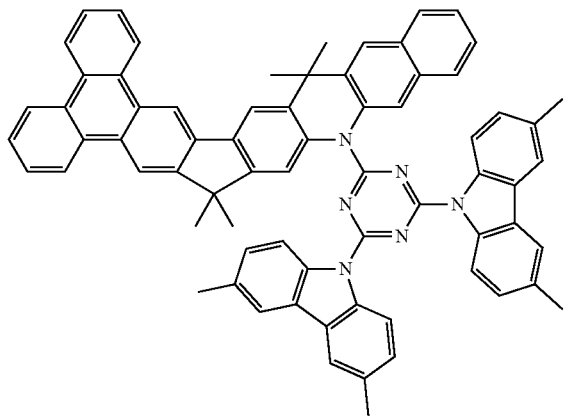

-continued
Compound 151
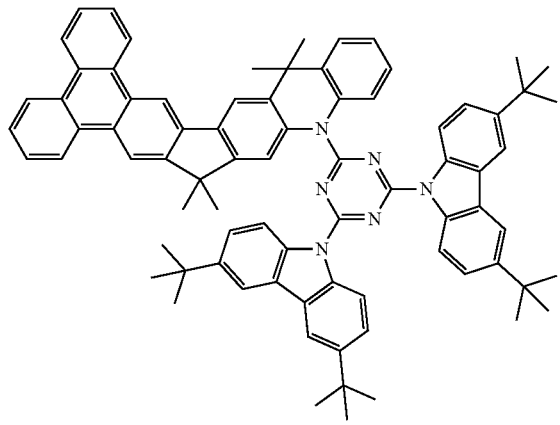
Compound 152
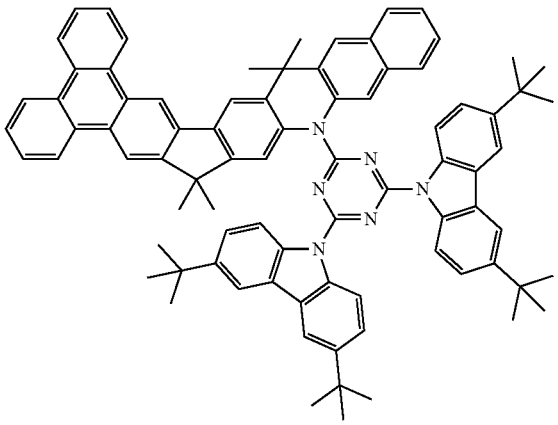
Compound 153
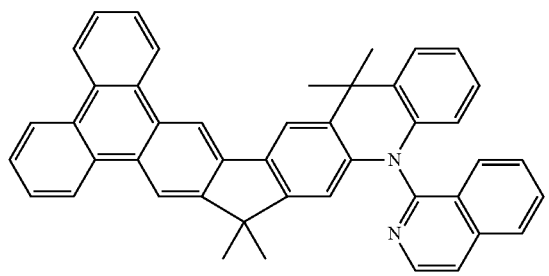
Compound 154
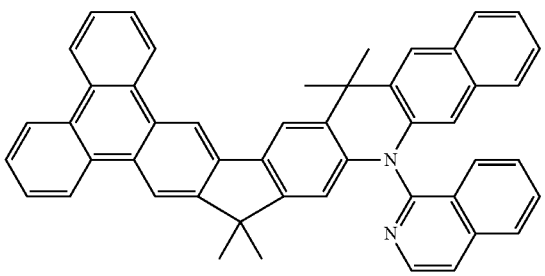
Compound 155
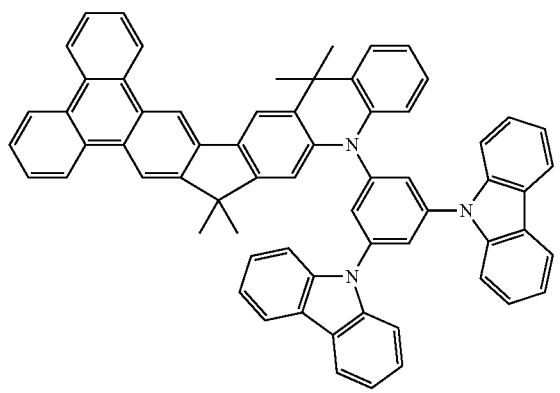
Compound 156
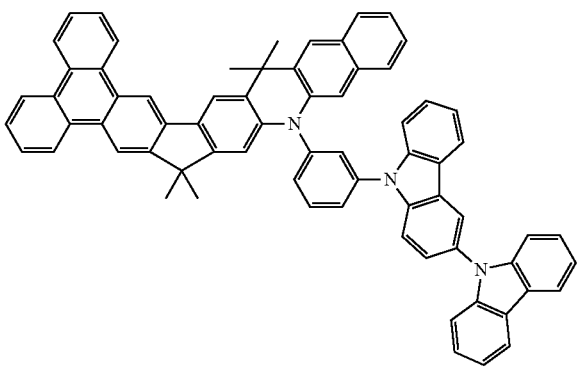
Compound 157
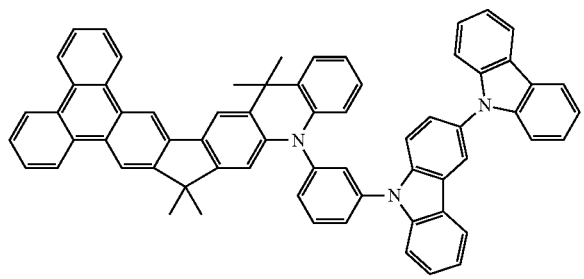
Compound 158
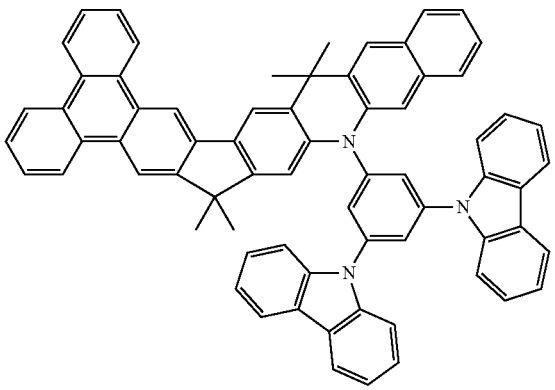

-continued
Compound 159
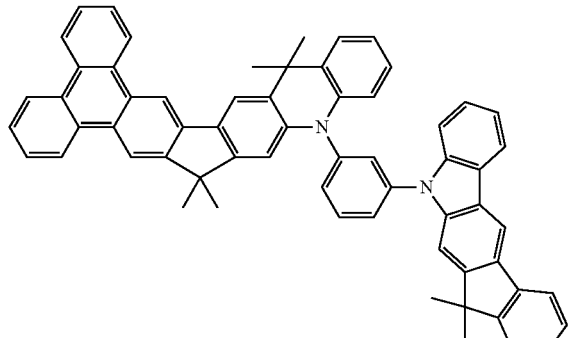
Compound 160
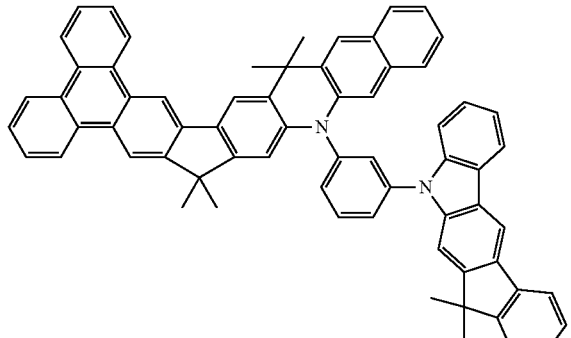
Compound 161
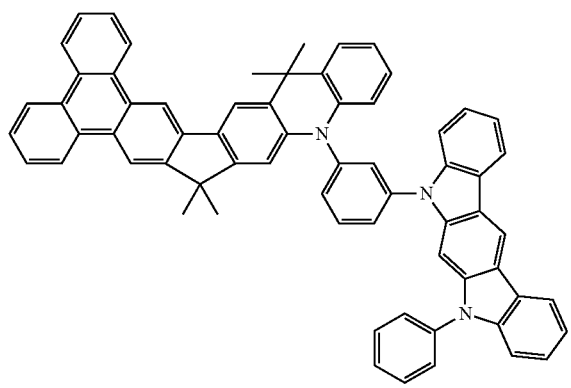
Compound 162
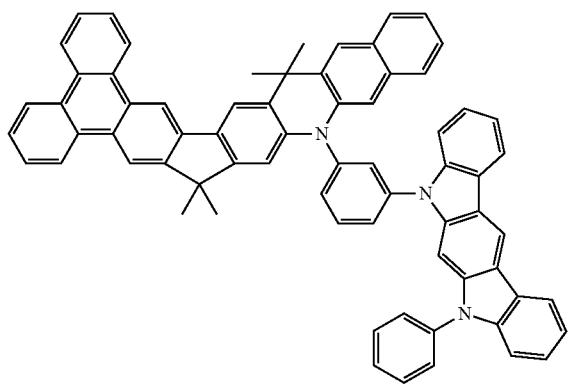
Compound 163
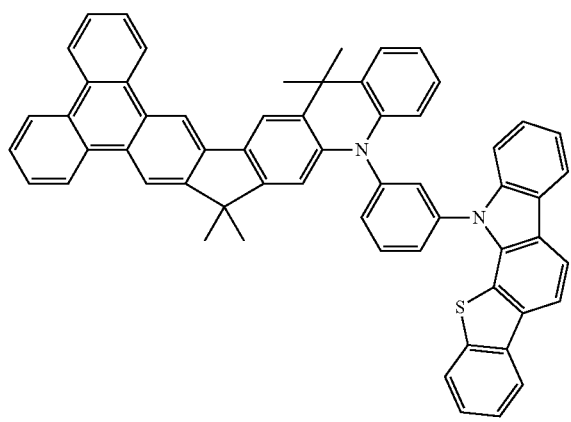
Compound 164
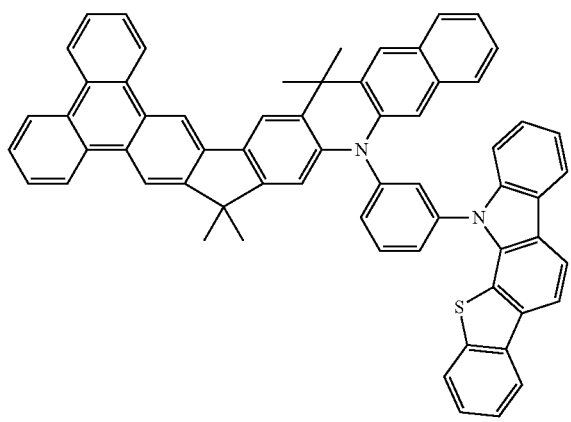
Compound 165
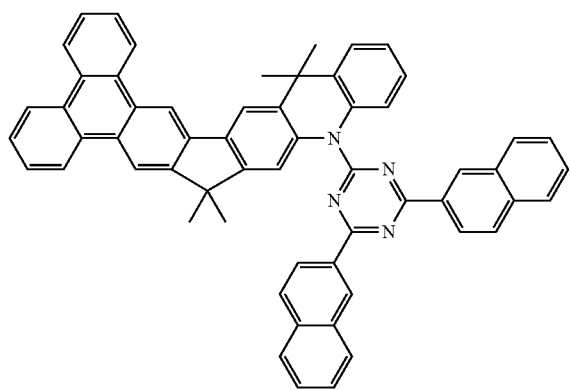
Compound 166
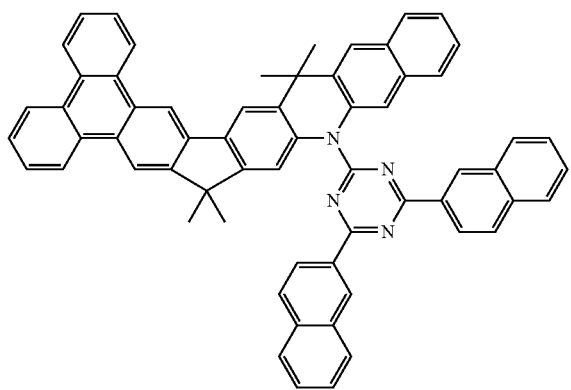

-continued
Compound 167
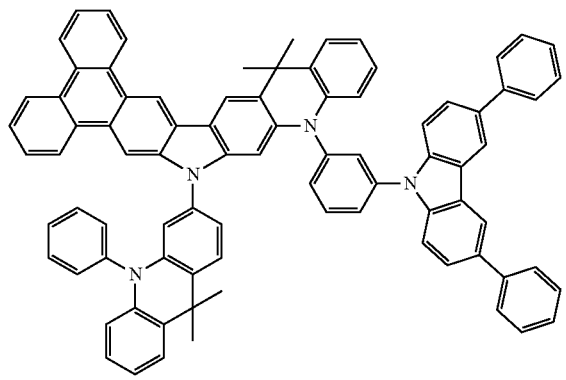
Compound 168
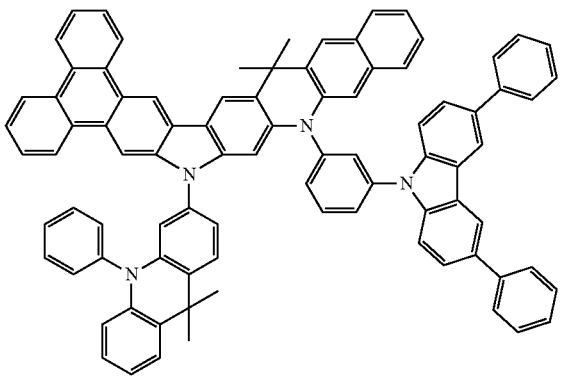
Compound 169
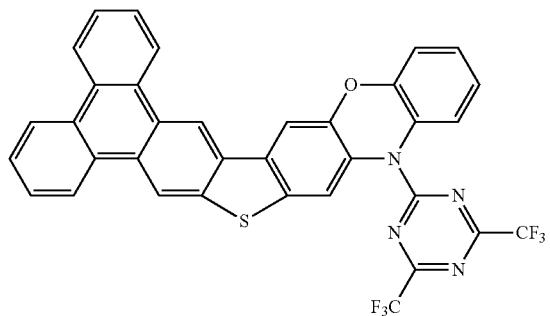
Compound 170
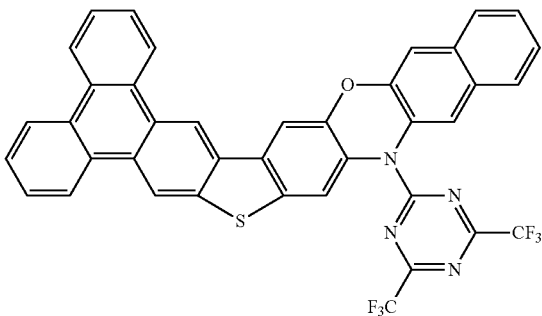
Compound 171
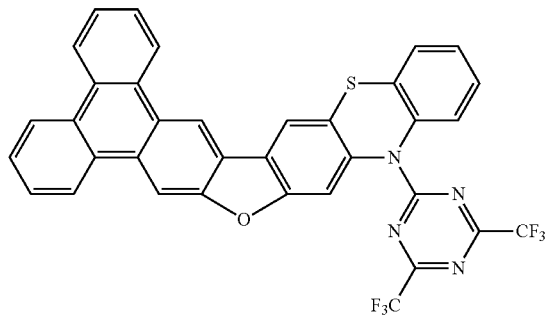
Compound 172
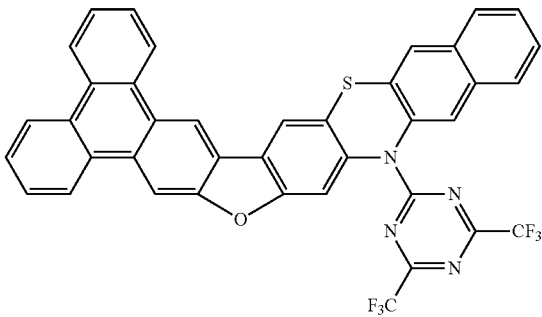
Compound 173
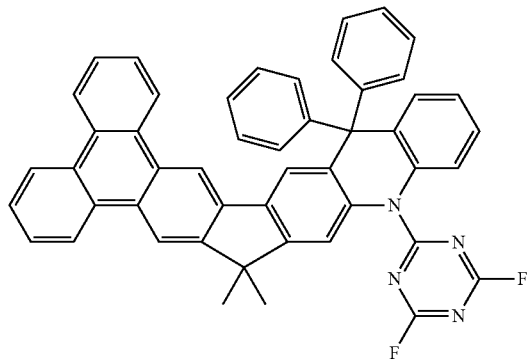
Compound 174
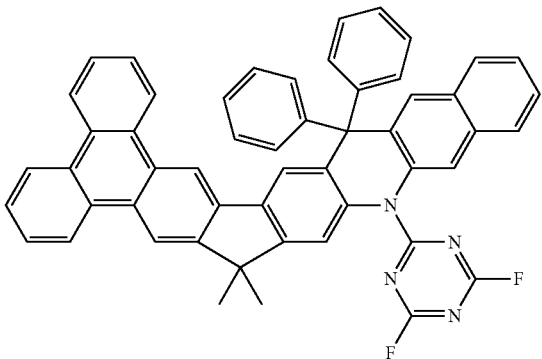

-continued
Compound 175
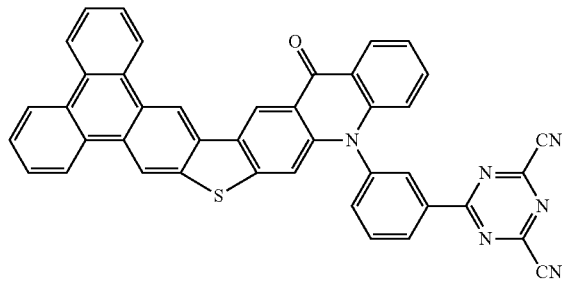
Compound 176
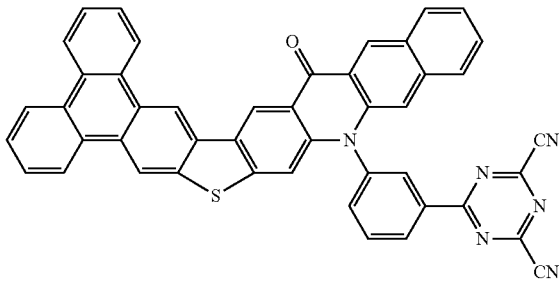
Compound 177
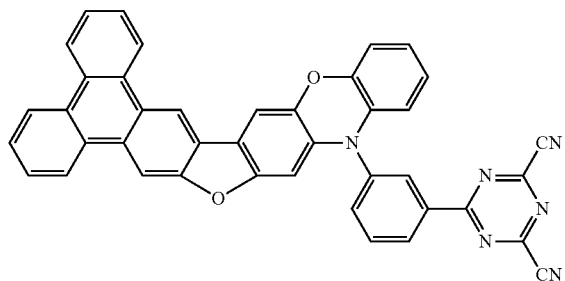
Compound 178
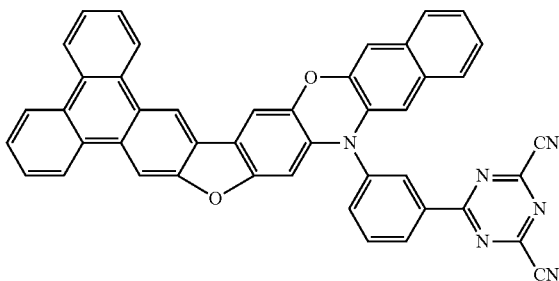
Compound 179
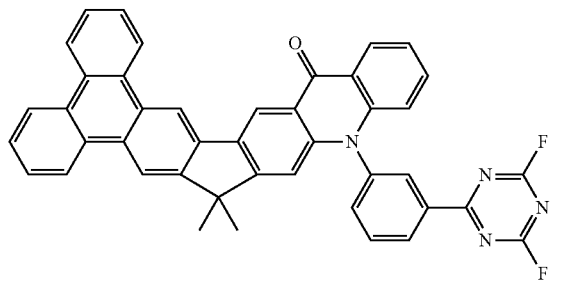
Compound 180
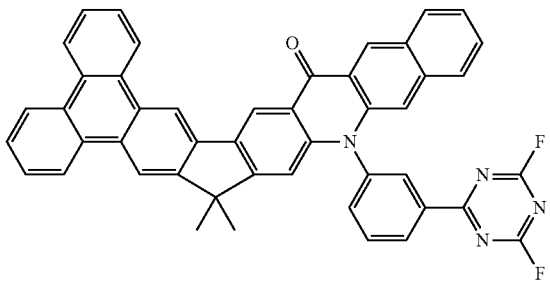
Compound 181
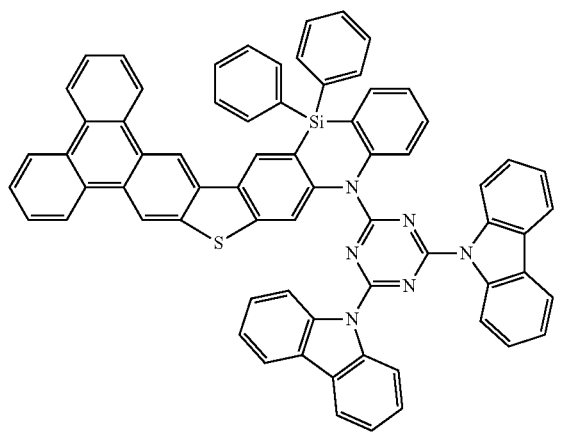
Compound 182
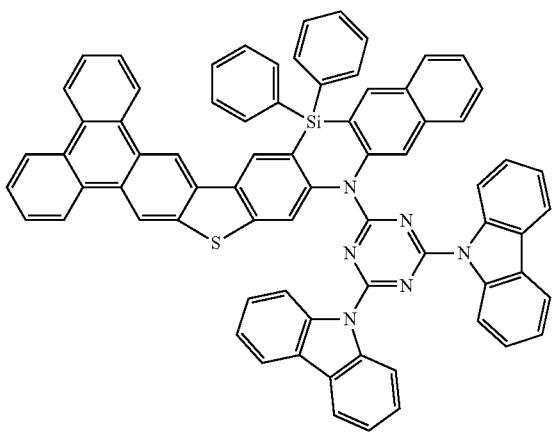

-continued
Compound 183
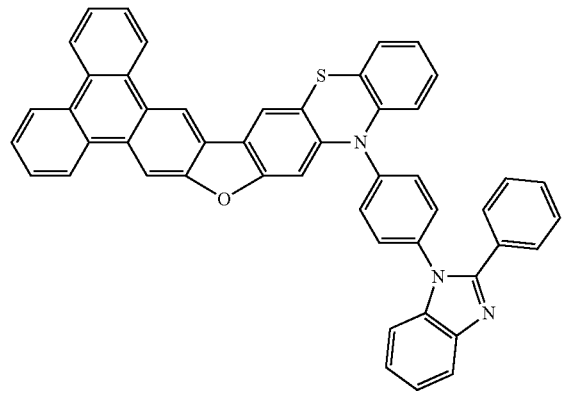
Compound 184
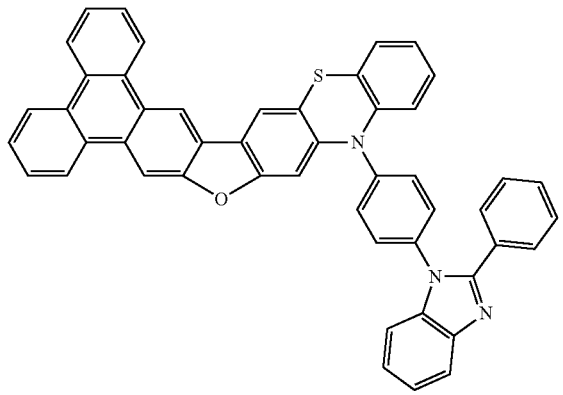
Compound 185
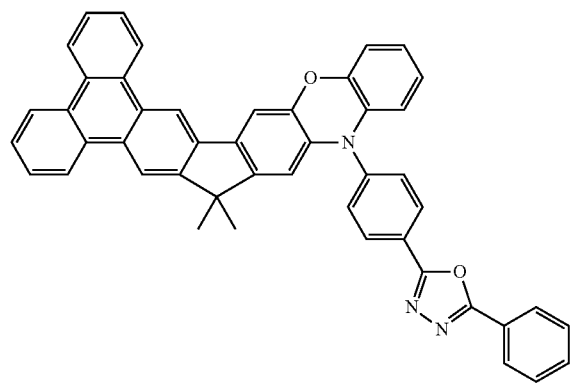
Compound 186
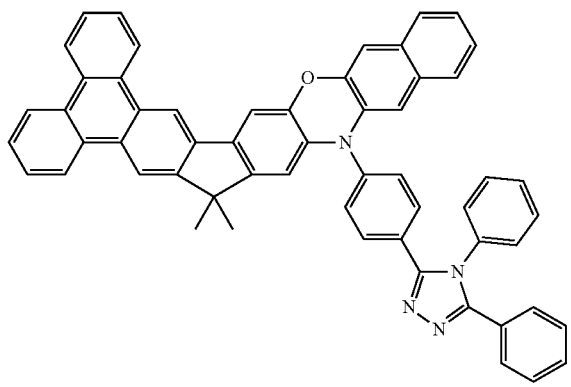
Compound 187
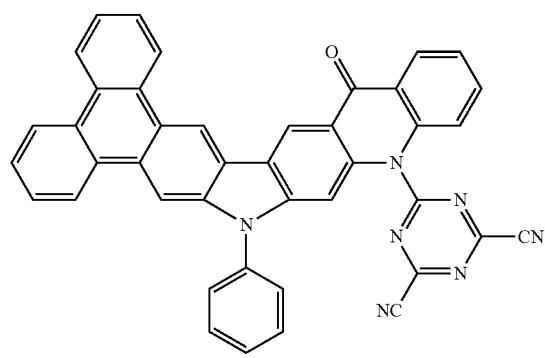
Compound 188
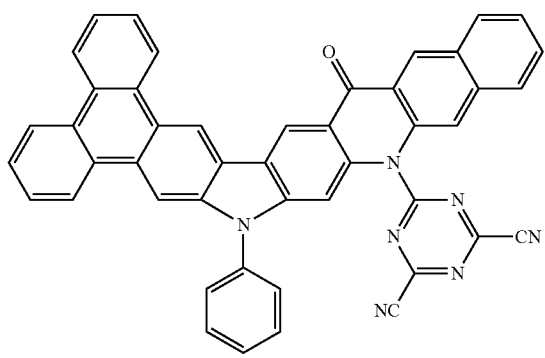
Compound 189
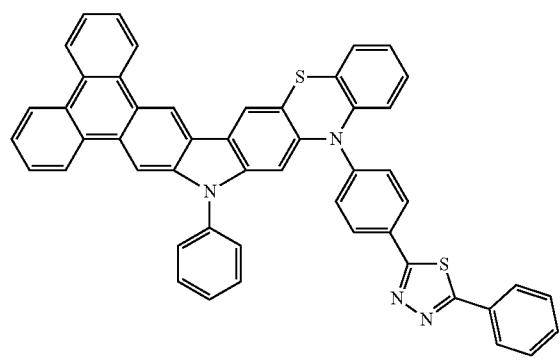
Compound 190
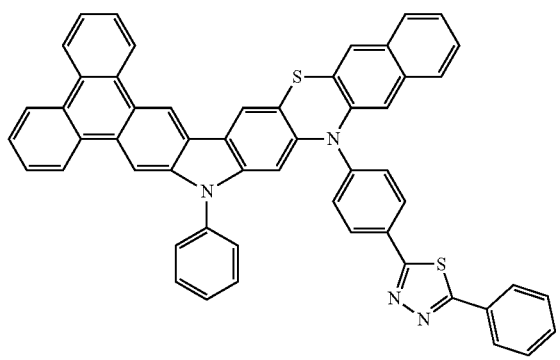

-continued
Compound 191
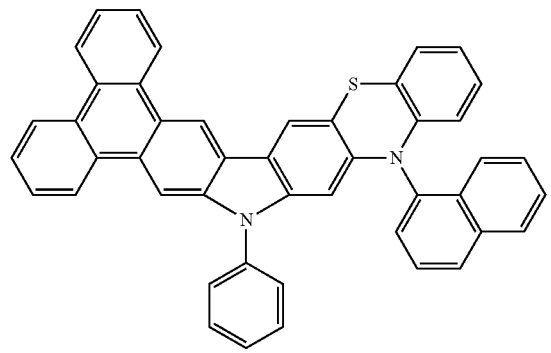
Compound 192
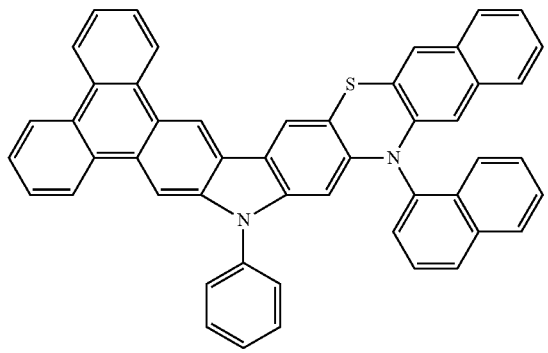
Compound 193
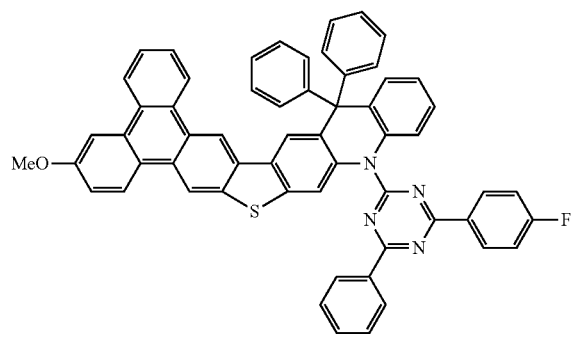
Compound 194
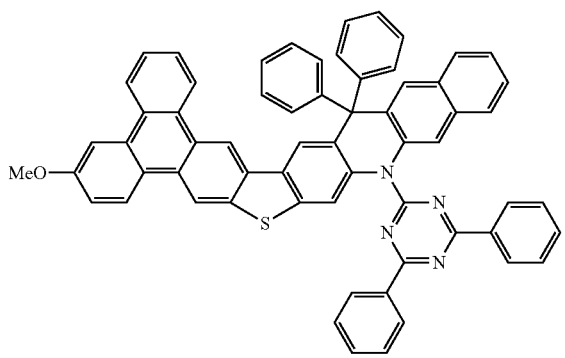
Compound 195
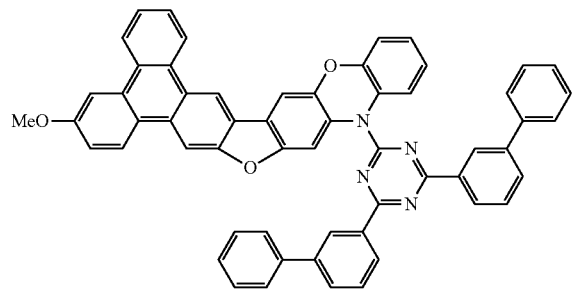
Compound 196
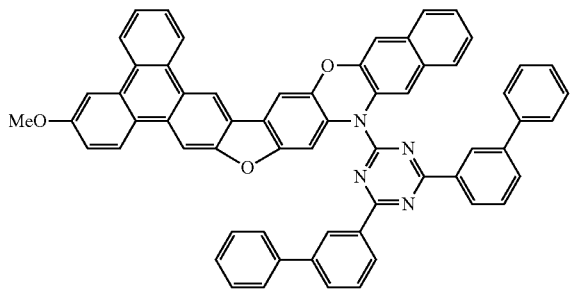
Compound 197
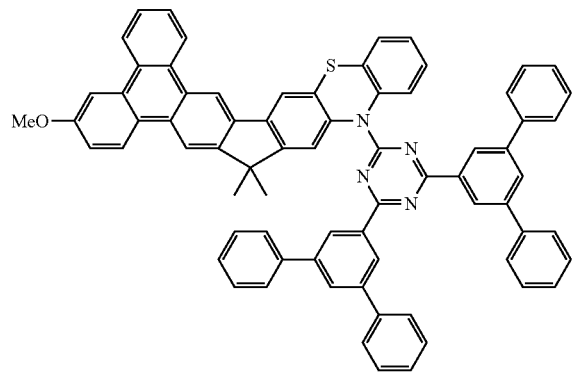
Compound 198
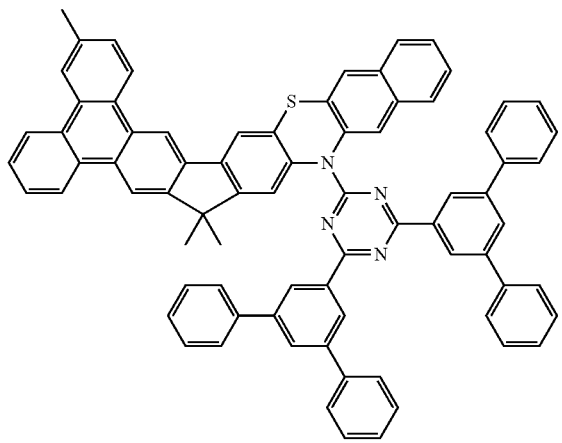

-continued
Compound 199
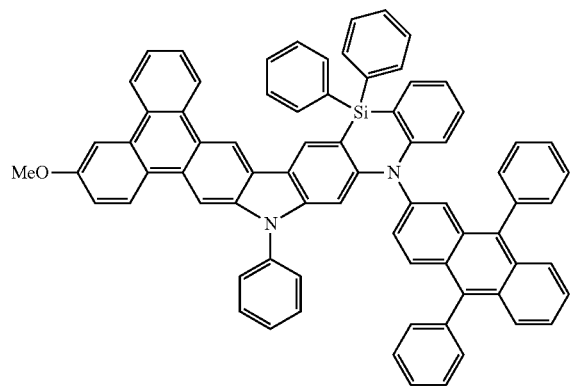
Compound 200
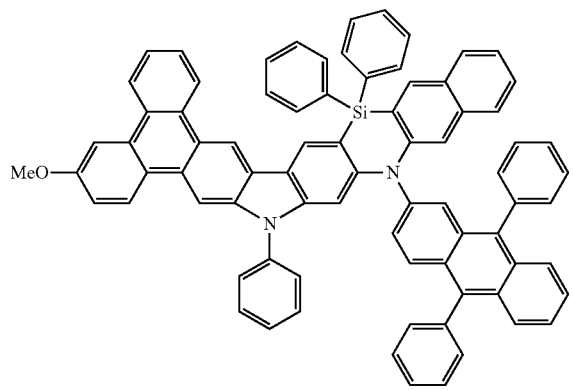
Compound 201
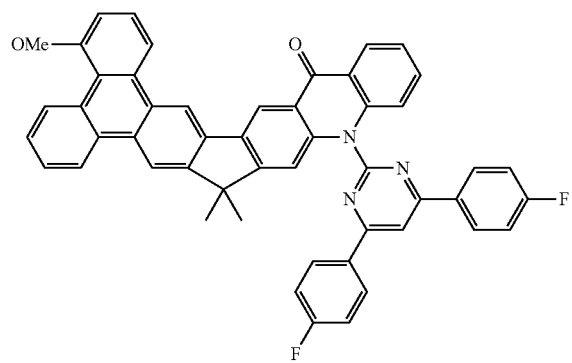
Compound 202
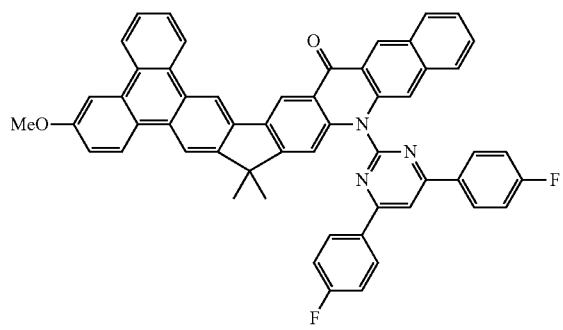
Compound 203
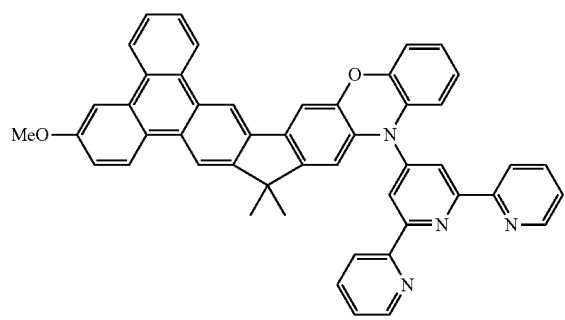
Compound 204
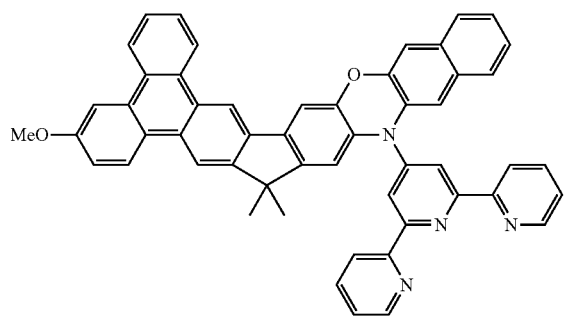
Compound 205
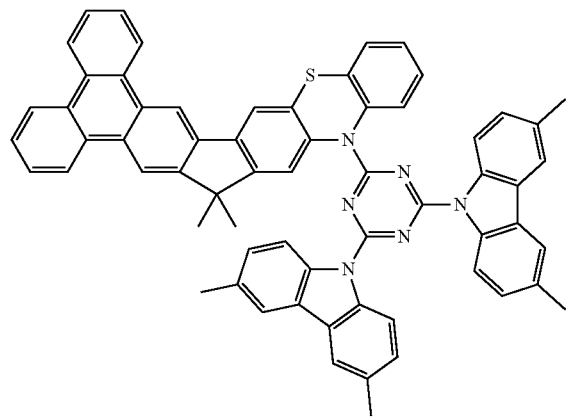
Compound 206
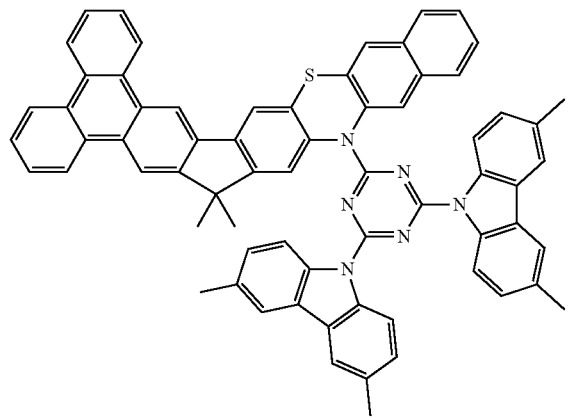

-continued
Compound 207
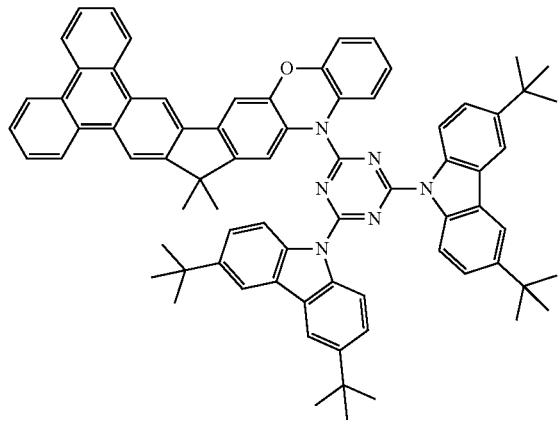
Compound 208
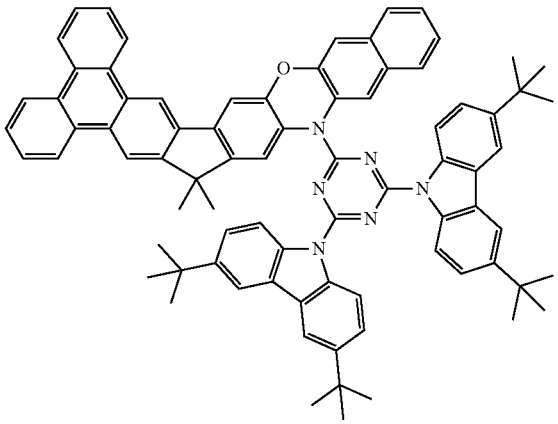
Compound 209
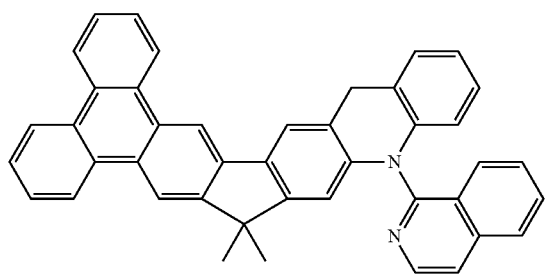
Compound 110
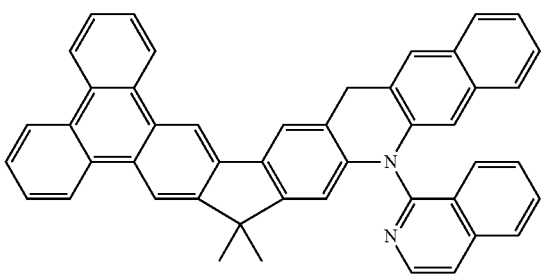
Compound 211
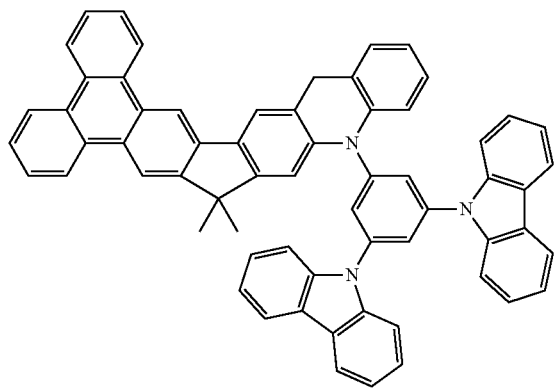
Compound 212
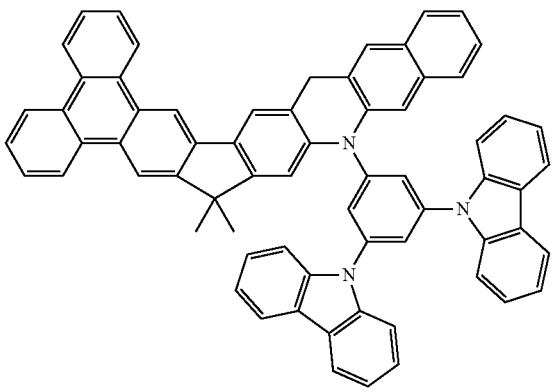
Compound 213
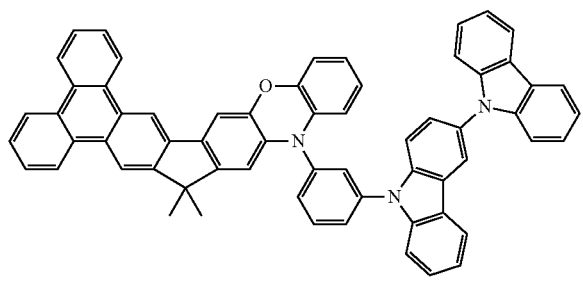
Compound 214
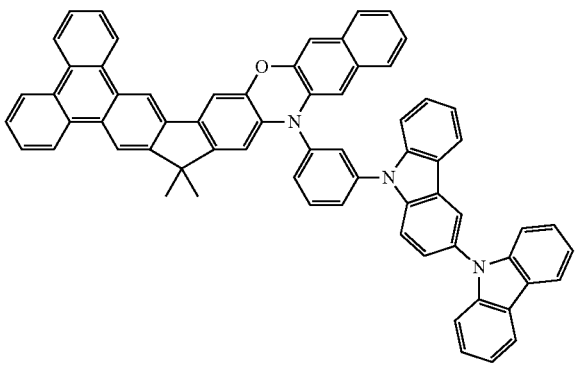

-continued
Compound 215
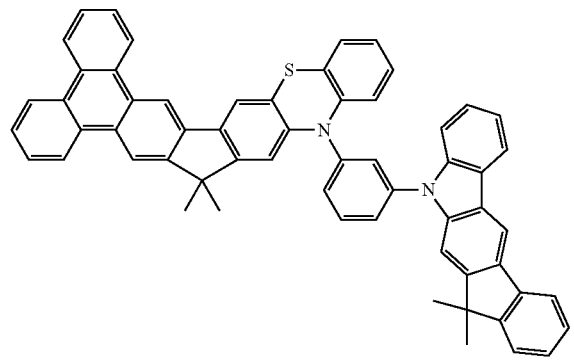
Compound 216
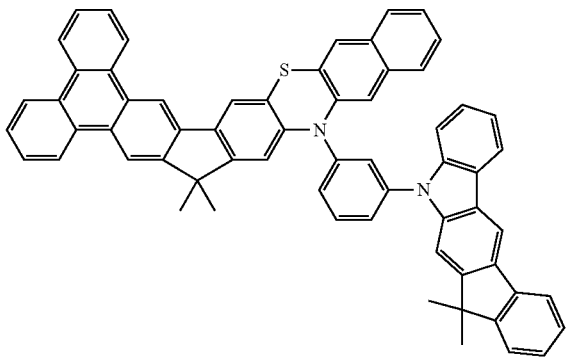
Compound 217
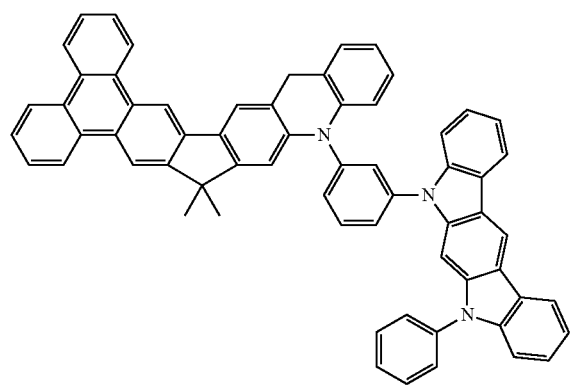
Compound 218
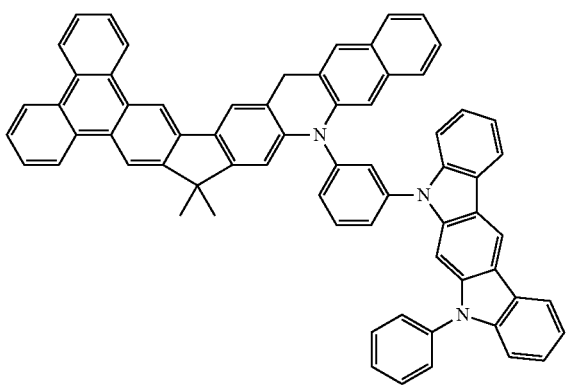
Compound 219
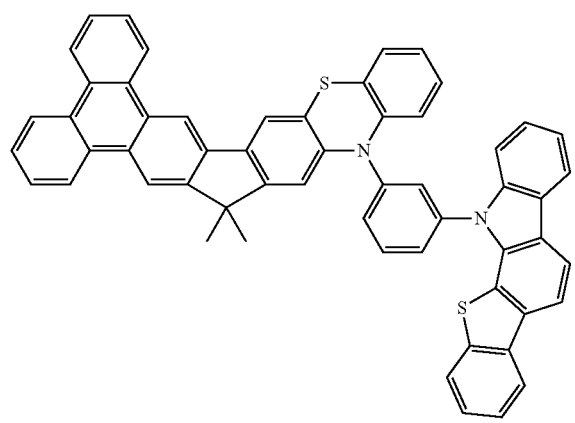
Compound 220
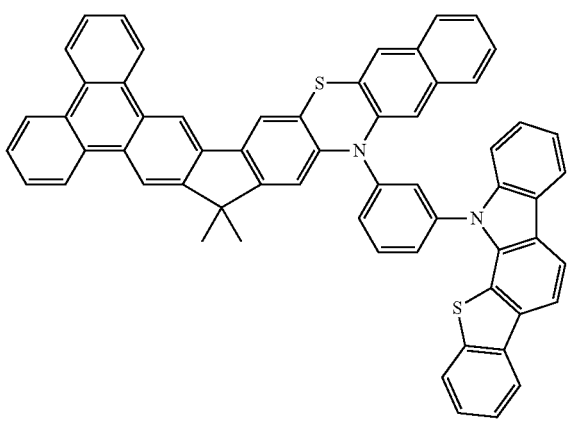

-continued
Compound 221
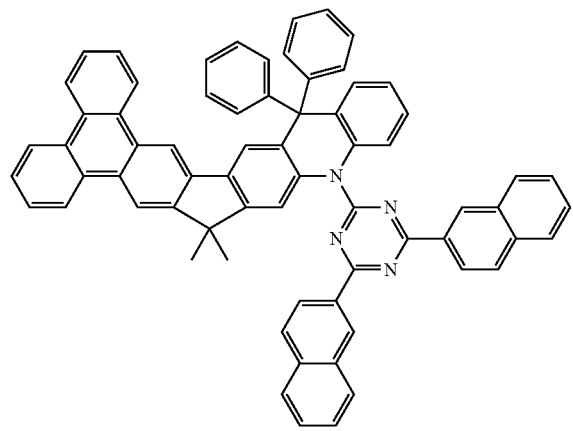
Compound 222
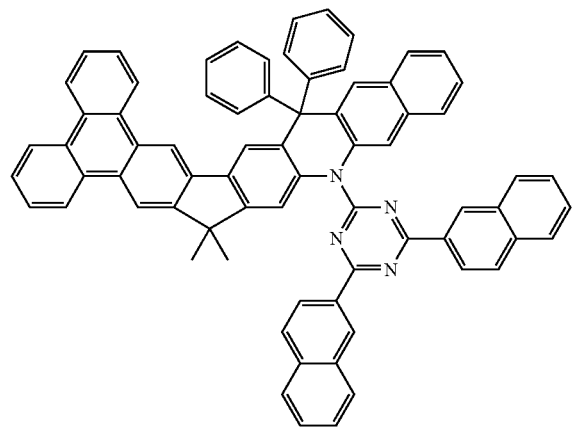
Compound 223
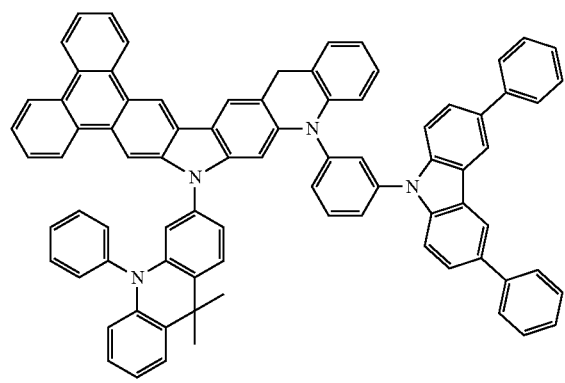
Compound 224
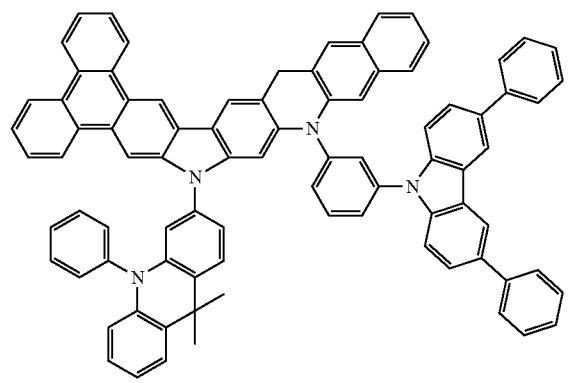
and
Compound 225
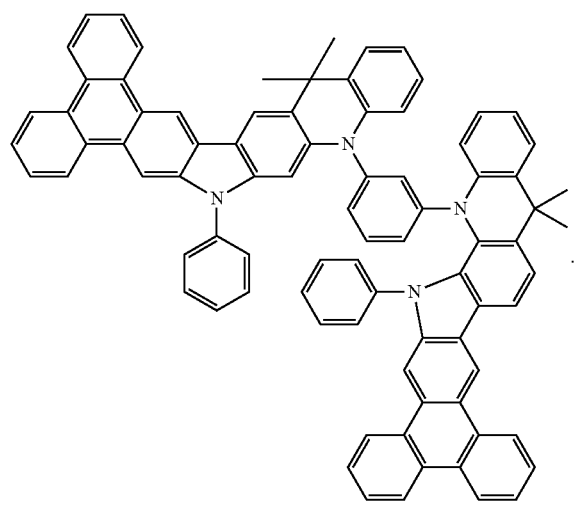

4. A organic electroluminescence device comprising a pair of electrodes consisting of a cathode and an anode, and between the pairs of electrodes comprising at least a light emitting layer, one or more layers of organic thin film layer, wherein the light emitting layer or the organic thin film layer comprising the material according to claim 1.

5. The organic electroluminescence device according to claim 4, wherein the light emitting layer comprising the material with a general formula(1) or formula(2) is a phosphorescent host material.

6. The organic electroluminescence device according to claim 4, wherein the light emitting layer comprising the material with a general formula(1) or formula(2) is a delayed fluorescence host material.

7. The organic electroluminescence device according to claim 4, wherein the light emitting layer comprising the material with a general formula(1) or formula(2) is a delayed fluorescence dopant material.

8. The organic electroluminescence device according to claim 4, wherein the organic thin film layer comprising the material with a general formula(1) or formula(2) is a hole blocking material.

9. The organic electroluminescence device according to claim 4, wherein the organic thin film layer comprising the material with a general formula(1) or formula(2) is an electron transport material.

10. The organic electroluminescence device according to claim 4, wherein the light emitting layer emits phosphorescent red, blue, green and yellow lights.

11. The organic electroluminescence device according to claim 4, wherein the light emitting layer emits delayed fluorescent red, blue, green and yellow lights.

12. The organic electroluminescence device according to claim 4, wherein the device is an organic light emitting device.

13. The organic electroluminescent device according to claim 4, wherein the device is a lighting panel.

14. The organic electroluminescent device according to claim 4, wherein the device is a backlight panel.

* * * * *